(12) United States Patent
Vilupuru et al.

(10) Patent No.: US 9,545,303 B2
(45) Date of Patent: Jan. 17, 2017

(54) OCULAR MASK HAVING SELECTIVE SPECTRAL TRANSMISSION

(71) Applicant: AcuFocus, Inc., Irvine, CA (US)

(72) Inventors: Abhiram S. Vilupuru, Rancho Santa Margarita, CA (US); Marie Dvorak Christ, Laguna Beach, CA (US)

(73) Assignee: AcuFocus, Inc., Irvine, CA (US)

( * ) Notice: Subject to any disclaimer, the term of this patent is extended or adjusted under 35 U.S.C. 154(b) by 476 days.

(21) Appl. No.: 13/691,625

(22) Filed: Nov. 30, 2012

(65) Prior Publication Data

US 2013/0268071 A1 Oct. 10, 2013

Related U.S. Application Data

(60) Provisional application No. 61/566,523, filed on Dec. 2, 2011.

(51) Int. Cl.
| | | |
|---|---|---|
| *A61F 2/16* | (2006.01) | |
| *G02C 7/02* | (2006.01) | |
| *A61F 9/04* | (2006.01) | |
| *A61B 3/10* | (2006.01) | |

(Continued)

(52) U.S. Cl.
CPC ............ *A61F 2/1613* (2013.01); *A61B 3/102* (2013.01); *A61F 2/14* (2013.01); *A61F 2/145* (2013.01); *A61F 2/1451* (2015.04); *A61F 9/04* (2013.01); *A61F 2/1659* (2013.01); *A61F 2250/0053* (2013.01); *G02C 7/165* (2013.01)

(58) Field of Classification Search
USPC ....................................................... 623/6.17
See application file for complete search history.

(56) References Cited

U.S. PATENT DOCUMENTS

| 564,518 A | 7/1896 | Heilborn |
|---|---|---|
| 1,034,516 A | 8/1912 | Samberg |
| 1,206,132 A | 11/1916 | Otte |

(Continued)

FOREIGN PATENT DOCUMENTS

| AR | 241 330 | 12/1992 |
|---|---|---|
| AR | 241 830 | 12/1992 |

(Continued)

OTHER PUBLICATIONS

Guyton A.C., Textbook of Medical Physiology, 7th Edition, W.B. Saunders Company, 1986: Chapter 58, pp. 700-710.

(Continued)

*Primary Examiner* — David H. Willse
*Assistant Examiner* — Tiffany Shipmon
(74) *Attorney, Agent, or Firm* — Knobbe Martens Olson & Bear LLP

(57) ABSTRACT

A mask is provided that is configured to increase the depth of focus of a patient. The mask can include an aperture configured to transmit along an optical axis substantially all visible incident light. The mask can further include a portion surrounding at least a portion of the aperture. The portion may be configured to be substantially opaque to visible electromagnetic radiation and be substantially transparent to electromagnetic radiation transmitted from an ocular examination device (e.g., substantially transparent to at least some non-visible electromagnetic radiation with a wavelength between about 750 nm and about 1500 nm).

27 Claims, 34 Drawing Sheets

(51) Int. Cl.
*A61F 2/14* (2006.01)
*G02C 7/16* (2006.01)

(56) References Cited

U.S. PATENT DOCUMENTS

| | | | |
|---|---|---|---|
| 1,959,915 A | 5/1934 | Guthrie |
| 2,129,305 A | 9/1938 | Feinbloom |
| 2,350,421 A | 6/1944 | Schoder et al. |
| 2,470,927 A | 5/1949 | Hale, Jr. |
| 2,714,721 A | 8/1955 | Stone, Jr. |
| 3,034,403 A | 5/1962 | Neefe |
| 3,074,407 A | 1/1963 | Moon et al. |
| 3,270,099 A | 8/1966 | Camp |
| 3,339,997 A | 9/1967 | Wesley |
| 3,392,727 A | 7/1968 | Hanlon |
| D212,868 S | 12/1968 | Olson |
| 3,458,870 A | 8/1969 | Stone, Jr. |
| 3,507,566 A | 4/1970 | Knapp |
| 3,536,386 A | 10/1970 | Spivack |
| 3,578,850 A | 5/1971 | Grant |
| 3,600,098 A | 8/1971 | Mohrman |
| 3,726,587 A | 4/1973 | Kendall |
| 3,776,230 A | 12/1973 | Neefe |
| 3,794,414 A | 2/1974 | Wesley |
| 3,852,032 A | 12/1974 | Urbach |
| 3,877,502 A | 4/1975 | Hunckler |
| 3,914,013 A | 10/1975 | Rosenberg |
| 3,946,982 A | 3/1976 | Calkins et al. |
| 3,982,541 A | 9/1976 | L'Esperance, Jr. |
| 3,996,627 A | 12/1976 | Deeg et al. |
| 4,010,496 A | 3/1977 | Neefe |
| 4,073,015 A | 2/1978 | Peyman |
| 4,099,529 A | 7/1978 | Peyman |
| 4,116,439 A | 9/1978 | Chavarria et al. |
| 4,138,191 A | 2/1979 | Peyman |
| 4,191,195 A | 3/1980 | Miller |
| 4,210,391 A | 7/1980 | Cohen |
| 4,272,191 A | 6/1981 | Bergkvist |
| 4,298,004 A | 11/1981 | Schchar et al. |
| 4,298,996 A | 11/1981 | Barnet |
| 4,312,575 A | 1/1982 | Peyman et al. |
| 4,340,283 A | 7/1982 | Cohen |
| 4,367,949 A | 1/1983 | Lavering |
| 4,383,843 A | 5/1983 | Iyenger |
| 4,402,579 A | 9/1983 | Poler |
| 4,402,681 A | 9/1983 | Haas et al. |
| 4,409,979 A | 10/1983 | Roussel et al. |
| 4,423,728 A | 1/1984 | Lieberman |
| 4,435,050 A | 3/1984 | Poler |
| 4,445,892 A | 5/1984 | Hussein et al. |
| 4,450,593 A | 5/1984 | Poler |
| 4,452,235 A | 6/1984 | Reynolds |
| 4,461,294 A | 7/1984 | Baron |
| 4,469,098 A | 9/1984 | Daui |
| 4,485,499 A | 12/1984 | Castleman |
| 4,505,855 A | 3/1985 | Bruns et al. |
| 4,528,311 A | 7/1985 | Beard et al. |
| 4,536,240 A | 8/1985 | Winn |
| 4,538,608 A | 9/1985 | L'Esperance, Jr. |
| 4,547,914 A | 10/1985 | Castleman |
| 4,547,915 A | 10/1985 | Castleman |
| 4,563,565 A | 1/1986 | Kampfer et al. |
| 4,573,998 A | 3/1986 | Mazzocco |
| 4,575,373 A | 3/1986 | Johnson |
| 4,575,915 A | 3/1986 | Clark et al. |
| 4,576,453 A | 3/1986 | Borowsky |
| 4,582,402 A | 4/1986 | Knapp |
| 4,607,617 A | 8/1986 | Choyce |
| 4,612,012 A | 9/1986 | White |
| 4,615,702 A | 10/1986 | Koziol et al. |
| 4,617,023 A | 10/1986 | Peyman |
| 4,624,669 A | 11/1986 | Grendahl |
| 4,633,866 A | 1/1987 | Peyman et al. |
| 4,636,049 A | 1/1987 | Blaker |
| 4,636,211 A | 1/1987 | Nielsen et al. |
| 4,636,212 A | 1/1987 | Posin et al. |
| 4,637,697 A | 1/1987 | Freeman |
| 4,639,105 A | 1/1987 | Neefe |
| 4,641,934 A | 2/1987 | Freeman |
| 4,642,112 A | 2/1987 | Freeman |
| 4,646,720 A | 3/1987 | Peyman |
| 4,648,400 A | 3/1987 | Schneider et al. |
| 4,655,774 A | 4/1987 | Choyce |
| 4,662,370 A | 5/1987 | Hoffmann et al. |
| 4,665,913 A | 5/1987 | L'Esperance, Jr. |
| 4,666,249 A | 5/1987 | Bauman et al. |
| 4,666,446 A | 5/1987 | Koziol et al. |
| 4,669,466 A | 6/1987 | L'Esperance, Jr. |
| 4,669,834 A | 6/1987 | Richter |
| 4,672,021 A | 6/1987 | Blumel et al. |
| 4,674,503 A | 6/1987 | Peyman et al. |
| 4,676,790 A | 6/1987 | Kern |
| 4,676,791 A | 6/1987 | Le Master et al. |
| 4,678,422 A | 7/1987 | York |
| 4,685,921 A | 8/1987 | Peyman |
| 4,685,922 A | 8/1987 | Peyman |
| 4,701,038 A | 10/1987 | Neefe |
| 4,702,574 A | 10/1987 | Bawa |
| 4,702,865 A | 10/1987 | Koziol et al. |
| 4,704,016 A | 11/1987 | de Carle |
| 4,710,003 A | 12/1987 | Masuda et al. |
| 4,713,446 A | 12/1987 | DeVore et al. |
| 4,715,858 A | 12/1987 | Lindstrom |
| 4,718,418 A | 1/1988 | L'Esperance |
| 4,729,372 A | 3/1988 | L'Esperance, Jr. |
| 4,729,373 A | 3/1988 | Peyman |
| 4,732,148 A | 3/1988 | L'Esperance, Jr. |
| 4,744,360 A | 5/1988 | Bath |
| 4,753,654 A | 6/1988 | Posin et al. |
| 4,767,647 A | 8/1988 | Bree |
| 4,779,973 A | 10/1988 | Miller et al. |
| 4,785,796 A | 11/1988 | Mattson |
| 4,785,810 A | 11/1988 | Baccala et al. |
| 4,787,903 A | 11/1988 | Grendahl |
| 4,795,462 A | 1/1989 | Grendahl |
| 4,796,623 A | 1/1989 | Krasner et al. |
| 4,798,608 A | 1/1989 | Grendahl |
| 4,799,478 A | 1/1989 | Fedorov et al. |
| 4,799,784 A | 1/1989 | Safir |
| 4,799,931 A | 1/1989 | Lindstrom |
| 4,799,973 A | 1/1989 | Mahulikar et al. |
| 4,806,382 A | 2/1989 | Goldberg et al. |
| 4,807,623 A | 2/1989 | Lieberman |
| 4,808,181 A | 2/1989 | Kelman |
| 4,813,955 A | 3/1989 | Achatz et al. |
| 4,814,050 A | 3/1989 | McGraw et al. |
| 4,817,789 A | 4/1989 | Paul |
| 4,838,266 A | 6/1989 | Koziol et al. |
| 4,840,175 A | 6/1989 | Peyman |
| 4,842,599 A | 6/1989 | Bronstein |
| 4,849,323 A | 7/1989 | Endo et al. |
| 4,851,003 A | 7/1989 | Lindstrom |
| 4,863,466 A | 9/1989 | Schlegel |
| 4,865,601 A | 9/1989 | Caldwell et al. |
| 4,869,587 A | 9/1989 | Breger |
| 4,878,910 A | 11/1989 | Koziol et al. |
| 4,881,860 A | 11/1989 | Kanazawa |
| 4,881,954 A | 11/1989 | Bikson et al. |
| 4,889,795 A | 12/1989 | Kaifu et al. |
| 4,890,913 A | 1/1990 | De Carle |
| 4,891,043 A | 1/1990 | Zeimer et al. |
| 4,892,543 A | 1/1990 | Turley |
| 4,898,461 A | 2/1990 | Portney |
| 4,903,695 A | 2/1990 | Warner et al. |
| 4,907,586 A | 3/1990 | Bille et al. |
| 4,923,297 A | 5/1990 | Arndt |
| 4,928,815 A | 5/1990 | Paul |
| 4,932,970 A | 6/1990 | Portney |
| 4,955,904 A | 9/1990 | Atebara et al. |
| 4,958,922 A | 9/1990 | Binh et al. |
| 4,959,070 A | 9/1990 | McDonald |
| 4,961,744 A | 10/1990 | Kilmer et al. |
| 4,965,545 A | 10/1990 | Johnson |
| 4,971,432 A | 11/1990 | Koeniger |

(56) References Cited

U.S. PATENT DOCUMENTS

| | | |
|---|---|---|
| 4,976,709 A | 12/1990 | Sand |
| 4,976,732 A | 12/1990 | Vorosmarthy |
| 4,983,181 A | 1/1991 | Civerchia |
| 4,985,559 A | 1/1991 | Goldberg et al. |
| 4,990,165 A | 2/1991 | Bikson et al. |
| 4,994,058 A | 2/1991 | Raven et al. |
| 4,994,080 A | 2/1991 | Shepard |
| 4,997,268 A | 3/1991 | Dauvergne |
| 5,002,571 A | 3/1991 | O'Donnell, Jr. |
| 5,013,319 A | 5/1991 | Davis |
| 5,019,097 A | 5/1991 | Knight et al. |
| 5,026,393 A | 6/1991 | Mackool |
| D318,117 S | 7/1991 | Michelson |
| 5,030,230 A | 7/1991 | White |
| 5,041,133 A | 8/1991 | Sayano et al. |
| 5,055,602 A | 10/1991 | Melpolder |
| 5,061,914 A | 10/1991 | Busch et al. |
| 5,063,942 A | 11/1991 | Kilmer et al. |
| 5,065,516 A | 11/1991 | Dulebohn |
| 5,067,961 A | 11/1991 | Kelman et al. |
| 5,076,684 A | 12/1991 | Simpson et al. |
| D323,891 S | 2/1992 | Arkel |
| 5,087,015 A | 2/1992 | Galley |
| 5,089,022 A | 2/1992 | Koester et al. |
| 5,089,024 A | 2/1992 | Christie et al. |
| 5,090,955 A | 2/1992 | Simon |
| 5,092,874 A | 3/1992 | Rogers |
| 5,094,521 A | 3/1992 | Jolson et al. |
| 5,098,443 A | 3/1992 | Parel et al. |
| 5,098,444 A | 3/1992 | Feaster |
| D325,500 S | 4/1992 | Dennis |
| 5,104,957 A | 4/1992 | Kelman et al. |
| 5,108,169 A | 4/1992 | Mandell |
| 5,108,428 A | 4/1992 | Capecchi et al. |
| 5,112,328 A | 5/1992 | Taboada et al. |
| 5,112,350 A | 5/1992 | Civerchia et al. |
| 5,116,111 A | 5/1992 | Simpson et al. |
| 5,119,555 A | 6/1992 | Johnson |
| 5,120,120 A | 6/1992 | Cohen |
| 5,120,121 A | 6/1992 | Rawlings et al. |
| 5,123,921 A | 6/1992 | Werblin et al. |
| 5,133,745 A | 7/1992 | Falcetta et al. |
| 5,137,441 A | 8/1992 | Fogarty |
| 5,139,518 A | 8/1992 | White |
| 5,147,395 A | 9/1992 | Willis |
| 5,149,331 A | 9/1992 | Ferdman et al. |
| 5,151,098 A | 9/1992 | Loertascher |
| 5,152,789 A | 10/1992 | Willis |
| 5,156,622 A | 10/1992 | Thompson |
| 5,158,572 A | 10/1992 | Nielsen |
| 5,160,463 A | 11/1992 | Evans et al. |
| 5,165,897 A | 11/1992 | Johnson |
| 5,166,712 A | 11/1992 | Portney |
| 5,171,318 A | 12/1992 | Gibson et al. |
| 5,172,143 A | 12/1992 | Baude et al. |
| 5,185,152 A | 2/1993 | Peyman |
| 5,188,125 A | 2/1993 | Kilmer et al. |
| 5,188,494 A | 2/1993 | Hatin |
| 5,192,316 A | 3/1993 | Ting |
| 5,192,318 A | 3/1993 | Schneider et al. |
| 5,196,026 A | 3/1993 | Barrett et al. |
| 5,196,027 A | 3/1993 | Thompson et al. |
| 5,201,762 A | 4/1993 | Hauber |
| 5,203,865 A | 4/1993 | Siepser |
| 5,213,749 A | 5/1993 | Huss et al. |
| 5,215,104 A | 6/1993 | Steinert |
| 5,219,844 A | 6/1993 | Peyman et al. |
| 5,225,858 A | 7/1993 | Portney |
| 5,239,066 A | 8/1993 | Falkow et al. |
| 5,245,367 A | 9/1993 | Miller et al. |
| 5,245,738 A | 9/1993 | Johnson |
| 5,258,412 A | 11/1993 | Peyman et al. |
| 5,260,727 A | 11/1993 | Oksman et al. |
| 5,261,997 A | 11/1993 | Inselmann |
| 5,266,241 A | 11/1993 | Parekh |
| 5,269,795 A | 12/1993 | Arnott |
| 5,269,812 A | 12/1993 | White |
| 5,270,744 A | 12/1993 | Portney |
| 5,274,404 A | 12/1993 | Michael |
| 5,282,971 A | 2/1994 | Degen et al. |
| 5,288,293 A | 2/1994 | O'Donnel, Jr. |
| 5,288,436 A | 2/1994 | Liu et al. |
| 5,290,301 A | 3/1994 | Lieberman |
| 5,292,514 A | 3/1994 | Capecchi et al. |
| 5,296,305 A | 3/1994 | Baude et al. |
| 5,296,881 A | 3/1994 | Freeman |
| D345,796 S | 4/1994 | Pernicka |
| 5,300,116 A | 4/1994 | Chirila et al. |
| 5,300,118 A | 4/1994 | Silvestrini et al. |
| 5,302,978 A | 4/1994 | Evans et al. |
| 5,306,297 A | 4/1994 | Rheinish et al. |
| 5,310,654 A | 5/1994 | Isberg et al. |
| 5,312,330 A | 5/1994 | Klopotek |
| 5,312,393 A | 5/1994 | Mastel |
| 5,312,424 A | 5/1994 | Kilmer et al. |
| 5,314,439 A | 5/1994 | Sugita |
| 5,314,961 A | 5/1994 | Anton et al. |
| 5,315,344 A | 5/1994 | Clark et al. |
| 5,318,044 A | 6/1994 | Kilmer et al. |
| 5,318,046 A | 6/1994 | Rozakis |
| 5,318,047 A | 6/1994 | Davenport et al. |
| 5,322,649 A | 6/1994 | Rheinish et al. |
| 5,323,788 A | 6/1994 | Silvestrini et al. |
| 5,325,880 A | 7/1994 | Johnson et al. |
| 5,332,802 A | 7/1994 | Kelman et al. |
| 5,336,261 A | 8/1994 | Barrett et al. |
| 5,346,689 A | 9/1994 | Peyman et al. |
| 5,354,331 A | 10/1994 | Scharcar |
| 5,358,520 A | 10/1994 | Patel |
| 5,366,499 A | 11/1994 | Py |
| 5,368,604 A | 11/1994 | Kilmer et al. |
| 5,372,580 A | 12/1994 | Simon et al. |
| 5,374,272 A | 12/1994 | Arpa et al. |
| D354,566 S | 1/1995 | Donahoo |
| 5,391,201 A | 2/1995 | Barrett et al. |
| 5,401,508 A | 3/1995 | Manesis |
| 5,403,335 A | 4/1995 | Loomas et al. |
| 5,405,384 A | 4/1995 | Silvestrini |
| 5,414,477 A | 5/1995 | Jahnke |
| 5,422,424 A | 6/1995 | Selsted et al. |
| 5,433,745 A | 7/1995 | Graham et al. |
| 5,434,630 A | 7/1995 | Bransome |
| 5,437,274 A | 8/1995 | Khoobehl et al. |
| 5,441,511 A | 8/1995 | Hanna |
| 5,458,819 A | 10/1995 | Chirila et al. |
| 5,466,260 A | 11/1995 | Silvestrini et al. |
| 5,474,548 A | 12/1995 | Knopp et al. |
| 5,475,452 A | 12/1995 | Kuhn et al. |
| 5,476,515 A | 12/1995 | Kelman et al. |
| 5,480,427 A | 1/1996 | Kelman et al. |
| 5,489,300 A | 2/1996 | Capecchi et al. |
| 5,496,339 A | 3/1996 | Koepnick |
| 5,505,722 A | 4/1996 | Kilmer et al. |
| 5,505,723 A | 4/1996 | Muller |
| 5,507,740 A | 4/1996 | O'Donnel, Jr. |
| 5,507,741 A | 4/1996 | L'Esperance, Jr. |
| 5,507,759 A | 4/1996 | Nordan |
| 5,509,922 A | 4/1996 | Aranyi et al. |
| 5,516,467 A | 5/1996 | Niwa et al. |
| 5,516,522 A | 5/1996 | Peyman et al. |
| 5,522,888 A | 6/1996 | Civerchia |
| 5,526,178 A | 6/1996 | Goldstein et al. |
| 5,527,356 A | 6/1996 | Peyman et al. |
| 5,527,524 A | 6/1996 | Tomalla et al. |
| 5,547,468 A | 8/1996 | Simon et al. |
| 5,547,473 A | 8/1996 | Peyman |
| 5,567,365 A | 10/1996 | Weinschenk, III et al. |
| D375,245 S | 11/1996 | Irving |
| 5,571,177 A | 11/1996 | Deacon et al. |
| 5,579,063 A | 11/1996 | Magnante et al. |
| RE35,421 E | 1/1997 | Ruiz et al. |
| 5,591,185 A | 1/1997 | Kilmer et al. |
| 5,592,246 A | 1/1997 | Kuhn et al. |
| 5,599,341 A | 2/1997 | Mathis et al. |

(56) References Cited

U.S. PATENT DOCUMENTS

| | | |
|---|---|---|
| 5,599,537 A | 2/1997 | Miller, III et al. |
| 5,603,774 A | 2/1997 | LeBoeuf et al. |
| 5,605,938 A | 2/1997 | Roufa et al. |
| 5,607,437 A | 3/1997 | Simon et al. |
| 5,607,472 A | 3/1997 | Thompson |
| 5,608,471 A | 3/1997 | Miller |
| 5,610,719 A | 3/1997 | Allen et al. |
| 5,624,456 A | 4/1997 | Hellenkamp |
| 5,627,613 A | 5/1997 | Kaneko |
| 5,628,794 A | 5/1997 | Lindstrom |
| 5,628,795 A | 5/1997 | Langerman |
| 5,628,798 A | 5/1997 | Eggleston et al. |
| 5,631,243 A | 5/1997 | Kelman et al. |
| 5,632,773 A | 5/1997 | Graham et al. |
| 5,643,249 A | 7/1997 | Amano et al. |
| 5,645,582 A | 7/1997 | Silvestrini et al. |
| 5,647,865 A | 7/1997 | Swinger |
| 5,653,752 A | 8/1997 | Silvestrini et al. |
| 5,662,706 A | 9/1997 | Legerton et al. |
| 5,662,908 A | 9/1997 | Falkow et al. |
| 5,672,885 A | 9/1997 | Allen et al. |
| 5,674,724 A | 10/1997 | Miller, III et al. |
| 5,674,736 A | 10/1997 | Miller, III et al. |
| 5,693,092 A | 12/1997 | Silvestrini et al. |
| 5,693,268 A | 12/1997 | Widman et al. |
| 5,695,983 A | 12/1997 | Miller et al. |
| 5,697,923 A | 12/1997 | Poler |
| 5,697,973 A | 12/1997 | Peyman et al. |
| 5,702,440 A | 12/1997 | Portney |
| 5,708,049 A | 1/1998 | Katagiri et al. |
| 5,713,844 A | 2/1998 | Peyman |
| 5,713,957 A | 2/1998 | Steele et al. |
| 5,719,656 A | 2/1998 | Bowling |
| 5,720,894 A | 2/1998 | Neev et al. |
| 5,722,971 A | 3/1998 | Peyman |
| 5,725,575 A | 3/1998 | O'Donnel, Jr. |
| 5,731,196 A | 3/1998 | Miller, III et al. |
| 5,731,862 A | 3/1998 | Winkler |
| 5,733,334 A | 3/1998 | Lee |
| 5,733,760 A | 3/1998 | Lu et al. |
| 5,746,558 A | 5/1998 | Nygren et al. |
| 5,752,960 A | 5/1998 | Nallakrishnan |
| 5,752,967 A | 5/1998 | Kritzinger et al. |
| 5,757,458 A | 5/1998 | Miller et al. |
| 5,766,171 A | 6/1998 | Silvestrini |
| 5,769,889 A | 6/1998 | Kelman |
| 5,771,088 A | 6/1998 | Perrott |
| 5,771,742 A | 6/1998 | Bokaie et al. |
| 5,774,202 A | 6/1998 | Abraham et al. |
| 5,782,911 A | 7/1998 | Herrick |
| 5,785,651 A | 7/1998 | Kuhn et al. |
| 5,786,883 A | 7/1998 | Miller et al. |
| 5,800,533 A | 9/1998 | Eggleston et al. |
| 5,806,530 A | 9/1998 | Herrick |
| 5,814,680 A | 9/1998 | Imafuku et al. |
| 5,824,086 A | 10/1998 | Silvestrini |
| 5,833,701 A | 11/1998 | Gordon |
| 5,836,313 A | 11/1998 | Perez et al. |
| 5,840,848 A | 11/1998 | Sturrock et al. |
| 5,843,105 A | 12/1998 | Mathis et al. |
| 5,843,186 A | 12/1998 | Christ |
| 5,846,186 A | 12/1998 | Upsher |
| 5,846,256 A | 12/1998 | Mathis et al. |
| 5,858,980 A | 1/1999 | Weiner et al. |
| 5,861,486 A | 1/1999 | DeVore et al. |
| 5,863,537 A | 1/1999 | Dalliet et al. |
| 5,864,128 A | 1/1999 | Plesko |
| 5,864,378 A | 1/1999 | Portney |
| 5,865,729 A | 2/1999 | Meehan et al. |
| 5,870,167 A | 2/1999 | Knopp et al. |
| 5,874,537 A | 2/1999 | Kelman et al. |
| 5,876,442 A | 3/1999 | Lipshitz et al. |
| 5,888,243 A | 3/1999 | Silvestrini |
| 5,895,610 A | 4/1999 | Chang et al. |
| 5,903,099 A | 5/1999 | Johnson et al. |
| 5,905,561 A | 5/1999 | Lee et al. |
| 5,910,537 A | 6/1999 | Feingold et al. |
| 5,913,898 A | 6/1999 | Feingold et al. |
| 5,919,185 A | 7/1999 | Peyman |
| 5,925,294 A | 7/1999 | Shibuya |
| 5,928,283 A | 7/1999 | Gross et al. |
| 5,929,968 A | 7/1999 | Cotie et al. |
| 5,935,140 A | 8/1999 | Buratto |
| 5,944,752 A | 8/1999 | Silvestrini |
| 5,960,812 A | 10/1999 | Johnson |
| 5,964,748 A | 10/1999 | Peyman |
| 5,964,776 A | 10/1999 | Peyman |
| 5,965,330 A | 10/1999 | Evans et al. |
| 5,968,062 A | 10/1999 | Thomas et al. |
| 5,980,040 A | 11/1999 | Xu et al. |
| 5,997,559 A | 12/1999 | Ziemer |
| 6,001,386 A | 12/1999 | Ashton et al. |
| 6,010,510 A | 1/2000 | Brown et al. |
| 6,010,901 A | 1/2000 | Miller, III et al. |
| 6,024,447 A | 2/2000 | Portney |
| 6,036,957 A | 3/2000 | Weiner et al. |
| D423,669 S | 4/2000 | Huttner |
| 6,050,999 A | 4/2000 | Paraschac et al. |
| 6,051,023 A | 4/2000 | Kilmer et al. |
| 6,063,073 A | 5/2000 | Peyman |
| 6,066,171 A | 5/2000 | Lipshitz et al. |
| 6,083,236 A | 7/2000 | Feingold |
| 6,086,204 A | 7/2000 | Magnante |
| 6,090,141 A | 7/2000 | Lindstrom |
| 6,096,077 A | 8/2000 | Callahan et al. |
| 6,102,946 A | 8/2000 | Nigam |
| 6,106,552 A | 8/2000 | Lacombe et al. |
| 6,106,553 A | 8/2000 | Feingold et al. |
| 6,110,166 A | 8/2000 | Juhasz |
| 6,125,294 A | 9/2000 | Scholl et al. |
| 6,126,286 A | 10/2000 | Portney |
| 6,138,307 A | 10/2000 | McDonald |
| 6,143,010 A | 11/2000 | Silvestrini |
| 6,152,959 A | 11/2000 | Portney |
| 6,161,544 A | 12/2000 | DeVore et al. |
| 6,164,282 A | 12/2000 | Gwon et al. |
| 6,164,777 A * | 12/2000 | Li .................. G02C 7/046 351/159.02 |
| 6,165,189 A | 12/2000 | Ziemer |
| 6,171,336 B1 | 1/2001 | Sawusch |
| 6,175,754 B1 | 1/2001 | Scholl et al. |
| 6,176,878 B1 | 1/2001 | Gwon et al. |
| 6,178,593 B1 | 1/2001 | Carlson |
| 6,183,498 B1 | 2/2001 | DeVore et al. |
| D439,338 S | 3/2001 | Huttner |
| 6,197,019 B1 | 3/2001 | Peyman |
| 6,197,057 B1 | 3/2001 | Peyman et al. |
| 6,197,934 B1 | 3/2001 | DeVore et al. |
| 6,203,538 B1 | 3/2001 | Peyman |
| 6,204,365 B1 | 3/2001 | DeVore et al. |
| 6,210,005 B1 | 4/2001 | Portney |
| 6,210,401 B1 | 4/2001 | Lai |
| 6,214,044 B1 | 4/2001 | Silvestrini |
| 6,217,571 B1 | 4/2001 | Peyman |
| 6,217,596 B1 | 4/2001 | Farah |
| 6,218,360 B1 | 4/2001 | Cintron et al. |
| 6,221,067 B1 | 4/2001 | Peyman |
| 6,221,105 B1 | 4/2001 | Portney |
| 6,228,113 B1 | 5/2001 | Kaufman |
| 6,228,114 B1 | 5/2001 | Lee |
| 6,228,115 B1 | 5/2001 | Hoffmann et al. |
| 6,231,582 B1 | 5/2001 | Gandianco et al. |
| 6,251,118 B1 | 6/2001 | Proudfoot et al. |
| 6,264,648 B1 | 7/2001 | Peyman |
| D447,237 S | 8/2001 | Huttner et al. |
| 6,277,146 B1 | 8/2001 | Peyman et al. |
| 6,280,449 B1 | 8/2001 | Blake |
| 6,280,470 B1 | 8/2001 | Peyman |
| 6,280,471 B1 | 8/2001 | Peyman |
| 6,283,595 B1 | 9/2001 | Breger |
| 6,302,877 B1 | 10/2001 | Ruiz |
| 6,304,390 B1 | 10/2001 | Takanashi |
| 6,308,590 B1 | 10/2001 | Berto |
| 6,312,424 B1 | 11/2001 | Largent |

(56) References Cited

U.S. PATENT DOCUMENTS

| | | |
|---|---|---|
| 6,316,153 B1 | 11/2001 | Goodman et al. |
| 6,335,006 B1 | 1/2002 | Miller |
| 6,357,875 B1 | 3/2002 | Herrick |
| 6,358,280 B1 | 3/2002 | Herrick |
| 6,361,560 B1 | 3/2002 | Nigam |
| 6,371,973 B1 | 4/2002 | Tepper |
| 6,387,379 B1 | 5/2002 | Goldberg et al. |
| 6,391,055 B1 | 5/2002 | Ikada et al. |
| 6,399,734 B1 | 6/2002 | Hodd et al. |
| 6,403,947 B1 | 6/2002 | Hoyt et al. |
| 6,406,494 B1 | 6/2002 | Laguette et al. |
| 6,413,276 B1 | 7/2002 | Werblin |
| 6,416,179 B1 | 7/2002 | Lieberman et al. |
| 6,423,093 B1 | 7/2002 | Hicks et al. |
| 6,425,917 B1 | 7/2002 | Blake |
| 6,432,246 B1 | 8/2002 | Blake |
| 6,436,092 B1 | 8/2002 | Peyman |
| 6,450,642 B1 | 9/2002 | Jethmalani et al. |
| 6,454,800 B2 | 9/2002 | Dalton et al. |
| 6,457,826 B1 | 10/2002 | Lett |
| 6,458,141 B1 | 10/2002 | Peyman |
| 6,461,384 B1 | 10/2002 | Hoffmann et al. |
| 6,470,108 B1 | 10/2002 | Johnson |
| 6,488,707 B1 | 12/2002 | Callahan et al. |
| 6,491,637 B2 | 12/2002 | Foster et al. |
| 6,494,910 B1 | 12/2002 | Ganem et al. |
| 6,497,700 B1 | 12/2002 | LaHaye |
| 6,503,276 B2 | 1/2003 | Lang et al. |
| 6,515,006 B2 | 2/2003 | Horn |
| 6,520,955 B2 | 2/2003 | Reynard |
| 6,527,389 B2 | 3/2003 | Portney |
| 6,533,905 B2 | 3/2003 | Johnson et al. |
| 6,536,899 B1 | 3/2003 | Fiala |
| 6,551,307 B2 | 4/2003 | Peyman |
| 6,554,424 B1 | 4/2003 | Miller et al. |
| 6,554,860 B2 | 4/2003 | Hoffmann et al. |
| 6,555,103 B2 | 4/2003 | Leukel et al. |
| 6,569,199 B1 | 5/2003 | Dotan et al. |
| 6,575,573 B2 | 6/2003 | Lai et al. |
| 6,581,993 B2 | 6/2003 | Nigam |
| RE38,193 E | 7/2003 | Bowling |
| 6,588,022 B1 | 7/2003 | Anders et al. |
| 6,588,902 B2 | 7/2003 | Isogai |
| 6,589,280 B1 | 7/2003 | Koziol |
| 6,592,621 B1 | 7/2003 | Domino |
| 6,596,026 B1 | 7/2003 | Gross et al. |
| 6,599,305 B1 | 7/2003 | Feingold |
| 6,607,527 B1 | 8/2003 | Ruiz et al. |
| 6,607,556 B1 | 8/2003 | Nigam |
| 6,613,088 B1 | 9/2003 | Babizhayev |
| 6,614,570 B2 | 9/2003 | Johnson et al. |
| 6,620,634 B2 | 9/2003 | Johnson et al. |
| 6,623,497 B1 | 9/2003 | Feingold |
| 6,623,522 B2 | 9/2003 | Nigam |
| 6,624,730 B2 | 9/2003 | Johnson et al. |
| 6,626,941 B2 | 9/2003 | Nigam |
| 6,632,244 B1 | 10/2003 | Nigam |
| 6,638,304 B2 | 10/2003 | Azar |
| 6,649,722 B2 | 11/2003 | Rosenzweig et al. |
| 6,655,804 B2 | 12/2003 | Streibig |
| 6,663,668 B1 | 12/2003 | Chaouk et al. |
| 6,669,795 B2 | 12/2003 | Johnson et al. |
| 6,673,112 B2 | 1/2004 | Nigam |
| 6,692,126 B1 | 2/2004 | Xie et al. |
| 6,702,807 B2 | 3/2004 | Peyman |
| 6,726,322 B2 | 4/2004 | Andino et al. |
| 6,729,599 B2 | 5/2004 | Johnson |
| 6,740,116 B2 | 5/2004 | Morcher |
| 6,742,761 B2 | 6/2004 | Johnson et al. |
| 6,746,890 B2 | 6/2004 | Gupta et al. |
| 6,749,632 B2 | 6/2004 | Jethmalani et al. |
| 6,755,819 B1 | 6/2004 | Waelti |
| 6,755,858 B1 | 6/2004 | White |
| D493,889 S | 8/2004 | Yoo |
| 6,786,926 B2 | 9/2004 | Peyman |
| 6,790,298 B2 | 9/2004 | Johnson et al. |
| 6,811,256 B1 | 11/2004 | Becherer et al. |
| 6,813,097 B2 | 11/2004 | Jethmalani et al. |
| 6,824,266 B2 | 11/2004 | Jethmalani et al. |
| 6,849,090 B2 | 2/2005 | Nigam |
| 6,851,804 B2 | 2/2005 | Jethmalani et al. |
| 6,855,163 B2 | 2/2005 | Peyman |
| 6,874,886 B2 | 4/2005 | Miller et al. |
| 6,899,424 B2 | 5/2005 | Miller et al. |
| 6,949,093 B1 | 9/2005 | Peyman |
| 6,951,556 B2 | 10/2005 | Epstein |
| 6,966,648 B2 | 11/2005 | Miller et al. |
| 6,976,997 B2 | 12/2005 | Noolandi et al. |
| 6,986,763 B2 | 1/2006 | Holmen |
| 6,989,008 B2 | 1/2006 | Peyman |
| 7,001,374 B2 | 2/2006 | Peyman |
| 7,008,447 B2 | 3/2006 | Koziol |
| 7,025,455 B2 | 4/2006 | Roffman |
| 7,061,693 B2 | 6/2006 | Zalevsky |
| 7,097,649 B2 | 8/2006 | Meyer |
| 7,099,057 B2 | 8/2006 | Parker et al. |
| 7,179,292 B2 | 2/2007 | Worst et al. |
| 7,207,998 B2 | 4/2007 | Feingold |
| 7,276,080 B2 | 10/2007 | Murakami et al. |
| 7,287,852 B2 | 10/2007 | Fiala |
| 7,364,674 B1 | 4/2008 | Hoover |
| D569,512 S | 5/2008 | Poll et al. |
| D571,915 S | 6/2008 | Poll et al. |
| 7,399,811 B2 | 7/2008 | Mentak et al. |
| 7,404,637 B2 | 7/2008 | Miller et al. |
| 7,404,638 B2 | 7/2008 | Miller et al. |
| 7,446,157 B2 | 11/2008 | Mentak et al. |
| 7,455,404 B2 | 11/2008 | Bandhauer et al. |
| 7,455,691 B2 | 11/2008 | Feingold et al. |
| 7,462,194 B1 | 12/2008 | Blake |
| 7,491,350 B2 | 2/2009 | Silvestrini |
| D589,615 S | 3/2009 | Doenges |
| 7,497,866 B2 | 3/2009 | Perez |
| 7,628,810 B2 | 12/2009 | Christie et al. |
| 7,641,337 B2 | 1/2010 | Altmann |
| 7,645,291 B2 | 1/2010 | Ross et al. |
| 7,645,299 B2 | 1/2010 | Koziol |
| 7,745,555 B2 | 6/2010 | Mentak et al. |
| 7,828,844 B2 | 11/2010 | Marmo et al. |
| 7,842,367 B2 | 11/2010 | Mentak |
| 7,976,577 B2 | 7/2011 | Silvestrini |
| D645,337 S | 9/2011 | Hsu et al. |
| 8,043,371 B2 | 10/2011 | Paul et al. |
| 8,048,972 B2 | 11/2011 | Mentak et al. |
| 8,079,706 B2 | 12/2011 | Silvestrini et al. |
| D656,526 S | 3/2012 | Christie et al. |
| 8,287,592 B2 | 10/2012 | Silvestrini |
| 8,343,215 B2 | 1/2013 | Miller et al. |
| D681,086 S | 4/2013 | Christie et al. |
| 8,420,753 B2 | 4/2013 | Mentak et al. |
| 8,460,374 B2 | 6/2013 | Christie et al. |
| 8,604,098 B2 | 12/2013 | Boydston et al. |
| 8,740,978 B2 | 6/2014 | Weeber et al. |
| 8,752,958 B2 | 6/2014 | Miller et al. |
| 8,858,624 B2 | 10/2014 | Christie et al. |
| 8,864,824 B2 | 10/2014 | Silvestrini et al. |
| 9,005,281 B2 | 4/2015 | Christie et al. |
| 9,138,142 B2 | 9/2015 | Christie et al. |
| 9,204,962 B2 | 12/2015 | Silvestrini |
| 2001/0004702 A1 | 6/2001 | Peyman |
| 2001/0027314 A1 | 10/2001 | Peyman |
| 2001/0034516 A1 | 10/2001 | Peyman |
| 2001/0047203 A1 | 11/2001 | Dalton et al. |
| 2001/0050750 A1 | 12/2001 | Breger |
| 2002/0010510 A1 | 1/2002 | Silvestrini |
| 2002/0016629 A1 | 2/2002 | Sandstedt et al. |
| 2002/0028330 A1 | 3/2002 | Patel et al. |
| 2002/0042004 A1 | 4/2002 | Sandstedt et al. |
| 2002/0055753 A1 | 5/2002 | Silvestrini |
| 2002/0057148 A1 | 5/2002 | Johnson et al. |
| 2002/0075447 A1 | 6/2002 | Andino et al. |
| 2002/0082288 A1 | 6/2002 | Horn |
| 2002/0107337 A1 | 8/2002 | Rosenzweig et al. |
| 2002/0107566 A1 | 8/2002 | Nigam |

(56) References Cited

U.S. PATENT DOCUMENTS

| | | |
|---|---|---|
| 2002/0111677 A1 | 8/2002 | Nigam |
| 2002/0120329 A1 | 8/2002 | Lang et al. |
| 2002/0128710 A1 | 9/2002 | Eggleston |
| 2002/0133228 A1 | 9/2002 | Sarver |
| 2002/0138070 A1 | 9/2002 | Peyman |
| 2002/0167640 A1 | 11/2002 | Francis et al. |
| 2002/0167735 A1 | 11/2002 | Jethmalani et al. |
| 2002/0169491 A1 | 11/2002 | Foster et al. |
| 2002/0169505 A1 | 11/2002 | Jethmalani et al. |
| 2002/0173846 A1 | 11/2002 | Blake et al. |
| 2002/0188351 A1 | 12/2002 | Laguette |
| 2002/0196409 A1 | 12/2002 | Jani |
| 2003/0002994 A1 | 1/2003 | Johnson et al. |
| 2003/0007122 A1 | 1/2003 | Streibig |
| 2003/0014021 A1 | 1/2003 | Holmen |
| 2003/0014042 A1 | 1/2003 | Juhasz et al. |
| 2003/0014107 A1 | 1/2003 | Reynard |
| 2003/0033013 A1 | 2/2003 | Callahan et al. |
| 2003/0045930 A1 | 3/2003 | Nguyen |
| 2003/0048411 A1 | 3/2003 | Jethmalani et al. |
| 2003/0055497 A1 | 3/2003 | Hicks et al. |
| 2003/0071893 A1 | 4/2003 | Miller et al. |
| 2003/0078655 A1 | 4/2003 | Callahan et al. |
| 2003/0088313 A1 | 5/2003 | Nigam |
| 2003/0090013 A1 | 5/2003 | Jethmalani et al. |
| 2003/0090624 A1 | 5/2003 | Jethmalani et al. |
| 2003/0093083 A1 | 5/2003 | Peyman |
| 2003/0093150 A1 | 5/2003 | Jethmalani et al. |
| 2003/0105521 A1 | 6/2003 | Perez |
| 2003/0115718 A1 | 6/2003 | Bechthold |
| 2003/0127318 A1 | 7/2003 | Johnson et al. |
| 2003/0128336 A1 | 7/2003 | Jethmalani et al. |
| 2003/0135272 A1 | 7/2003 | Brady et al. |
| 2003/0149480 A1 | 8/2003 | Shadduck |
| 2003/0151825 A1 | 8/2003 | Bielawski et al. |
| 2003/0151831 A1 | 8/2003 | Sandstedt et al. |
| 2003/0174375 A1 | 9/2003 | Jethmalani et al. |
| 2003/0176521 A1 | 9/2003 | Jethmalani et al. |
| 2003/0204258 A1 | 10/2003 | Graham et al. |
| 2003/0216763 A1 | 11/2003 | Patel |
| 2003/0220653 A1 | 11/2003 | Perez |
| 2004/0014253 A1 | 1/2004 | Gupta et al. |
| 2004/0015234 A1 | 1/2004 | Peyman |
| 2004/0019379 A1 | 1/2004 | Glick et al. |
| 2004/0047014 A1 | 3/2004 | Parker et al. |
| 2004/0056371 A1 | 3/2004 | Liao et al. |
| 2004/0068317 A1 | 4/2004 | Knight |
| 2004/0078075 A1 | 4/2004 | Koziol |
| 2004/0080239 A1 | 4/2004 | Gupta et al. |
| 2004/0086479 A1 | 5/2004 | Grinstaff et al. |
| 2004/0106929 A1 | 6/2004 | Masket |
| 2004/0243231 A1 | 12/2004 | Koziol |
| 2005/0027355 A1 | 2/2005 | Murakami |
| 2005/0031697 A1 | 2/2005 | Vehige et al. |
| 2005/0046794 A1 | 3/2005 | Silvestrini et al. |
| 2005/0049621 A1 | 3/2005 | Feingold et al. |
| 2005/0080485 A1 | 4/2005 | Nigam |
| 2005/0090895 A1 | 4/2005 | Peyman |
| 2005/0099597 A1 | 5/2005 | Sandstedt et al. |
| 2005/0119738 A1 | 6/2005 | Nigam |
| 2005/0124983 A1 | 6/2005 | Fret et al. |
| 2005/0137703 A1 | 6/2005 | Chen |
| 2005/0143717 A1 | 6/2005 | Peyman |
| 2005/0143751 A1 | 6/2005 | Makker et al. |
| 2005/0143812 A1 | 6/2005 | Paul et al. |
| 2005/0182488 A1 | 8/2005 | Peyman |
| 2005/0187621 A1 | 8/2005 | Brady |
| 2005/0222679 A1 | 10/2005 | Peyman |
| 2005/0228376 A1 | 10/2005 | Boomer et al. |
| 2005/0246015 A1 | 11/2005 | Miller |
| 2005/0246016 A1 | 11/2005 | Miller et al. |
| 2005/0246019 A1 | 11/2005 | Blake et al. |
| 2005/0288784 A1 | 12/2005 | Peyman |
| 2006/0064077 A1 | 3/2006 | Peyman |
| 2006/0079959 A1 | 4/2006 | Christie et al. |
| 2006/0079960 A1 | 4/2006 | Christie et al. |
| 2006/0095127 A1 | 5/2006 | Feingold et al. |
| 2006/0113054 A1 | 6/2006 | Silvestrini |
| 2006/0184243 A1* | 8/2006 | Yilmaz ..................... 623/4.1 |
| 2006/0232665 A1* | 10/2006 | Schowengerdt ... G02B 27/0093 348/51 |
| 2006/0235428 A1 | 10/2006 | Silvestrini |
| 2006/0235514 A1* | 10/2006 | Silvestrini ................ A61F 2/14 351/159.6 |
| 2006/0241751 A1 | 10/2006 | Marmo et al. |
| 2006/0252844 A1* | 11/2006 | Mentak ........................ 523/106 |
| 2006/0265058 A1 | 11/2006 | Silvestrini |
| 2006/0268226 A1 | 11/2006 | Christie et al. |
| 2006/0268227 A1 | 11/2006 | Christie et al. |
| 2006/0268228 A1 | 11/2006 | Christie et al. |
| 2006/0268229 A1 | 11/2006 | Silvestrini et al. |
| 2006/0270946 A1 | 11/2006 | Silvestrini et al. |
| 2006/0271026 A1 | 11/2006 | Silvestrini et al. |
| 2006/0271027 A1 | 11/2006 | Silvestrini et al. |
| 2006/0271176 A1 | 11/2006 | Christie et al. |
| 2006/0271177 A1 | 11/2006 | Christie et al. |
| 2006/0271178 A1 | 11/2006 | Christie et al. |
| 2006/0271179 A1 | 11/2006 | Christie et al. |
| 2006/0271180 A1 | 11/2006 | Christie et al. |
| 2006/0271181 A1 | 11/2006 | Christie et al. |
| 2006/0271182 A1 | 11/2006 | Christie et al. |
| 2006/0271183 A1 | 11/2006 | Christie et al. |
| 2006/0271184 A1 | 11/2006 | Silvestrini |
| 2006/0271185 A1 | 11/2006 | Silvestrini |
| 2006/0274264 A1 | 12/2006 | Christie et al. |
| 2006/0274265 A1 | 12/2006 | Christie et al. |
| 2007/0016234 A1 | 1/2007 | Daxer |
| 2007/0032866 A1 | 2/2007 | Portney |
| 2007/0092592 A1 | 4/2007 | Chiang |
| 2007/0129797 A1 | 6/2007 | Lang et al. |
| 2007/0219542 A1 | 9/2007 | Yahagi |
| 2007/0225691 A1 | 9/2007 | Silvestrini et al. |
| 2008/0033546 A1 | 2/2008 | Liang |
| 2008/0077238 A1 | 3/2008 | Deacon et al. |
| 2008/0100921 A1 | 5/2008 | Nishikawa |
| 2008/0125862 A1 | 5/2008 | Blake |
| 2008/0151183 A1 | 6/2008 | Altmann |
| 2008/0212030 A1 | 9/2008 | Bentley et al. |
| 2008/0221674 A1 | 9/2008 | Blum et al. |
| 2008/0255663 A1 | 10/2008 | Akpek et al. |
| 2008/0275462 A1 | 11/2008 | Feingold |
| 2008/0306587 A1 | 12/2008 | Your |
| 2009/0012505 A1 | 1/2009 | Chernyak |
| 2009/0021692 A1 | 1/2009 | Miller et al. |
| 2009/0059168 A1 | 3/2009 | Miller et al. |
| 2009/0069817 A1 | 3/2009 | Peyman |
| 2009/0171458 A1 | 7/2009 | Kellan et al. |
| 2009/0204207 A1 | 8/2009 | Blum et al. |
| 2009/0222086 A1 | 9/2009 | Lui et al. |
| 2009/0234448 A1 | 9/2009 | Weeber et al. |
| 2009/0306773 A1 | 12/2009 | Silversrini et al. |
| 2010/0082100 A1 | 4/2010 | Mikawa |
| 2010/0312336 A1 | 12/2010 | Hong et al. |
| 2011/0040376 A1* | 2/2011 | Christie ................ A61F 2/1613 623/6.17 |
| 2011/0125261 A1 | 5/2011 | Portney |
| 2011/0172675 A1 | 7/2011 | Danta et al. |
| 2011/0251685 A1 | 10/2011 | Chu |
| 2012/0109294 A1 | 5/2012 | Olson |
| 2012/0143325 A1 | 6/2012 | Christie et al. |
| 2012/0203239 A1 | 8/2012 | Vukich et al. |
| 2012/0245683 A1 | 9/2012 | Christie et al. |
| 2012/0310338 A1 | 12/2012 | Christie et al. |
| 2013/0053953 A1 | 2/2013 | Silvestrini |
| 2013/0103147 A1 | 4/2013 | Christie et al. |
| 2013/0131795 A1 | 5/2013 | Miller et al. |
| 2013/0238091 A1 | 9/2013 | Danta et al. |
| 2014/0131905 A1 | 5/2014 | Webb |
| 2014/0264981 A1 | 9/2014 | Reboul et al. |
| 2014/0379078 A1 | 12/2014 | Trindade |
| 2015/0025627 A1 | 1/2015 | Christie et al. |
| 2015/0073549 A1 | 3/2015 | Webb et al. |

(56) References Cited

U.S. PATENT DOCUMENTS

| | | | |
|---|---|---|---|
| 2015/0366658 A1 | 12/2015 | Christie et al. | |
| 2016/0081794 A1 | 3/2016 | Silvestrini | |

FOREIGN PATENT DOCUMENTS

| | | |
|---|---|---|
| AR | 244 890 | 11/1993 |
| AU | 739297 | 1/2002 |
| AU | 2004201751 | 5/2004 |
| AU | 0772492 | 8/2004 |
| AU | 778310 | 3/2005 |
| AU | 2003252004 | 3/2010 |
| AU | 2006236715 | 6/2012 |
| BR | 0008601 A | 12/2001 |
| BR | 0008624 A | 12/2001 |
| BR | PI-9809289-8 | 12/2006 |
| CA | 2286718 | 11/2008 |
| CN | 1253484 A | 5/2000 |
| CN | 1875895 | 12/2006 |
| CN | 101198294 | 6/2008 |
| CN | 101198364 | 6/2008 |
| CN | 101322663 | 12/2008 |
| CN | 102448404 | 5/2012 |
| CN | 102470033 A | 5/2012 |
| DE | 3433581 | 3/1986 |
| DE | 41 34 320 A1 | 4/1992 |
| EP | 0165652 | 12/1985 |
| EP | 0225098 | 6/1987 |
| EP | 0286433 | 10/1988 |
| EP | 0443094 A2 | 8/1991 |
| EP | 0457553 A2 | 11/1991 |
| EP | 0941717 | 9/1999 |
| EP | 1014872 | 7/2000 |
| EP | 1173790 | 1/2002 |
| EP | 1267998 | 1/2003 |
| EP | 1381326 | 1/2004 |
| EP | 1871298 | 4/2006 |
| EP | 1674049 | 6/2006 |
| EP | 1548489 B1 | 8/2006 |
| EP | 1159033 | 1/2007 |
| EP | 1827330 | 9/2007 |
| EP | 1845896 | 10/2007 |
| EP | 1890736 | 2/2008 |
| EP | 1158936 | 7/2008 |
| EP | 1997530 | 12/2008 |
| EP | 1534188 | 9/2010 |
| EP | 2258311 | 12/2010 |
| EP | 2301477 | 3/2011 |
| EP | 2319457 | 5/2011 |
| EP | 1635739 | 9/2011 |
| EP | 2243052 B1 | 9/2011 |
| EP | 2365379 | 9/2011 |
| EP | 2455799 | 5/2012 |
| EP | 2464310 | 6/2012 |
| EP | 2464311 | 6/2012 |
| EP | 2506803 | 10/2012 |
| EP | 2823789 | 1/2015 |
| EP | 2364457 B1 | 8/2015 |
| FR | 369 993 | 1/1907 |
| FR | 1115140 | 12/1955 |
| FR | 1400566 | 4/1965 |
| FR | 2599156 | 5/1986 |
| FR | 2620687 | 3/1989 |
| FR | 2649605 | 1/1991 |
| GB | 1 026 839 | 4/1966 |
| GB | 1276003 | 6/1972 |
| GB | 1 547 525 | 6/1979 |
| GB | 2242835 | 10/1991 |
| HK | 1028531 | 2/2011 |
| HK | 1151451 | 2/2012 |
| HK | 11553484 | 5/2012 |
| HK | 1166457 A | 11/2012 |
| HK | 1169935 A | 2/2013 |
| JP | 62167343 A | 7/1987 |
| JP | 63-17096 | 4/1988 |
| JP | 64-002644 | 1/1989 |
| JP | 1990-7954 | 1/1990 |
| JP | 03-001857 | 1/1991 |
| JP | 04-158859 | 6/1992 |
| JP | 04-223425 | 8/1992 |
| JP | H05-65340 | 9/1993 |
| JP | 6-502782 | 3/1994 |
| JP | 6-509731 | 11/1994 |
| JP | 07-050242 | 2/1995 |
| JP | H07-067896 | 3/1995 |
| JP | 07-178125 | 7/1995 |
| JP | 07-265340 | 10/1995 |
| JP | 08-103457 | 4/1996 |
| JP | 09-502542 | 3/1997 |
| JP | 11-503657 | 8/1997 |
| JP | 2002-14772 | 1/2002 |
| JP | 2002-537895 | 11/2002 |
| JP | 2003-502109 | 1/2003 |
| JP | 2003-527228 | 9/2003 |
| JP | 2004-510199 | 4/2004 |
| JP | 2004-538034 | 12/2004 |
| JP | 2007-523720 | 8/2007 |
| JP | 2008-506710 | 3/2008 |
| JP | 4114036 | 4/2008 |
| JP | 2008-517671 | 5/2008 |
| JP | S59-54527 | 5/2008 |
| JP | 2008-536574 | 9/2008 |
| JP | 2008-536576 | 9/2008 |
| JP | 4182390 | 9/2008 |
| JP | 2010-227615 | 10/2010 |
| JP | 2010-126600 | 2/2011 |
| JP | 4676761 | 2/2011 |
| JP | 4689615 | 2/2011 |
| JP | 4746052 | 5/2011 |
| KR | 10-0335722 | 5/2002 |
| KR | 600210 | 7/2006 |
| MX | 1008759 A | 7/2003 |
| MX | 226369 | 2/2005 |
| MX | 227913 | 3/2006 |
| NZ | 562987 | 2/2010 |
| RU | 1380743 A1 | 3/1998 |
| RU | 2138837 C1 | 9/1999 |
| SG | 68726 | 2/2002 |
| SG | 83306 | 2/2004 |
| SG | 83307 | 7/2004 |
| SG | 200716909-7 | 3/2011 |
| WO | WO 87/05797 | 10/1987 |
| WO | WO 87/07165 | 12/1987 |
| WO | WO 91/16865 | 11/1991 |
| WO | WO 92/05694 | 4/1992 |
| WO | WO 93/03776 | 3/1993 |
| WO | WO 93/08878 | 5/1993 |
| WO | WO 93/12735 | 7/1993 |
| WO | WO 93/20763 | 10/1993 |
| WO | WO 94/01058 | 1/1994 |
| WO | WO 94/05232 | 3/1994 |
| WO | WO 94/23327 | 10/1994 |
| WO | WO 95/02356 | 1/1995 |
| WO | WO 95/03747 | 2/1995 |
| WO | WO 95/08135 | 3/1995 |
| WO | WO 96/35397 | 11/1996 |
| WO | WO 97/28759 | 8/1997 |
| WO | WO 97/48004 | 12/1997 |
| WO | WO 97/48005 | 12/1997 |
| WO | WO 98/27896 | 7/1998 |
| WO | WO 98/48715 | 11/1998 |
| WO | WO 99/07309 | 2/1999 |
| WO | WO 00/25704 | 5/2000 |
| WO | WO 00/38594 | 7/2000 |
| WO | WO 00/51682 | 9/2000 |
| WO | WO 00/52516 A2 | 9/2000 |
| WO | WO 01/10641 A | 2/2001 |
| WO | WO 01/15779 | 3/2001 |
| WO | WO 01/17460 | 3/2001 |
| WO | WO 01/19364 | 3/2001 |
| WO | WO 01/82815 | 11/2001 |
| WO | WO 01/87189 | 11/2001 |
| WO | WO 02/13881 | 2/2002 |
| WO | WO 02/27388 | 4/2002 |
| WO | WO 02/076320 | 10/2002 |

(56) References Cited

FOREIGN PATENT DOCUMENTS

| | | |
|---|---|---|
| WO | WO 02/102241 A2 | 12/2002 |
| WO | WO 03/020177 | 3/2003 |
| WO | WO 03/022168 | 3/2003 |
| WO | WO 03/030763 A1 | 4/2003 |
| WO | WO 03/061518 A2 | 7/2003 |
| WO | WO 2004/014969 | 2/2004 |
| WO | WO 2004/034917 | 4/2004 |
| WO | WO 2004/050132 | 6/2004 |
| WO | WO 2004/105588 A2 | 12/2004 |
| WO | WO 2004/113959 | 12/2004 |
| WO | WO 2005/033263 | 4/2005 |
| WO | WO 2005/082265 | 9/2005 |
| WO | WO 2006/020638 | 2/2006 |
| WO | WO 2006/047534 | 5/2006 |
| WO | WO 2006/047698 | 5/2006 |
| WO | WO 2006/060380 | 6/2006 |
| WO | WO 2006/113377 | 10/2006 |
| WO | WO 2006/113411 | 10/2006 |
| WO | WO 2006/113474 | 10/2006 |
| WO | WO 2006/113563 | 10/2006 |
| WO | WO 2006/113563 A1 | 10/2006 |
| WO | WO 2006/113564 | 10/2006 |
| WO | WO 2006/113564 A2 | 10/2006 |
| WO | WO 2007/057734 | 5/2007 |
| WO | WO 2007/133384 | 11/2007 |
| WO | WO 2007/142981 | 12/2007 |
| WO | WO 2008/036671 | 3/2008 |
| WO | WO 2008/102096 | 8/2008 |
| WO | WO 2008/121649 | 10/2008 |
| WO | WO 2009/050511 | 4/2009 |
| WO | WO 2009/122409 | 10/2009 |
| WO | WO 2009/140080 | 11/2009 |
| WO | WO 2009/149060 | 12/2009 |
| WO | WO 2010/059214 | 5/2010 |
| WO | WO 2011/020074 | 2/2011 |
| WO | WO 2011/020078 | 2/2011 |
| WO | WO 2011/047076 | 4/2011 |
| WO | WO 2011/069059 | 6/2011 |
| WO | WO 2011/088107 | 7/2011 |
| WO | WO 2013/019871 | 2/2013 |
| WO | WO 2013/082545 | 6/2013 |
| WO | WO 2013/101793 | 7/2013 |
| WO | WO 2013/112589 | 8/2013 |
| WO | WO 2013/123265 | 8/2013 |
| WO | WO 2014/054946 | 4/2014 |
| WO | WO 2014/074610 | 5/2014 |
| WO | WO 2014/158653 | 10/2014 |
| WO | WO 2015/021323 | 2/2015 |
| WO | WO 2015/069927 | 5/2015 |
| WO | WO 2015/073718 | 5/2015 |

OTHER PUBLICATIONS

Aniridia Implants. (Aug. 24, 2011). Retrieved Feb. 5, 2015, from https://web.archive.org/web/20110824062840/http://www.morcher.com/nc/produkte/aniridiaimplants.html.
Accomodation and acuity under night-driving illumination levels. Arumi et al. Ophthal. Physiol. Opt. vol. 17, No. 4, pp. 291-299, 1997.
Accommodation and Presbyopia. Croft et al., International Opthalmology Clinics: Spring 2001, vol. 41, Issue 2, pp. 33-46.
Accomodation dynamics as a function of age. Heron et al. Ophthal. Physiol. Opt. 2002 22:389-396.
Accommodation Responses and Ageing. Heron et al. IOVS, Nov. 1999, vol. 40, No. 12, pp. 2872-2883.
Accommodative responses to anisoaccommodative targets. Koh et al. Ophthal. Physiol. Opt. vol. 18, No. 3, pp. 254-262, 1998.
Accommodation responses to flickering stimuli. Chauhan et al. Ophthal. Physiol. Opt. vol. 16. No. 5, pp. 391-408, 1996.
Accommodation to perceived depth in stereo tests. Koh et al. Ophthal. Physiol. Opt. vol. 18, No. 3, pp. 279-284, 1998.
Age Changes in the Interactions between the Accommodation and Vergence Systems. Heron et al. Optometry and Vision Science. vol. 78, No. 10, Oct. 2001.
Anterior Ciliary Sclerotomy for Treatment of Presbyopia: A Prospective Controlled Study. Hamilton et al. Ophthalmology, vol. 109, No. 11: Nov. 2002: pp. 1970-1977.
Barraquer, "Keratomileusis for Myopia and Aphakia", Ophthalmology, Rochester 88:701-708, 1981.
Bier, Prescribing for Presbyopia with Contact Lenses, The Opthalmic Optician, 5(9):439-455 (1965).
Binder et al., "Hydrogel keratophakia in non-human primates", Current Eye Research, vol. 1, No. 9, 1981/1982, pp. 535-542.
Brooks, J. et al., Identification of a vimentin-reactive Peptide associated with ocular lens membranes as cytokeratin, Ophthalmic Res., Jan.-Feb. 2003, pp. 8-11, vol. 35.
Cao et al, "Comparative study of the use of poly(glycolic acid), calcium alginate and pluronics in the engineering of autologous porcine cartilage", Polymers for Tissue Engineering, pp. 315-327, VSP 1998.
Can Accommodation be Surgically Restored in Human Presbyopia? Glasser, Adrian. Optometry and Vision Science, vol. 76, No. 9, Sep. 1999.
Changes in the static accommodation response with age. Kalsi et al. Ophthal. Physiol. Opt. vol. 21, No. 1, pp. 77-84, 2001.
Choice of Spatial Frequency for Contrast Sensitivity Evaluation After Corneal Refractive Surgery. Montes-Mico et al. Journal of Refractive Surgery, vol. 17: Nov./Dec. 2001: pp. 646-651.
Chow, C., et al., Broadband optical ultrasound sensor with a unique open-cavity structure, J. Biomed. Opt., Jan.-Feb. 2011, pp. 017001, vol. 16.
Choyce, P. "Implants with Coloured and Opaque Portions: Implants with Built-In Stenopeic Aperture," pp. 21-26 "Uniocular Aphakia Corrected by Anterior Chamber Implants with Built-In Stenopeic Aperture," pp. 132-136, 1964.
Clinical Characteristics of Lamellar Channel Deposits After Implementation of Intacs. Ruckhofer et al. J Cataract Refract Surg, vol. 26, Oct. 2000: pp. 1473-1479.
Contemporary Polymer Applications for Corneal Surgery. McCarey, Bernard E. pp. 504-505.
Cotliar et al., "Excimer Laser Radial Keratotomy", Ophthalmology, 1985.
Corneal Topography: The State of the Art, Alignment of Videokeratographs. Mandell et al. Chpt. 2, pp. 17-23, Jan. 1995.
"Corneal Surgery" by L. Girard, The C.V. Mosby Publishing Company, London 1981 pp. 107-141.
Dynamics of the accommodation response to abrupt changes in target vergence as a function of age. Heron et al. Vision Research 41 (2001) 507-519.
Dynamic retinoscopy and accomodation. Whitefoot et al. Ophthal. Physiol. Opt. vol. 12, Jan. 1992, pp. 8-17.
Eduard Jaeger's Test-Types (Schrift-Scalen) and Historical Development of Vision Tests. Runge, Paul E. Tr. Am. Ophth. Soc. vol. 98, 2000: 375.
Eight Years Experience with Permalens Intracorneal Lenses in Nonhuman Primates. Werblin et al. Refractive & Corneal Surgery, vol. 8, Jan./Feb. 1992, pp. 12-21.
"Epikeratophakia: Techniques, Compositions, and Clinical Results" by Werblin, Ophthalmology, 1983, pp. 45-58.
Errors in determining the direction of the visual axis in the presence of defocus. Atchison et al. Ophthal. Physiol. Opt., vol. 18, No. 5, pp. 463-467,1998.
Evaluate surgical routine to determine DLK cause, surgeon advises. Piechocki, Michael. Ocular Surgery News: Refractive Surgery, Jan. 1, 2003: p. 14.
Explanation for the observation of isogyres in crystalline lenses viewed between crossed polarizers. Ophthal. Physiol. Opt., vol. 13, Apr. 1993, pp. 209-211.
FDA Summary of Safety and Effectiveness Data for Tecnis Multifocal Posterior Chamber Intraocular Lens, Models ZM900 and ZMA00, 2009.
FDA Summary of Safety and Effectiveness Data for the Advanced Vision Science, Inc. XACT Foldable Hydrophopic Acrylic Ultraviolet Light-Absorbing Posterior Chamber Intraocular Lens (Model X-60 and Model X-70), 2009.

(56) References Cited

OTHER PUBLICATIONS

FDA Summary of Safety and Effectiveness Data for EC-3 IOL, (Models EC-3 IOL and EC-3 Precision Aspheric Lens), 2010.
FDA Summary of Safety and Effectiveness Data for Aaren Scientific's EC-3 IOL, 2010.
FDA Summary of Safety and Effectiveness Data for XACT Foldable Hydrophopic Acrylic UV Absorbing Posterior Chamber Intraocular Lens discussing clinical investigation beginning on May 8, 2002.
Flap Measurements With the Hansatome Microkeratome. Spadea et al. Journal of Refractive Surgery, vol. 18, Mar./Apr. 2002: pp. 149-154.
Focused and divided attention in stereoscopic depth. Wickens et al. SPIE, vol. 1256 Stereoscopic Displays and Applications (1990); pp. 28-34.
Gamez, G., et al., Development of a pulsed radio frequency glow discharge for three-dimensional elemental surface imaging. 1. Application to biopolymer analysis, Anal. Chem., Feb. 2007, pp. 1317-1326, vol. 79.
Glasier, M., et al., A solid-phase assay for the quantitation of total protein eluted from balafilcon, lotrafilcon, and etafilcon contact lenses, Current Eye Research, 2008, pp. 631-640, vol. 33.
Griffith et al.; "Functional Human Corneal Equivalents Constructed from Cell Lines", Science, vol. 286, Dec. 10, 1999 pp. 2169-2172.
Groppi, J. J. "New Aspects in the Fitting of the Multi-Range Bifocal Contact Lens" Contacto, vol. 15:22-29 1971.
Hara, T., et al., Accommodative intraocular lens with spring action. Part 1. Design and placement in an excised animal eye, Ophthalmic Surg., Feb. 1990, vol. 21.
Hara, T., et al., Ten-year results of anterior chamber fixation of the posterior chamber intraocular lens, Arch. Ophthalmol., Aug. 2004, pp. 1112-1116.
Hayasaka, S., et al., Scanning electron microscopic study of polyvinylidene fluoride degradation by ocular tissue extracts, Jpn. J. Ophthalmol., 1984, pp. 131-135, vol. 28.
Hayashi, K., et al., Intraocular lens factors that may affect anterior capsule contraction, Ophthalmology, Feb. 2005, pp. 286-292, vol. 112.
Hayashi, K., et al., Comparison of decentration and tilt between one piece and three piece polymethyl methacrylate intraocular lenses, Br. J. Ophthalmol., Apr. 1998, pp. 419-422, vol. 82.
Hidaka, T., et al, Adaptive optics instrumentation in submillimeter/terahertz spectroscopy with a flexible polyvinylidene fluoride cladding hollow waveguide, Rev. Sci. Instrum., 2007, pp. 25-26, vol. 78.
Hoffer et al., "UCLA Clinical Trial of Radial Keratotomy" Opthalmology, Aug. 1981; 88:729-736.
Holes in Clear Lenses Demonstrate a Pinhole Effect. Zacharia et al. Arch Ophthalmol, vol. 106, Apr. 1988, pp. 511-513.
Human Visual System—Image Formation, Encyclopedia of Imaging Science and Technology, Roorda, A., 2002, pp. 539-557.
Hybrid diffractive-refractive achromatic spectacle lenses. Charman, W. N. Ophthal. Physiol. Opt., vol. 14, Oct. 1994: pp. 389-392.
Iijima et al. "Formation of a spherical multicellular aggregate (spheroid) of animal cells in the pores of polyurethane foam as a cell culture substratum and its application to a hybrid artificial liver", Polymers for Tissue Engineering , pp. 273-286, Vsp 1998.
Imaging in the 21st century. Charman, W. N. Ophthal. Physiol. Opt., vol. 18, No. 2, pp. 210-223, 1998.
Intra-Ocular Lenses and Implants. Choyce, Peter. Chpts. 4 & 17, 1964.
Intraocular pressure after excimer laser myopic refractive surgery. Montes-Mico et al. Ophthal. Physiol. Opt., vol. 21, No. 3, pp. 228-235, 2001.
Intrastromal Crystalline Deposits Following Hydrogel Keratophakia in Monkeys. Parks et al. Cornea, 12(1): 29-34,1993.
Izak, A., et al., Loop memory of haptic materials in posterior chamber intraocular lenses, J. Cataract Refract. Surg., Jul. 2002, pp. 1129-1135, vol. 28.

"Katena Eye Instruments Catalog—Blaydes" dated Feb. 22, 2010, obtained from the Internet at: www.katena.com/html/product_detail.cfm in 1 page and printed on Feb. 22, 2010.
Kenyon. "Recurrent Corneal Erosion: Pathogenesis and Therapy," 1978, pp. 169-195.
"Keratomileusis and Keratophakia in the Surgical Correction of Aphakia" by Barraquer, Cataract Surgery and Special Techniques, prior to 1996 pp. 270-289.
Khodadoust et al., "Adhesion of Regenerating Corneal Epithelium," Am. J. of Opthalmology, Mar. 1968, pp. 339-348.
Kimura, W., et al., Comparison of shape recovery ratios in various IOL haptics, Nippon Ganka Gakkai Zasshi, Jun. 1991, pp. 548-555, vol. 95.
Kimura, W., et al., Comparison of shape recovery ratios in various intraocular lens haptics, J. Cataract. Refract. Surg., Nov. 1992, pp. 547-553, vol. 18.
Kimura, W., et al., Comparison of shape recovery ratios of single-piece poly(methyl methacrylate) intraocular lens haptics., J. Cataract. Refract. Surg., Sep. 1993, pp. 635-639, vol. 19.
Ko, A., et al., Seroreactivity against aqueous-soluble and detergent-soluble retinal proteins in posterior uveitis, Arch. Ophthalmol., Apr. 2011, pp. 415-420, vol. 129.
Kocak, N., et al., Intraocular lens haptic fracturing with the neodymium:YAG laser in vitro study, J. Cataract Refract. Surg., Apr. 2006, pp. 662-665, vol. 32.
"Lamellar Corneal Stromectomy for the Operative Treatment of Myopia" by Tadeusz Krwawicz, Notes, Cases, Instruments—1964, pp. 828-833.
Lipid Deposits Posterior to Impermeable Intracorneal Lenses in Rhesus Monkeys: Clinical, Histochemical, and Ultrastructural Studies. Rodrigues et al. Refractive & Corneal Surgery, vol. 6, Jan./Feb. 1990: DO. 32-37.
Lu Xuequan. Zhai Madlin, Li Jiuqiang, Ha Hongfei: "Radiation preparation and thermo-response swelling of interpenetrating polymer network hydrogel composed of PNIPAAm and PMMA" Radiation Physics and Chemistry, vol. 57, 2000, pp. 477-480, XP002473596.
Mastel Precision: Fiber Optic Ring Illuminator (Product Nos. 3776 & 4050) U.S. Pat. No. 5,312,393, User Manual. Rev: A02: Jan. 11, 1995, pp. 1-25.
Mastel Precision: The Ring Light. http://www.mastel.com/ring_light.html. Jul. 28, 2003.
Measurement of the wave-front aberration of the eye by a fast psychophysical procedure. He et al. J. Opt. Soc. Am. A, vol. 15, No. 9: Sep. 1998, pp. 2449-2455.
Microstructural Changes in Polyester Biotextiles During Implantation in Humans. King et al. NC State University: JTATM, vol. 1, Issue 3, Spring 2001, pp. 1-8.
Miller et al. "Quantification of the Pinhole effect" Perspectives in Refraction, vol. 21:347-350 1977.
Moran, C., et al. Polyvinylidene flouride polymer applied in an intraocular pressure sensor, Jpn. J. Appl. Phys., 2005, pp. L885-L887, vol. 44, Issue 27.
Near vision, lags of accommodation and myopia. Charman, W. N. Ophthal. Physiol. Opt., vol. 19, No. 2, pp. 126-133, 1999.
New Visual Acuity Charts for Clinical Research. Ferris et al. American Journal of Ophthalmology, 94: 91-96, 1982.
Night myopia and driving. Charman, W. N. Ophthal. Physiol. Opt., vol. 16, No. 6, p. 474-485, 1996.
Notch in contrast sensitivity function of optical origin: diffraction effects of acrylic filters. Irving et al., Ophthal. Physiol. Opt., vol. 13, Apr. 1993: pp. 179-182.
On modeling the causes of presbyopia. Glasser, A. Vision Research 41(2001) 3083-3087.
On the linearity of accommodation dynamics. Charman, W. N. Vision Research 40 (2000) 2057-2066.
Optical Aspects of Tolerances to Uncorrected Ocular Astigmatism. Charman et al. Optometry and Vision Science, vol. 70, No. 2: pp. 111-117, 1993.
Optical Modeling of Contact Lens Performance Final Report Covering Period Jul. 15, 1994-Mar. 31, 1995. Grivenkamp et al. for Pilkington Barnes Hind, Issued Apr. 5, 1995.

(56) References Cited

OTHER PUBLICATIONS

Optometric Clinical Practice Guideline Care of the Patient With Presbyopia: Reference Guide for Clinicians. Mancil et al. Mar. 20, 1998.
Ozanics et al., "Prenatal Development of the Eye and its Adnexa," Biomedical Foundation of Opthalmology, 1985, vol. 1, Chap 2, pp. 7-15.
Patel, C.K., et al. "Imaging the macula through a black occlusive intraocular lens". Arch. Ophthalmol. Oct. 2010; 128(10):1374-1376.
PermaVision intracorneal lens shows promise for hyperopia. Kronemyer, Bob. Ocular Surgery News: Jan. 1, 2003; p. 8.
Perspectives in Refraction: Quantification of the Pinhole Effect. Miller et al. Survey of Ophthalmology, vol. 21, No. 4, Jan./Feb. 1977, pp. 347-350.
Peyman et al., "Modification of Rabbit Corneal Curvature with use of Carbon Dioxide Laser Burns," Ophth, Surg., vol. 11, No. 5, 5/80, pp. 325-329.
Puliafito, C., et al., "Excimer Laser Ablator of the Cornea & Lens," Opthalmology, 6/85 vol. 92 No. 6, pp. 741-748.
Sally Pobojewski, "New U-developed laser performs high-precision corneal surgery", News and Information Services, The University Record, Jul. 16, 1997.
Poly(methyl methacrylate) model study of optical surface quality after excimer laser photo refractive keratectomy. Hauge et al. J Cataract Refract Surg., vol. 27, Dec. 2001, pp. 2026-2035.
Prince, S., et al., Sorption of alkylbenzyldimethylammonium chloride homologs to various filter media used in processing ophthalmics, APhA Annual Meeting, 1996, pp. 103, vol. 143.
Procyon: Marketing Information for Distributors: Pupil Measurement and Refractive Sugery (Samples from Academic Papers 1994 and 2002). pp. 1-17.
"Refractive Keratoplasty: Acute Morphologic Features," by Baumgarter et al, The CLAO Journal—Apr. 1985, vol. II, No. 2, pp. 163-169.
Refractive keratoplasty with intrastromal hydrogel lenticular implants. McCarey et al. Invest., Ophthalmol. Vis. ScL, Jul. 1981, pp. 107-115.
Retinal Image Quality in the Human Eye as a Function of the Accommodation. Lopex-Gil et al. Vision Research, vol. 38, No. 19, Jul. 3, 1998, pp. 1-11.
Rosenbloom "The Controlled-Pupil Contact Lens in Low Vision Problems" Journal of the American Optometric Association, pp. 836, 838, 840 1969.
Sato, "A New Surgical Approach to Myopia", Am. J. Ophthalmol. 36:823, 1953.
Shingleton, B., Reply: pupil stretch technique, J. Cataract Refract. Surg., 2007, pp. 362, vol. 33.
Simple parametric model of the human ocular modulation transfer function, A. Deeley et al. Ophthal. Physiol. Opt., vol. 11, Jan. 1991, pp. 91-93.
Karin R. Slettin, MD et al., "An In Vivo Model of Femtosecond Laser Intrastromal Refractive Surgery", Experimental Science, Ophthalmic Surgery and Lasers, Nov./Dec. 1999, vol. 30, No. 9, pp. 742-749.
Subjective Depth-of-Focus of the Eye. Atchison et al. Optometry and Vision Science, vol. 74, No. 7, Jul. 1997, pp. 511-520.
Subjective Sensitivity to Small Changes in the Contrast of a Suprathreshold Grating, The. Walsh et al. Vision Res., vol. 30, No. 1, pp. 163-193, 1990.
Surface Modification Properties of Parylene for Medical Applications, The. Wolgemuth, Lonny.Business Briefing: Medical Device Manfacturing & Technology 2002, pp. 1-4.
Surface tension control of collagen biomaterials by the selective hydrolysis of internal carboxyamides of the protein matrix. Revista Brasileira de Engenharia Biomedica, vol. 15, No. 1-2, p. 55-61, Jan./ago 1999.
Surgeon: Severe corneal lesions after LASIK are not stage 4 DLK. Piechocki, Michael. Ocular SurgeryNews; Jan. 1, 2003, pp. 16-17.
Subrayan, V., et al., Improving quality of vision with an anterior surface modified prolate intraocular lens: A prosepective clinical trial, Int. J. Ophthalmol., Aug. 2007, pp. 918-920, vol. 7, No. 4.
Swinger et al., "Keratophakia and Keratomileusis-Clinical Results", American Academy of Ophthalmology, Aug. 1981, vol. 88, No. 8, pp. 709-715.
Taboda, J., et al., "Response of the Corneal Epithelium to K.F. Excimer Laser Pulses," Health Physics, 1981, vol. 40, pp. 677-683.
Takahashi, E. "Use and Interpretation of the Pinhole Test" The Optometric Weekly, pp. 83-86 1965.
Tasaki, I., et al., Demonstration of heat production associated with spreading depression in the amphibian retina, Biochem. Biophys. Res. Commun., 1991, pp. 293-297, vol. 174.
Theoretical and practical performance of a concentric bifocal intraocular implant lens. Charman, W.N. Vision Research 38 (1998) 2841-2853.
Trokel, S., et al., "Excimer Laser Surgery of the Cornea," Am. J. Opthalmology, 1983 vol. 96, pp. 710-715.
Use of a digital infrared pupillometer to assess patient suitability for refractive surgery. Rosen et al. J Cataract Refract Surg., vol. 28: Aug. 2002. pp. 1433-1438.
Vision and driving—a literature review and commentary. Charman, W.N. Ophthal. Physiol. Opt., vol. 17, No. 5, pp. 371-391, 1997.
Wesley, A New Concept in Successful Bifocal Contact Lens Fitting, pp. 71-73.
Wesley, N. K. "Research on the Multi-Range Lens," pp. 18-24, 1970.
Yamauchi et al., "Cultivation of fibroblast cells on keratin coated substrata", Polymers for Tissue Engineering, pp. 329-340, VS 1998.
Yusuf, et al., "Inability to perform posterior segment monitoring by scanning laser ophthalmoscopy or optical coherence tomography with some occlusive intraocular lenses in clinical use", J. Cataract Refract. Surg., Mar. 2012, 38: 513-513.
Yusuf, et al., "Occlusive IOLs for Intractable Diplopia Demonstrate a Novel Near-Infrared Window of Transmission for SLO/OCT Imaging and Clinical Assessment". Investigative Ophthalmology & Visual Science, May 2011, 52(6): 3737-3743.
Zavala et al., "Refractive Keratoplosty: Lathing and Cyropreservation," CLAO Journal, Apr. 1985, 11:155-162.

\* cited by examiner

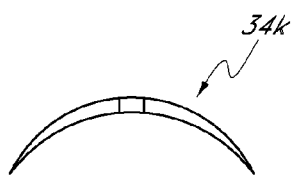
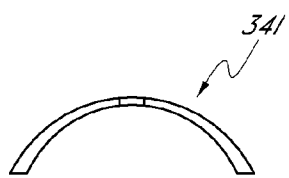
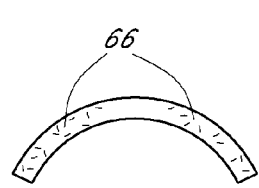
FIG. 17  FIG. 18  FIG. 19
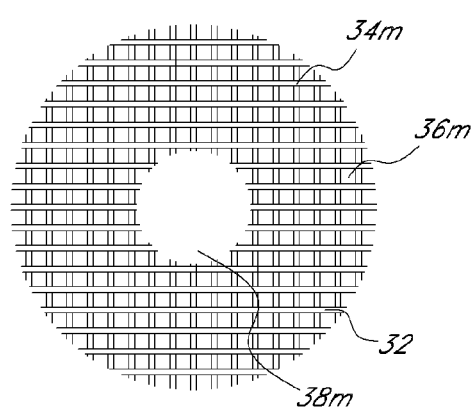
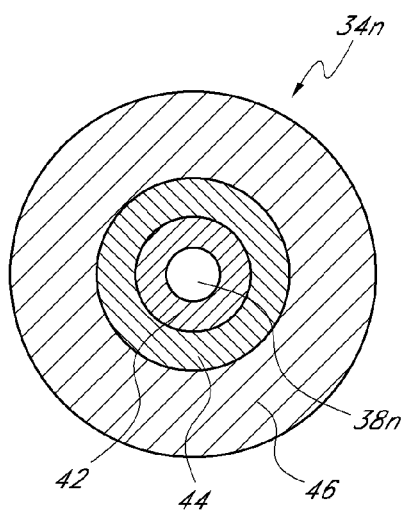
FIG. 20  FIG. 22
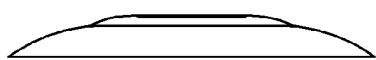
FIG. 21  FIG. 23

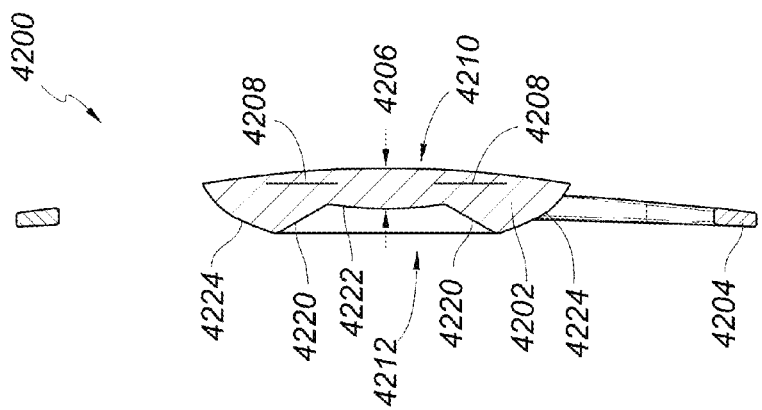
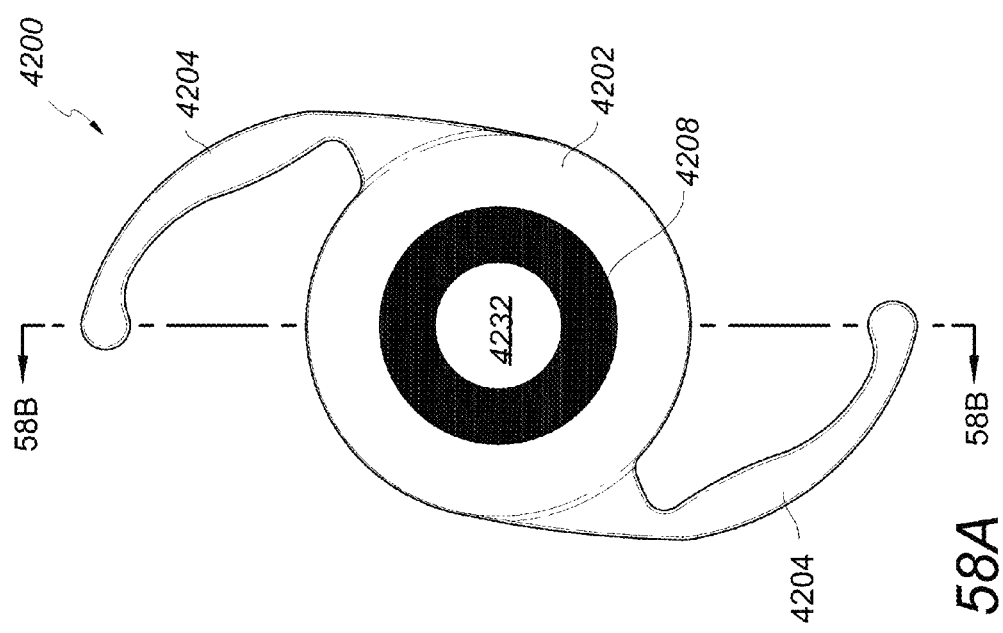
FIG. 58B
FIG. 58A

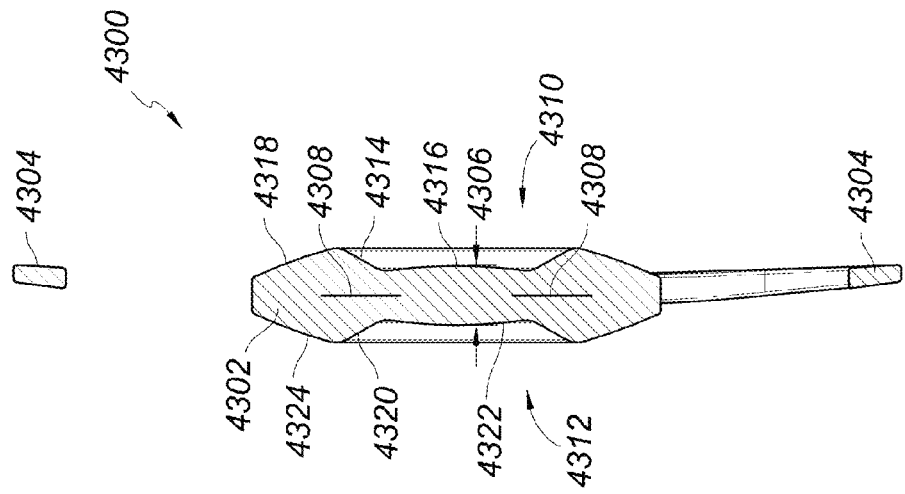
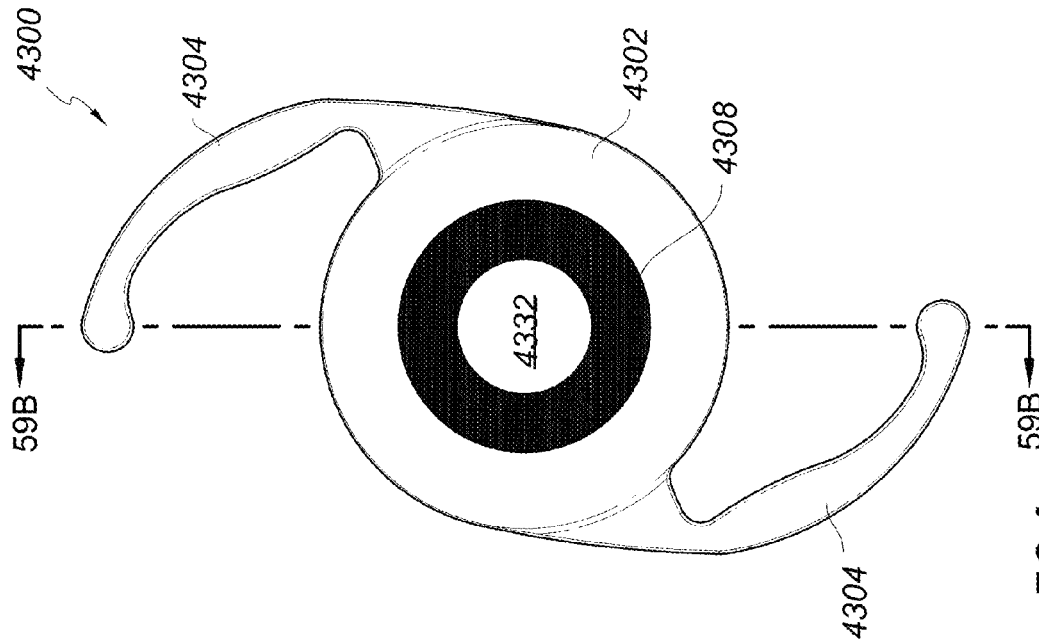
FIG. 59B
FIG. 59A

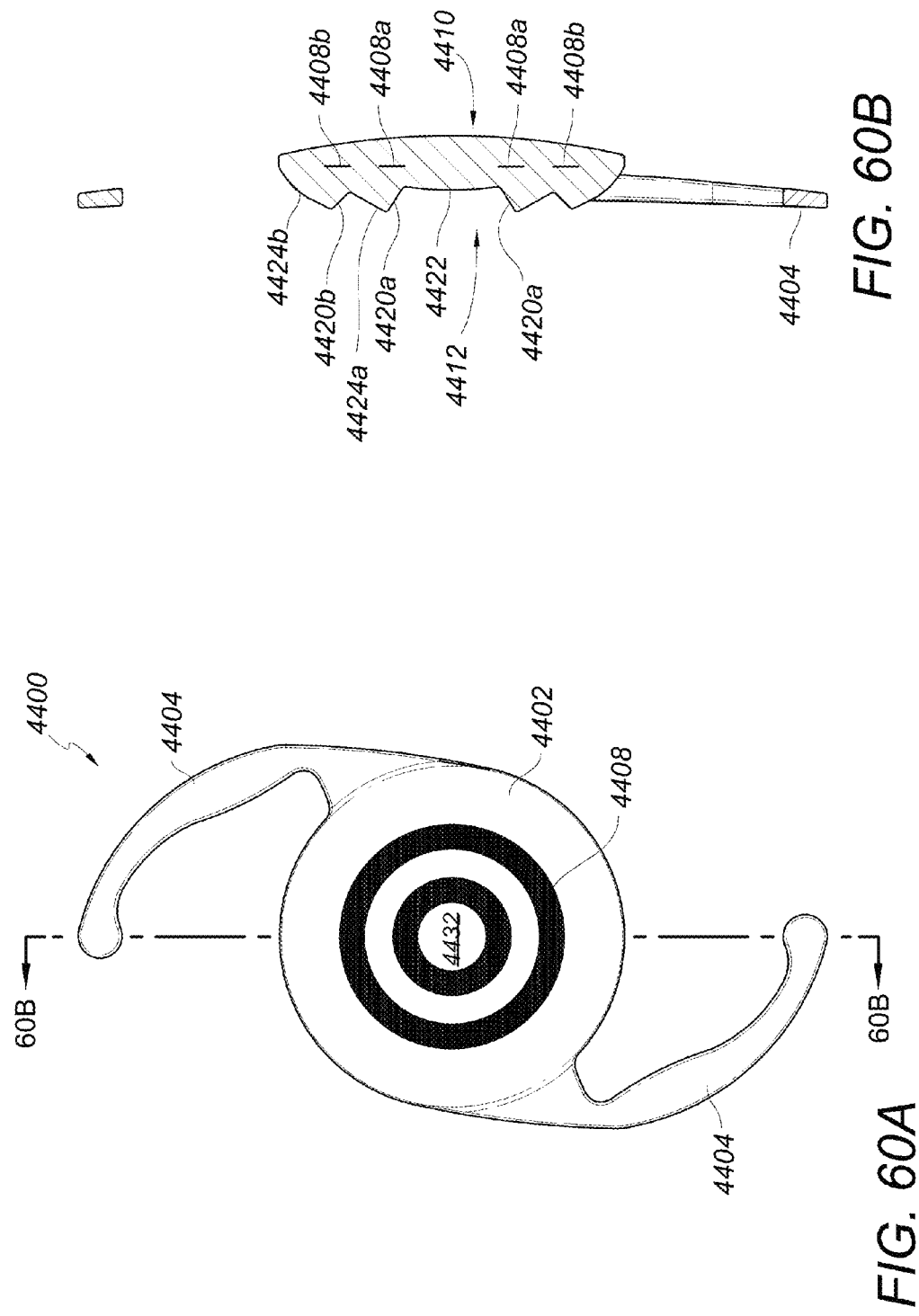

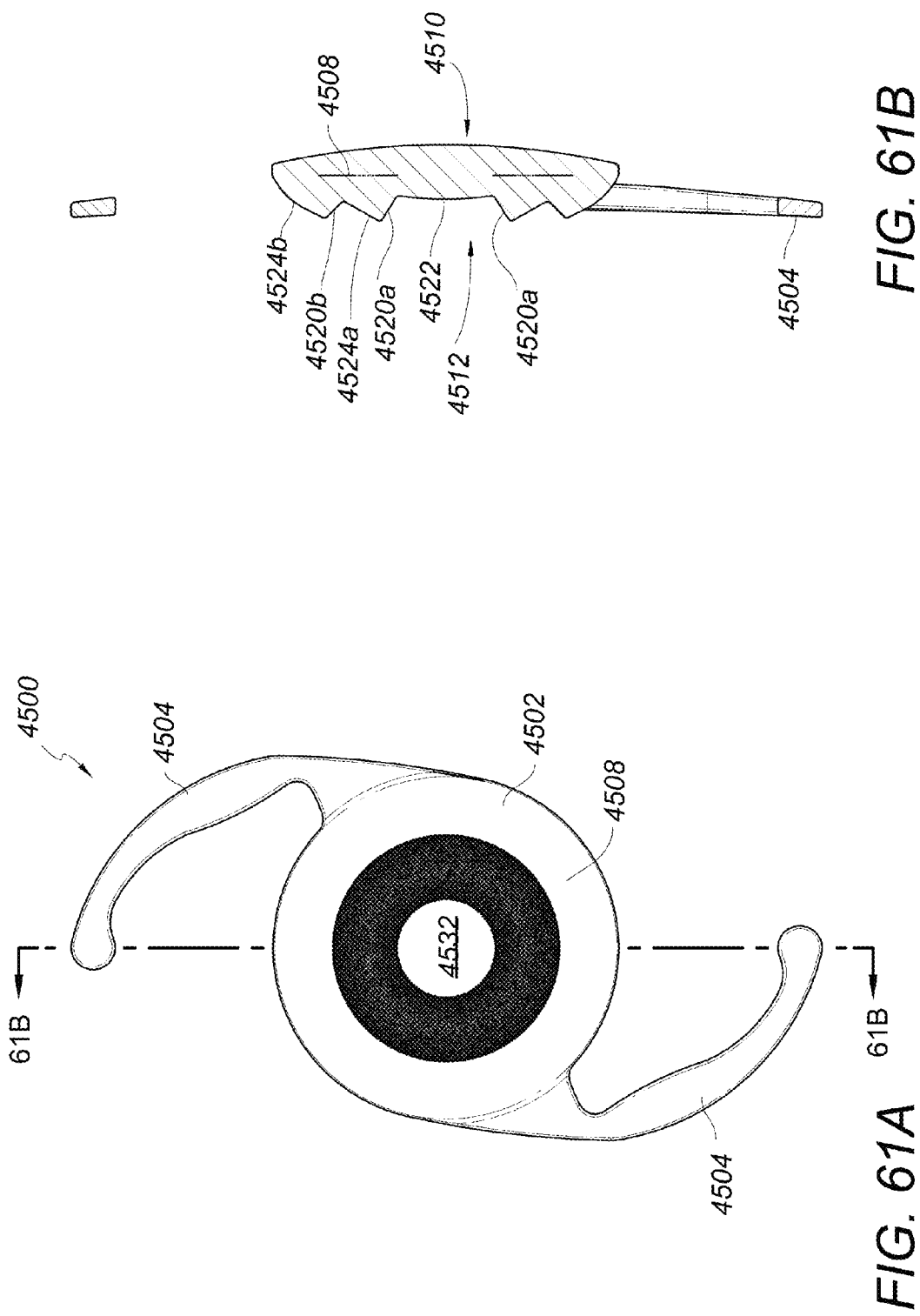

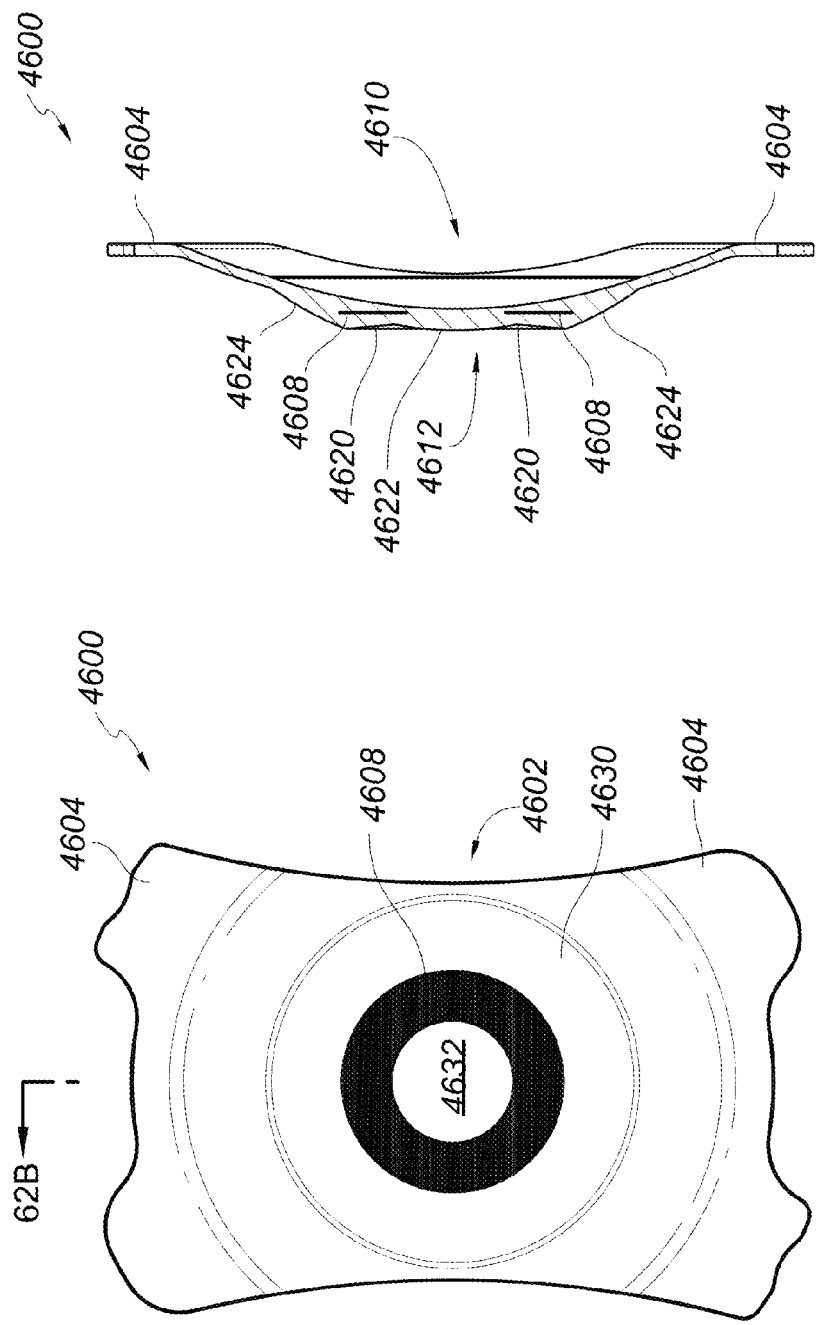

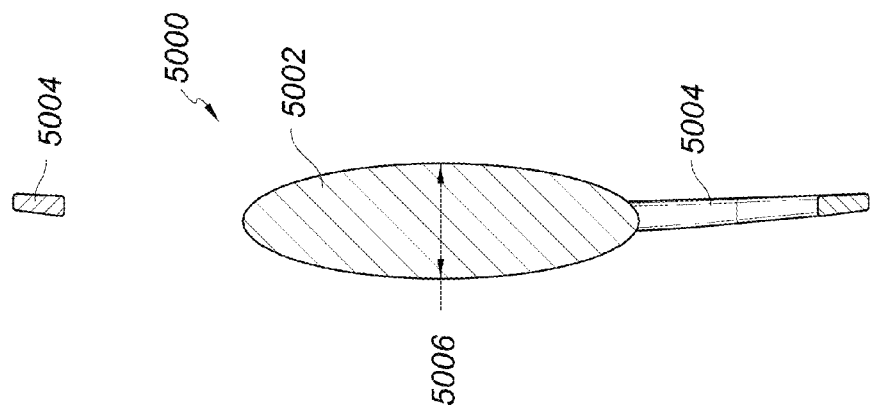
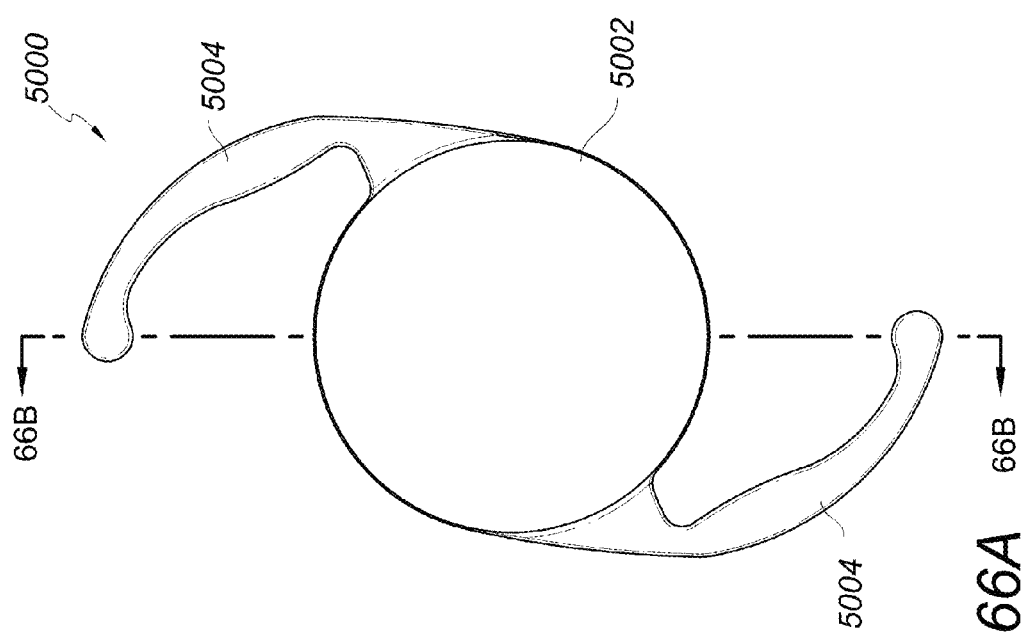

US 9,545,303 B2

OCULAR MASK HAVING SELECTIVE SPECTRAL TRANSMISSION

CROSS-REFERENCE TO RELATED APPLICATIONS

This application claims priority benefit of U.S. Provisional Application Ser. No. 61/566,523, filed Dec. 2, 2011, the entire contents of which are hereby incorporated by reference.

BACKGROUND

Field

This application relates generally to the field of ocular devices. For example, this application is directed to ocular devices with an aperture to improve depth of focus (e.g. "masked" corneal inlays) and methods of making.

Description of the Related Art

The human eye functions to provide vision by transmitting and focusing light through a clear outer portion called the cornea, and further refining the focus of the image by way of a crystalline lens onto a retina. The quality of the focused image depends on many factors including the size and shape of the eye, and the transparency of the cornea and the lens.

The optical power of the eye is determined by the optical power of the cornea and the crystalline lens. In a normal, healthy eye, sharp images of distant objects are formed on the retina (emmetropia). In many eyes, images of distant objects are either formed in front of the retina because the eye is abnormally long or the cornea is abnormally steep (myopia), or formed in back of the retina because the eye is abnormally short or the cornea is abnormally flat (hyperopia). The cornea also may be asymmetric or toric, resulting in an uncompensated cylindrical refractive error referred to as corneal astigmatism.

A normally functioning human eye is capable of selectively focusing on either near or far objects through a process known as accommodation. Accommodation is achieved by inducing deformation in the natural crystalline lens located inside the eye. Such deformation is induced by muscles called ciliary muscles. In most individuals, the ability to accommodate diminishes with age and these individuals cannot see up close without vision correction. If far vision also is deficient, such individuals are usually prescribed bifocal lenses.

SUMMARY

A first aspect of this application is directed toward an ophthalmic device comprising
a mask configured to increase the depth of focus of a patient. The mask comprising an aperture configured to transmit along an optical axis substantially all visible incident light. The mask further comprising a structure surrounding the aperture. The structure configured to be substantially opaque to visible light and to be substantially transparent to at least some non-visible electromagnetic radiation with a wavelength between about 750 nm and about 1500 nm.

Another aspect of this application is directed toward an ophthalmic device configured to increase the depth of focus of a patient. The ophthalmic device includes a first zone configured to transmit along an optical axis a majority of visible incident light, and a mask disposed about the first zone and being configured to be substantially opaque to visible light and to be substantially transparent to at least some electromagnetic radiation outside of the visible spectrum.

In any of the aspects of the ophthalmic device, the mask is substantially transparent to at least some electromagnetic radiation in the near infrared spectrum.

In any of the aspects of the ophthalmic device, the ophthalmic device includes a plurality of holes in the structure. The plurality of holes are interspersed in an irregular pattern and configured to permit a bond to form between lens body portions on either side of the mask.

In any of the above mentioned aspects of the ophthalmic device, each of the plurality of holes has a diameter between about 0.01 mm and 0.02 mm.

In any of the above mentioned aspects of the ophthalmic device, the structure includes at least one dye capable of absorbing electromagnetic radiation.

In any of the above mentioned aspects of the ophthalmic device, the at least one dye includes a first dye and a second dye. The first dye absorbs a first range of electromagnetic radiation wavelengths, and the second dye absorbs a second range of electromagnetic radiation wavelengths.

In any of the above mentioned aspects of the ophthalmic device, the first range of electromagnetic radiation wavelengths and the second range of electromagnetic radiation wavelengths include substantially all the range of visible electromagnetic radiation thereby absorbing substantially all the range of visible electromagnetic radiation. The first range of electromagnetic radiation wavelengths and the second range of electromagnetic radiation wavelengths do not include a substantial range of the near infrared range of electromagnetic radiation thereby allowing transmission of substantially all the range of near infrared electromagnetic radiation.

In any of the above mentioned aspects of the ophthalmic device, the at least one dye includes a third dye. The third dye absorbs a third range of electromagnetic radiation wavelengths.

In any of the above mentioned aspects of the ophthalmic device, the first range of electromagnetic radiation wavelengths, the second range of electromagnetic radiation wavelengths, and the third range of electromagnetic radiation wavelengths include substantially all the range of visible electromagnetic radiation thereby absorbing substantially all the range of visible electromagnetic radiation. The first range of electromagnetic radiation wavelengths, the second range of electromagnetic radiation wavelengths, and the third range of electromagnetic radiation wavelengths do not include a substantial range of the near infrared range of electromagnetic radiation thereby allowing transmission of substantially all the range of near infrared electromagnetic radiation.

In any of the above mentioned aspects of the ophthalmic device, the first dye is an orange dye and wherein the second dye is a blue-green dye.

In any of the above mentioned aspects of the ophthalmic device, the first dye is an orange dye, the second dye is a blue-green dye, and the third dye is a yellow dye.

In any of the above mentioned aspects of the ophthalmic device, the orange dye is 2-[N-ethyl-4-[(4-nitrophenyl)diazenyl]anilino]ethyl prop-2-enoate.

In any of the above mentioned aspects of the ophthalmic device, the blue-green dye is 2-[4-({4-[(4-{2-[(2-methyl-prop-2-enoyl)oxy]ethyl}phenyl)amino]-9,10-dioxo-9,10-dihydro-anthracen-1-yl}amino)phenyl]ethyl-2-methyl prop-2-enoate.

In any of the above mentioned aspects of the ophthalmic device, the ophthalmic device includes a UV blocker. The UV blocker blocks at least some of the UV range of electromagnetic radiation.

In any of the above mentioned aspects of the ophthalmic device, the UV blocker is a benzotriazole UV blocker.

In any of the above mentioned aspects of the ophthalmic device, the UV blocker is ([2-(5-Chloro-2H-Benzotriazole-2-yl)-6-(1,1-dimethylethyl)-4-ethenylphenol.

In any of the above mentioned aspects of the ophthalmic device, the ophthalmic device includes a UV blocker. The UV blocker is ([2-(5-Chloro-2H-Benzotriazole-2-yl)-6-(1,1-dimethylethyl)-4-ethenylphenol. The at least one dye includes 2-[N-ethyl-4-[(4-nitrophenyl)diazenyl]anilino] ethyl prop-2-enoate and 2-[4-({4-[(4-{2-[(2-methylprop-2-enoyl)oxy]ethyl}phenyl)amino]-9,10-dioxo-9,10-dihydro-anthracen-1-yl}amino)phenyl]ethyl-2-methyl prop-2-enoate.

Another aspect of this application is directed toward a method of examining an eye of a patient having a pinhole imaging device disposed therein. The method includes aligning a source of electromagnetic radiation with a portion of the pinhole imaging device that is substantially non-transmissive to light in the visible range and transmitting electromagnetic radiation with a wavelength between about 750 nm and about 1500 nm through the substantially non-transmissive portion.

In any of the above mentioned aspect of the method of examining an eye, the method includes providing an optical coherence tomography device having a patient interface and engaging the patient with the patient interface.

In any of the above mentioned aspect of the method of examining an eye, the method includes transmitting electromagnetic radiation with a wavelength between about 750 nm and about 1500 nm through the aperture of the pinhole imaging device.

In any of the above mentioned aspect of the method of examining an eye, the method includes the electromagnetic radiation is simultaneously transmitted through the aperture and the substantially non-transmissive portion of the pinhole imaging device.

BRIEF DESCRIPTION OF THE DRAWINGS

FIG. 17 is a side view of an embodiment of a mask having varying thickness.

FIG. 18 is a side view of another embodiment of a mask having varying thickness.

FIG. 19 is a side view of an embodiment of a mask with a gel to provide opacity to the lens.

FIG. 20 is a frontal plan view of an embodiment of a mask with a weave of polymeric fibers.

FIG. 21 is a side view of the mask of FIG. 20.

FIG. 22 is a frontal plan view of an embodiment of a mask having regions of varying opacity.

FIG. 23 is a side view of the mask of FIG. 22.

FIG. 58A illustrates a front plan view of an embodiment of an intraocular lens with a recessed central region on the anterior surface as described herein.

FIG. 58B illustrates a cross-sectional view of the intraocular lens of FIG. 58A.

FIG. 59A illustrates a front plan view of an embodiment of an intraocular lens with a recessed central region on the posterior surface and anterior surface as described herein.

FIG. 59B illustrates a cross-sectional view of the intraocular lens of FIG. 59A.

FIG. 60A illustrates a front plan view of an embodiment of an intraocular lens with two transition zones and two masks as described herein.

FIG. 60B illustrates a cross-sectional view of the intraocular lens of FIG. 60A.

FIG. 61A illustrates a front plan view of an embodiment of an intraocular lens with two transition zones and a single mask as described herein.

FIG. 61B illustrates a cross-sectional view of the intraocular lens of FIG. 61A.

FIG. 62A illustrates a front plan view of an embodiment of an intraocular lens with a concave posterior surface and a positive optical power as described herein.

FIG. 62B illustrates a cross-sectional view of the intraocular lens of FIG. 62A.

FIG. 66A illustrates a top view of a conventional intraocular lens.

FIG. 66B illustrates a cross-sectional view of the conventional intraocular lens of FIG. 66A.

DETAILED DESCRIPTION

This application is directed to ocular devices and implants (e.g., masks) for improving the depth of focus of an eye of a patient and methods and apparatuses for making such ocular devices. The masks generally employ small-aperture vision correction methods to enhance depth of focus in a presbyopic eye thereby providing functional near vision. The masks may be applied to the eye in any manner and in any location, e.g., as an implant in the cornea (sometimes referred to as a "corneal inlay"). The masks can also be embodied in or combined with lenses and applied in other regions of the eye, e.g., as or in combination with contact lenses or intraocular lenses (IOL).

The ocular devices and masks described herein can be applied to masks and/or combined with features described in U.S. Patent Publication No. 2006/0265058, filed Apr. 13, 2006, entitled "CORNEAL MASK FORMED OF DEGRADATION RESISTANT POLYMER AND PROVIDING REDUCED CORNEAL DEPOSITS," U.S. Patent Publication No. 2011/0040376, filed Aug. 13, 2010, entitled "MASKED INTRAOCULAR IMPLANTS AND LENSES," and International Patent Publication No. WO 2011/020074, filed Aug. 13, 2010, entitled "CORNEAL INLAY WITH NUTRIENT TRANSPORT STRUCTURES," the entirety of each of which is hereby incorporated by reference.

Overview of Depth of Focus Vision Correction

Presbyopia is a problem of the human eye that commonly occurs in older human adults wherein the ability to focus becomes limited to inadequate range. FIGS. 1-6 illustrate how presbyopia interferes with the normal function of the eye and how a mask with a pinhole aperture mitigates the problem. A mask that has a pinhole aperture may be used to improve the depth of focus of a human eye.

Figure 1:
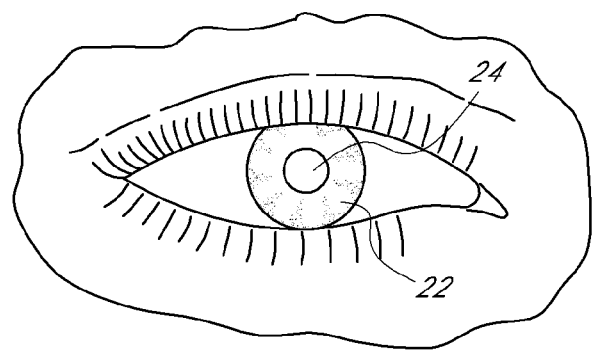
FIG. 1 is a plan view of the human eye.
Figure 2:
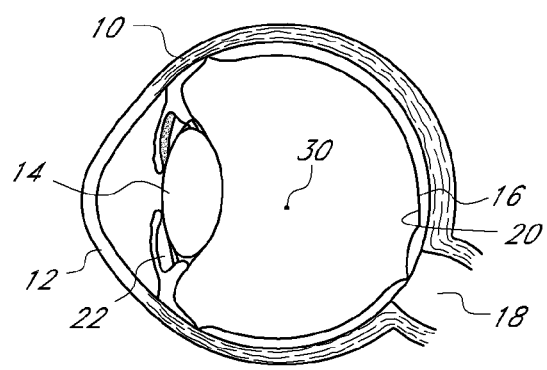
FIG. 2 is a cross-sectional side view of the human eye.

FIG. 1 shows the human eye, and FIG. 2 is a side view of the eye 10. The eye 10 includes a cornea 12 and an intraocular lens 14 posterior to the cornea 12. The cornea 12 is a first focusing element of the eye 10. The intraocular lens 14 is a second focusing element of the eye 10. The eye 10 also includes a retina 16, which lines the interior of the rear surface of the eye 10. The retina 16 includes the receptor cells which are primarily responsible for the sense of vision. The retina 16 includes a highly sensitive region, known as the macula, where signals are received and transmitted to the visual centers of the brain via the optic nerve 18. The retina 16 also includes a point with particularly high sensitivity 20, known as the fovea. As discussed in more detail in connection with FIG. 8, the fovea 20 is slightly offset from the axis of symmetry of the eye 10.

The eye 10 also includes a ring of pigmented tissue known as the iris 22. The iris 22 includes smooth muscle for controlling and regulating the size of an opening 24 in the iris 22, which is known as the pupil. An entrance pupil 26 is seen as the image of the iris 22 viewed through the cornea 12 (See FIG. 4).

The eye 10 resides in an eye-socket in the skull and is able to rotate therein about a center of rotation 30.

Figure 3:
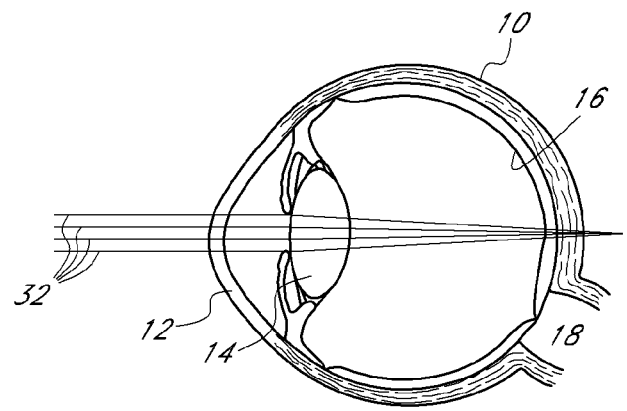
FIG. 3 is a cross-sectional side view of the human eye of a presbyopic patient wherein the light rays converge at a point behind the retina of the eye.

FIG. 3 shows the transmission of light through the eye 10 of a presbyopic patient. Due to either an aberration in the cornea 12 or the intraocular lens 14, or loss of muscle control, light rays 32 entering the eye 10 and passing through the cornea 12 and the intraocular lens 14 are refracted in such a way that the light rays 32 do not converge at a single focal point on the retina 16. FIG. 3 illustrates that in a presbyopic patient, the light rays 32 often converge at a point behind the retina 16. As a result, the patient experiences blurred vision.

Figure 4:
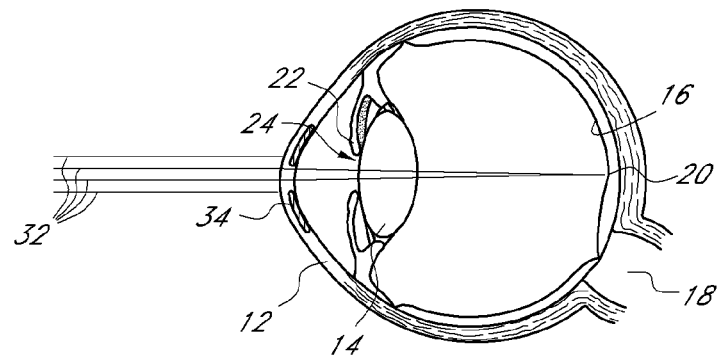
FIG. 4 is a cross-sectional side view of a presbyopic eye implanted with one embodiment of a mask wherein the light rays converge at a point on the retina.

Turning now to FIG. 4, there is shown the light transmission through the eye 10 to which a mask 34 has been applied. The mask 34 is shown implanted in the cornea 12 in FIG. 4. However, as discussed below, it will be understood that the mask 34 can be, in various modes of application, implanted in the cornea 12 (as shown), used as a contact lens placed over the cornea 12, incorporated in the intraocular lens 14 (including the patient's original lens or an implanted lens), or otherwise positioned on or in the eye 10. In the illustrated embodiment, the light rays 32 that pass through the mask 34, the cornea 12, and the lens 14 converge at a single focal point on the retina 16. The light rays 32 that would not converge at the single point on retina 16 are blocked by the mask 34. As discussed below, it is desirable to position the mask 34 on the eye 10 so that the light rays 32 that pass through the mask 34 converge at the fovea 20.

Figure 6:
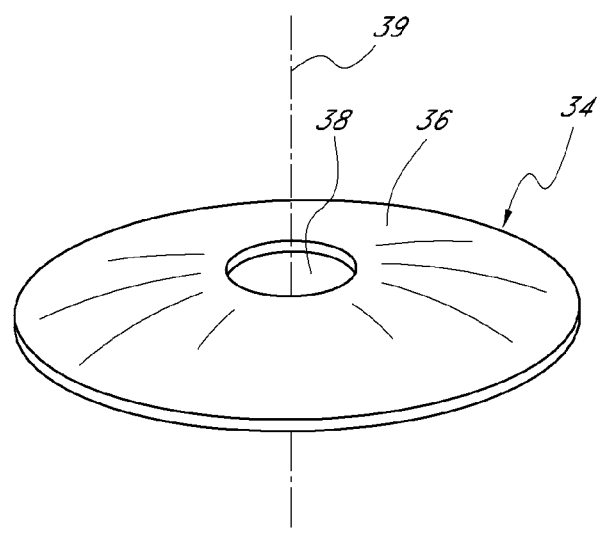
FIG. 6 is a perspective view of one embodiment of a mask.

Turning now to FIG. 6, there is shown one embodiment of the mask 34. A variety of variations of the mask 34 are discussed hereinbelow. As seen, the mask 34 preferably includes an annular region 36 surrounding a pinhole opening or aperture 38 substantially centrally located on the mask 34. The pinhole aperture 38 is generally located around a central axis 39, referred to herein as the optical axis of the mask 34. The pinhole aperture 38 preferably is in the shape of a circle. It has been reported that a circular aperture, such as the aperture 38 may, in some patients, produce a so-called "halo effect" where the patient perceives a shimmering image around the object being viewed. Accordingly, it may be desirable to provide an aperture 38 in a shape that diminishes, reduces, or completely eliminates the so-called "halo effect."

Ophthalmic Devices Employing Depth of Focus Correction

Figures 7, 8, 9:
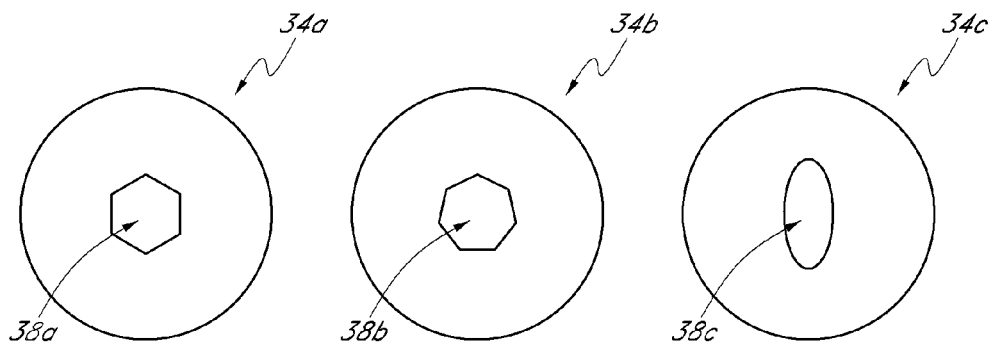
FIG. 7 is a frontal plan view of an embodiment of a mask with a hexagon-shaped pinhole like aperture.
FIG. 8 is a frontal plan view of an embodiment of a mask with an octagon-shaped pinhole like aperture.
FIG. 9 is a frontal plan view of an embodiment of a mask with an oval-shaped pinhole like aperture.
Figures 10, 11, 12:
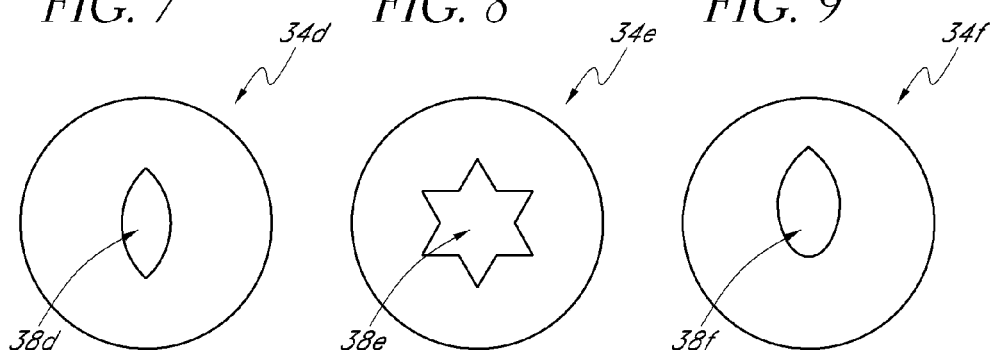
FIG. 10 is a frontal plan view of an embodiment of a mask with a pointed oval-shaped pinhole like aperture.
FIG. 11 is a frontal plan view of an embodiment of a mask with a star-shaped pinhole like aperture.
FIG. 12 is a frontal plan view of an embodiment of a mask with a teardrop-shaped pinhole like aperture spaced above the true center of the mask.

FIGS. 7-42 illustrate a variety of embodiments of masks that can improve the vision of a patient with presbyopia. The masks described in connection with FIG. 7-42 are similar to the mask 34, except as described differently below. Any of the masks discussed below, e.g., those shown in FIGS. 7-42, can be made of any of the materials discussed herein. The mask 34 and any of the masks discussed below can include a locator structure, such as is discussed in U.S. Patent Publication No. 2006/0235428, filed Apr. 14, 2005 with the title "OCULAR INLAY WITH LOCATOR," which is incorporated herein by reference in its entirety. The masks described in connection with FIGS. 7-42 can be used and applied to the eye 10 of a patient in a similar fashion to the mask 34. For example, FIG. 7 shows an embodiment of a mask 34a that includes an aperture 38a formed in the shape of a hexagon. FIG. 8 shows another embodiment of a mask 34b that includes an aperture 38b formed in the shape of an octagon. FIG. 9 shows another embodiment of a mask 34c that includes an aperture 38c formed in the shape of an oval, while FIG. 10 shows another embodiment of a mask 34d that includes an aperture 38d formed in the shape of a pointed oval. FIG. 11 shows another embodiment of a mask 34e wherein the aperture 38e is formed in the shape of a star or starburst.

Figures 13, 14, 15:
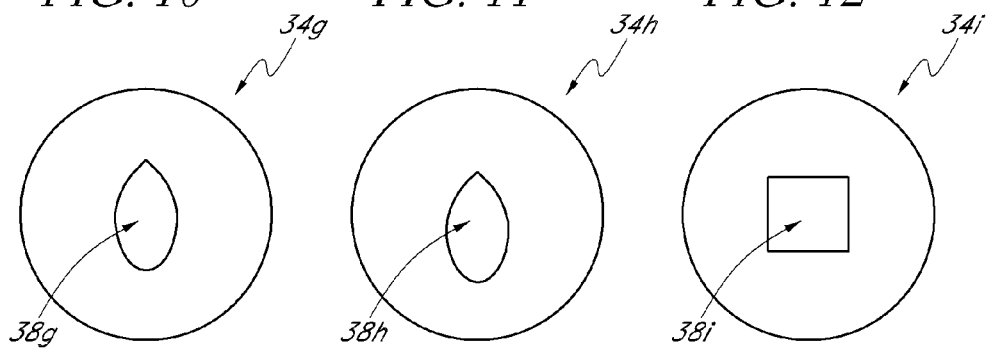
FIG. 13 is a frontal plan view of an embodiment of a mask with a teardrop-shaped pinhole like aperture centered within the mask.
FIG. 14 is a frontal plan view of an embodiment of a mask with a teardrop-shaped pinhole like aperture spaced below the true center of the mask.
FIG. 15 is a frontal plan view of an embodiment of a mask with a square-shaped pinhole like aperture.

FIGS. 12-14 illustrate further embodiments that have tear-drop shaped apertures. FIG. 12 shows a mask 34f that has a tear-drop shaped aperture 38f that is located above the true center of the mask 34f. FIG. 13 shows a mask 34g that has a tear-drop shaped aperture 38g that is substantially centered in the mask 34g. FIG. 14 shows a mask 34h that has a tear-drop shaped aperture 38h that is below the true center of the mask 34h. FIG. 12-14 illustrate that the position of aperture can be tailored, e.g., centered or off-center, to provide different effects. For example, an aperture that is located below the true center of a mask generally will allow more light to enter the eye because the upper portion of the aperture 34 will not be covered by the eyelid of the patient. Conversely, where the aperture is located above the true center of the mask, the aperture may be partially covered by the eyelid. Thus, the above-center aperture may permit less light to enter the eye.

Figure 16:
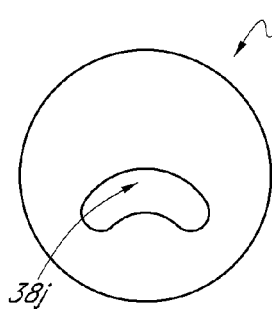
FIG. 16 is a frontal plan view of an embodiment of a mask with a kidney-shaped oval pinhole like aperture.

FIG. 15 shows an embodiment of a mask 34i that includes an aperture 38i formed in the shape of a square. FIG. 16 shows an embodiment of a mask 34j that has a kidney-shaped aperture 38j. It will be appreciated that the apertures shown in FIGS. 7-16 are merely exemplary of non-circular apertures. Other shapes and arrangements may also be provided and are within the scope of the present invention.

The mask 34 preferably has a constant thickness, as discussed below. However, in some embodiments, the thickness of the mask may vary between the inner periphery (near the aperture 38) and the outer periphery. FIG. 17 shows a mask 34k that has a convex profile, i.e., that has a gradually decreasing thickness from the inner periphery to the outer periphery. FIG. 18 shows a mask 34l that has a concave profile, i.e., that has a gradually increasing thickness from the inner periphery to the outer periphery. Other cross-sectional profiles are also possible.

Figure 5:
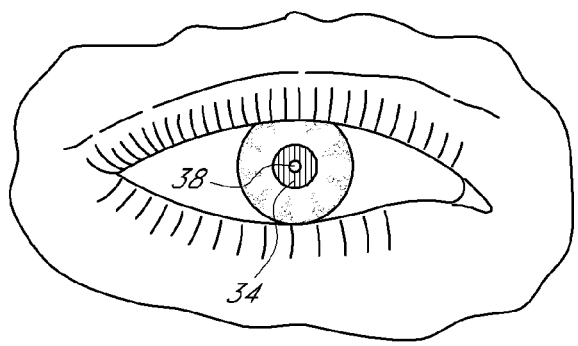
FIG. 5 is a plan view of the human eye with a mask applied thereto.

The annular region 36 is at least partially and preferably completely opaque. The opacity of the annular region 36 prevents light from being transmitted through the mask 34 (as generally shown in FIG. 5). Opacity of the annular region 36 may be achieved in any of several different ways.

For example, in one embodiment, the material used to make mask 34 may be naturally opaque. Alternatively, the material used to make the mask 34 may be substantially clear, but treated with a dye or other pigmentation agent to render region 36 substantially or completely opaque. In still another example, the surface of the mask 34 may be treated physically or chemically (such as by etching) to alter the refractive and transmissive properties of the mask 34 and make it less transmissive to light.

In still another alternative, the surface of the mask 34 may be treated with a particulate deposited thereon. For example, the surface of the mask 34 may be deposited with particulate of titanium, gold or carbon to provide opacity to the surface of the mask 34. In another alternative, the particulate may be encapsulated within the interior of the mask 34, as generally shown in FIG. 19. Finally, the mask 34 may be patterned to provide areas of varying light transmissivity, as generally shown in FIGS. 24-33, which are discussed in detail below.
Modifying Light Transmission Through Ophthalmic Devices Turning to FIG. 20, there is shown a mask 34m formed or made of a woven fabric, such as a mesh of polyester fibers. The mesh may be a cross-hatched mesh of fibers. The mask 34m includes an annular region 36m surrounding an aperture 38m. The annular region 36m comprises a plurality of generally regularly positioned apertures 36m in the woven fabric allow some light to pass through the mask 34m. The amount of light transmitted can be varied and controlled by, for example, moving the fibers closer together or farther apart, as desired. Fibers more densely distributed allow less light to pass through the annular region 36m. Alternatively, the thickness of fibers can be varied to allow more or less light through the openings of the mesh. Making the fiber strands larger results in the openings being smaller.

FIG. 22 shows an embodiment of a mask 34n that includes an annular region 36n that has sub-regions with different opacities. The opacity of the annular region 36n may gradually and progressively increase or decrease, as desired. FIG. 22 shows one embodiment where a first area 42 closest to an aperture 38n has an opacity of approximately 43%. In this embodiment, a second area 44, which is outlying with respect to the first area 42, has a greater opacity, such as 70%. In this embodiment, a third area 46, which is outlying with respect to the second area 42, has an opacity of between 85 to 100%. The graduated opacity of the type described above and shown in FIG. 22 is achieved in one embodiment by, for example, providing different degrees of pigmentation to the areas 42, 44 and 46 of the mask 34n. In another embodiment, light blocking materials of the type described above in variable degrees may be selectively deposited on the surface of a mask to achieve a graduated opacity.

In another embodiment, the mask may be formed from co-extruded rods made of material having different light transmissive properties. The co-extruded rod may then be sliced to provide disks for a plurality of masks, such as those described herein.

Figure 24:
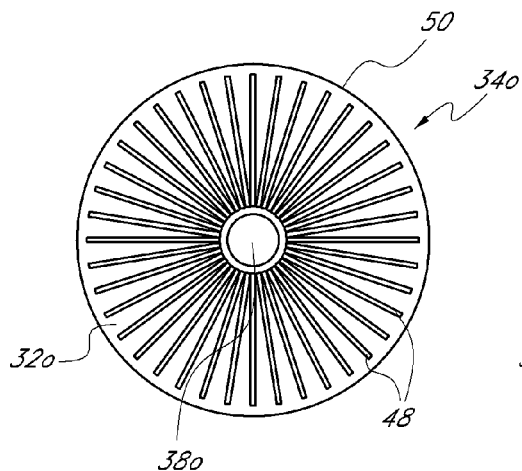
FIG. 24 is a frontal plan view of an embodiment of a mask that includes a centrally located pinhole like aperture and radially extending slots emanating from the center to the periphery of the mask.

FIGS. 24-33 shows examples of masks that have been modified to provide regions of differing opacity. For example, FIG. 24 shows a mask 34o that includes an aperture 38o and a plurality of cutouts 48 in the pattern of radial spokes extending from near the aperture 38o to an outer periphery 50 of the mask 34o. FIG. 24 shows that the cutouts 48 are much more densely distributed about a circumference of the mask near aperture 38o than are the cutouts 48 about a circumference of the mask near the outer periphery 50. Accordingly, more light passes through the mask 34o nearer aperture 38o than near the periphery 50. The change in light transmission through the mask 34o is gradual.

Figure 26:
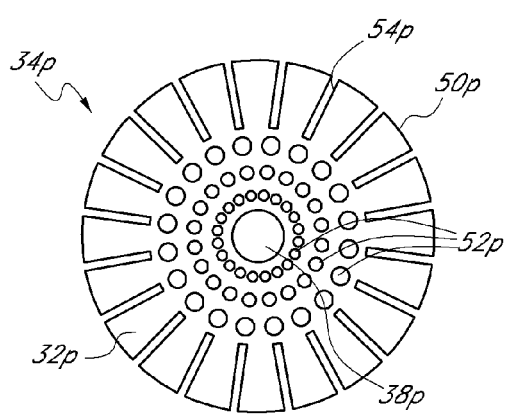
FIG. 26 is a frontal plan view of an embodiment of a mask that includes a central pinhole like aperture, surrounded by a plurality of holes radially spaced from the pinhole like aperture and slots extending radially spaced from the holes and extending to the periphery of the mask.
Figure 27:
FIG. 27 is a side view of the mask of FIG. 26.

FIGS. 26-27 show another embodiment of a mask 34p. The mask 34p includes an aperture 38p and a plurality of circular cutouts 49p, and a plurality of cutouts 51p. The circular cutouts 49p are located proximate the aperture 38p. The cutouts 51p are located between the circular cutouts 49p and the periphery 50p. The density of the circular cutouts 49p generally decreases from the near the aperture 38p toward the periphery 50p. The periphery 50p of the mask 34p is scalloped by the presence of the cutouts 54p, which extend inward from the periphery 50p, to allow some light to pass through the mask at the periphery 50p.

Figure 28:
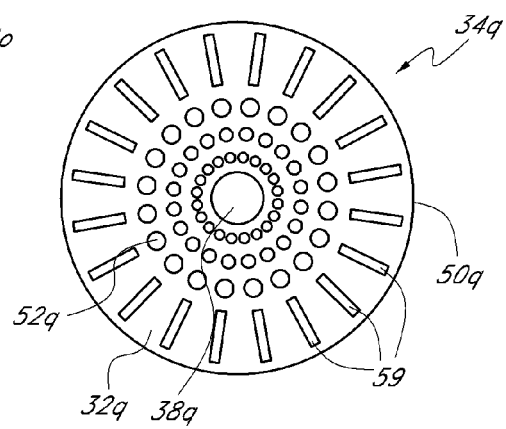
FIG. 28 is a frontal plan view of an embodiment of a mask that includes a central pinhole like aperture, a region that includes a plurality of holes radially spaced from the aperture, and a region that includes rectangular slots spaced radially from the holes.
Figure 25:
FIG. 25 is a side view of the mask of FIG. 24.
Figure 29:
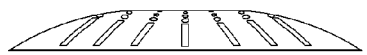
FIG. 29 is a side view of the mask of FIG. 28.

FIGS. 28-29 shows another embodiment similar to that of FIGS. 26-27 wherein a mask 34q includes a plurality of circular cutouts 49q and a plurality of cutouts 51q. The cutouts 51q are disposed along the outside periphery 50q of the mask 34q, but not so as to provide a scalloped periphery.

Figure 30:
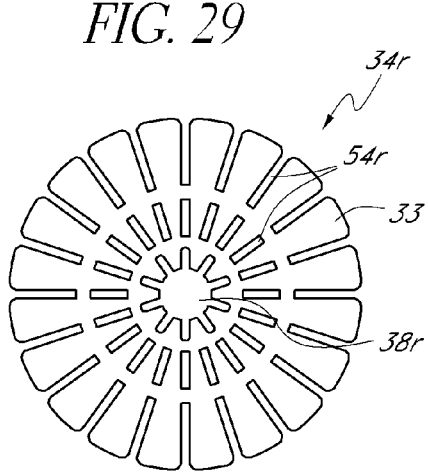
FIG. 30 is a frontal plan view of an embodiment of a mask that includes a non-circular pinhole like aperture, a first set of slots radially spaced from the aperture, and a region that includes a second set of slots extending to the periphery of the mask and radially spaced from the first set of slots.
Figure 31:
FIG. 31 is a side view of the mask of FIG. 30.

FIGS. 30 and 31 illustrate an embodiment of a mask 34r that includes an annular region 36r that is patterned and an aperture 38r that is non-circular. As shown in FIG. 30, the aperture 38r is in the shape of a starburst. Surrounding the aperture 38r is a series of cutouts 51r that are more densely spaced toward the aperture 38r. The mask 34r includes an outer periphery 50r that is scalloped to provide additional light transmission at the outer periphery 50r.

Figure 32:
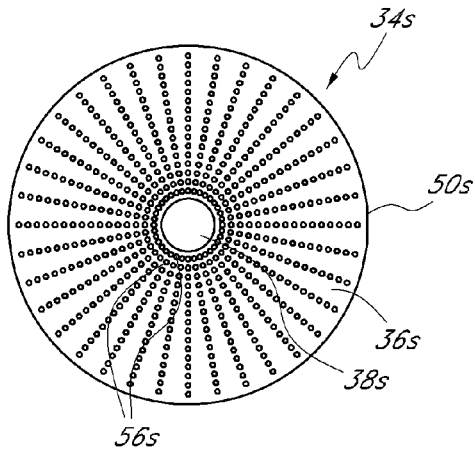
FIG. 32 is a frontal plan view of an embodiment of a mask that includes a central pinhole like aperture and a plurality of holes radially spaced from the aperture.
Figure 33:
FIG. 33 is a side view of the mask of FIG. 32.

FIGS. 32 and 33 show another embodiment of a mask 34s that includes an annular region 36s and an aperture 38s. The annular region 36s is located between an outer periphery 50s of the mask 34s and the aperture 38s. The annular region 36s is patterned. In particular, a plurality of circular openings 56s is distributed over the annular region 36s of the mask 34s. It will be appreciated that the density of the openings 56s is greater near the aperture 38s than near the periphery 50s of the mask 34s. As with the examples described above, this results in a gradual increase in the opacity of the mask 34s from aperture 38s to periphery 50s.

Figure 34:
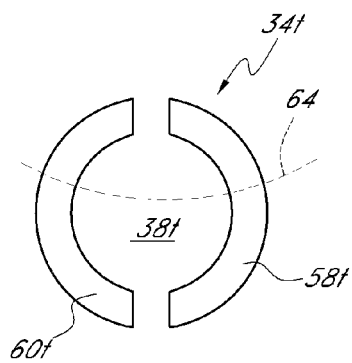
FIG. 34 is an embodiment of a mask that includes two semi-circular mask portions.
Figure 35:
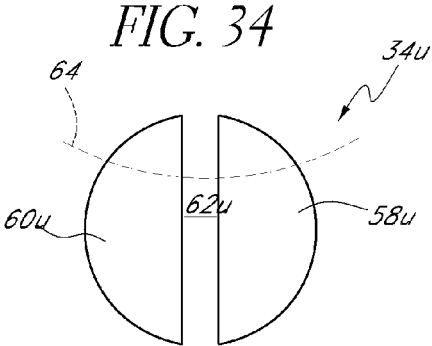
FIG. 35 is an embodiment of a mask including two half-moon shaped portions.
Figure 36:
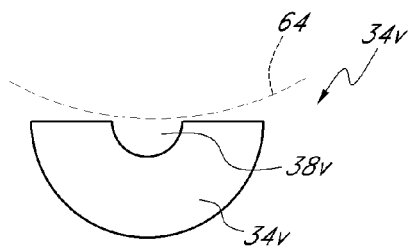
FIG. 36 is an embodiment of a mask that includes a half-moon shaped region and a centrally-located pinhole like aperture.
Figure 40:
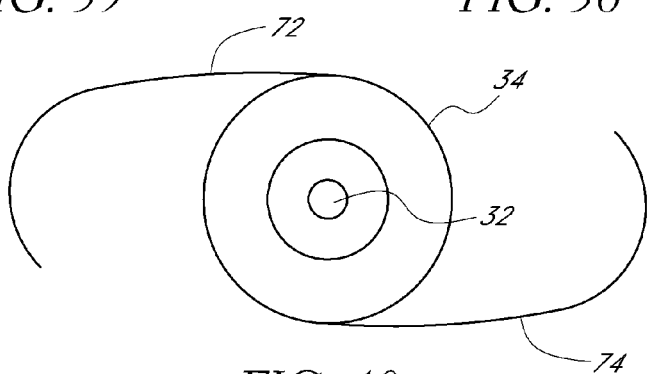
FIG. 40 is another embodiment of a mask that includes connectors for securing the mask within the eye.

FIGS. 34-36 show further embodiments. In particular, FIG. 34 shows a mask 34t that includes a first mask portion 58t and a second mask portion 60t. The mask portions 58t, 60t are generally "C-shaped." As shown in FIG. 34, the mask portions 58t, 60t are implanted or inserted such that the mask portions 58t, 60t define a pinhole or aperture 38t.

FIG. 35 shows another embodiment wherein a mask 34u includes two mask portions 58u, 43u. Each mask portion 58u, 43u is in the shape of a half-moon and is configured to be implanted or inserted in such a way that the two halves define a central gap or opening 45u, which permits light to pass therethrough. Although opening 45u is not a circular pinhole, the mask portions 58u, 43u in combination with the eyelid (shown as dashed line 64) of the patient provide a comparable pinhole effect.

FIG. 36 shows another embodiment of a mask 34v that includes an aperture 38v and that is in the shape of a half-moon. As discussed in more detail below, the mask 34v may be implanted or inserted into a lower portion of the cornea 12 where, as described above, the combination of the mask 34v and the eyelid 64 provides the pinhole effect.

Other embodiments employ different ways of controlling the light transmissivity through a mask. For example, the mask may be a gel-filled disk, as shown in FIG. 19. The gel may be a hydrogel or collagen, or other suitable material that is biocompatible and compatible with the mask material and can be introduced into the interior of the mask. The gel within the mask may include particulate 53 suspended within the gel. Examples of suitable particulate are gold, titanium, and carbon particulate, which, as discussed above, may alternatively be deposited on the surface of the mask.

The material of the mask 34 may be any biocompatible polymeric material. Where a gel is used, the material is suitable for holding a gel. Examples of suitable materials for the mask 34 include the preferred polymethylmethacrylate or other suitable polymers, such as polycarbonates and the like. Of course, as indicated above, for non-gel-filled materials, a preferred material may be a fibrous material, such as a Dacron mesh. Of the materials for use in the mask are those described in section VI herein.

The mask 34 may also be made to include a medicinal fluid or material, such as an antibiotic or other wound healing modulator that can be selectively released after application, insertion, or implantation of the mask 34 into the eye of the patient. Release of an antibiotic or other wound healing modulator after application, insertion, or implantation provides faster and/or improved healing of the incision. The mask 34 may also be coated with other desired drugs or antibiotics. For example, it is known that cholesterol deposits can build up on the eye. Accordingly, the mask 34 may be provided with a releasable cholesterol deterring drug. The drug may be coated on the surface of the mask 34 or, in an alternative embodiment, incorporated into the polymeric material (such as PMMA) from which the mask 34 is formed.

Figure 37:
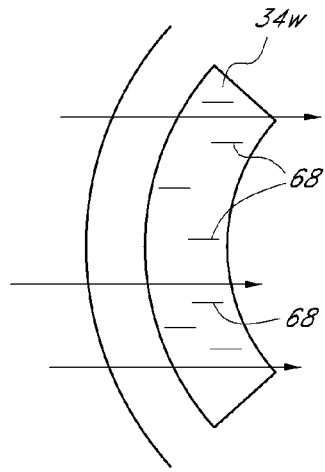
FIG. 37 is an enlarged, diagrammatic view of an embodiment of a mask that includes particulate structure adapted for selectively controlling light transmission through the mask in a low light environment.
Figure 38:
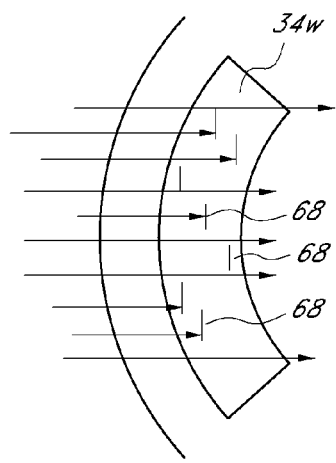
FIG. 38 is a view of the mask of FIG. 37 in a bright light environment.

FIGS. 37 and 38 illustrate one embodiment where a mask 34w comprises a plurality of nanites 68. "Nanites" are small particulate structures that have been adapted to selectively transmit or block light entering the eye of the patient. The particles may be of a very small size typical of the particles used in nanotechnology applications. The nanites 68 are suspended in the gel or otherwise inserted into the interior of the mask 34w, as generally shown in FIGS. 37 and 38. The nanites 68 can be preprogrammed to respond to different light environments.

Thus, as shown in FIG. 38, in a high light environment, the nanites 68 turn and position themselves to substantially and selectively block some of the light from entering the eye. However, in a low light environment where it is desirable for more light to enter the eye, nanites may respond by turning or be otherwise positioned to allow more light to enter the eye, as shown in FIG. 97.

Nano-devices or nanites are crystalline structures grown in laboratories. The nanites may be treated such that they are receptive to different stimuli such as light. In accordance with one aspect of the present invention, the nanites can be imparted with energy where, in response to a low light and high light environments, they rotate in the manner described above and generally shown in FIG. 38.

Nanoscale devices and systems and their fabrication are described in Smith et al., "Nanofabrication," Physics Today, February 1990, pp. 24-30 and in Craighead, "Nanoelectromechanical Systems," Science, Nov. 24, 2000, Vol. 290, pp. 1502-1505, both of which are incorporated by reference herein in their entirety. Tailoring the properties of small-sized particles for optical applications is disclosed in Chen et al. "Diffractive Phase Elements Based on Two-Dimensional Artificial Dielectrics," Optics Letters, Jan. 15, 1995, Vol. 20, No. 2, pp. 121-123, also incorporated by reference herein in its entirety.

Figure 39:
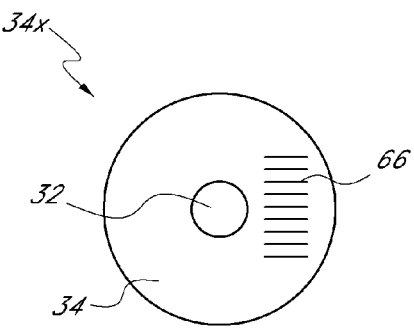
FIG. 39 is an embodiment of a mask that includes a barcode formed on the annular region of the mask.

Masks 34 made in accordance with the present invention may be further modified to include other properties. FIG. 39 shows one embodiment of a mask 34x that includes a bar code 66 or other printed indicia.

Methods of Inserting or Removing an Ophthalmic Device

Figure 49:
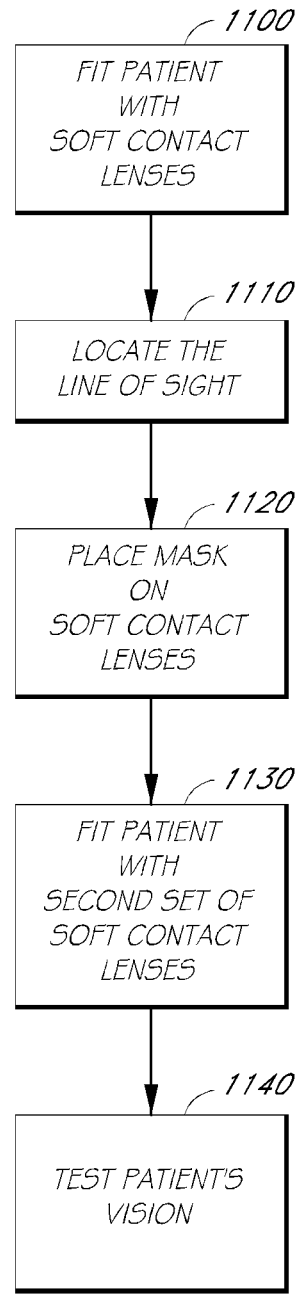
FIG. 49 is a flow chart illustrating one method of screening a patient for the use of a mask.
Figure 50A:
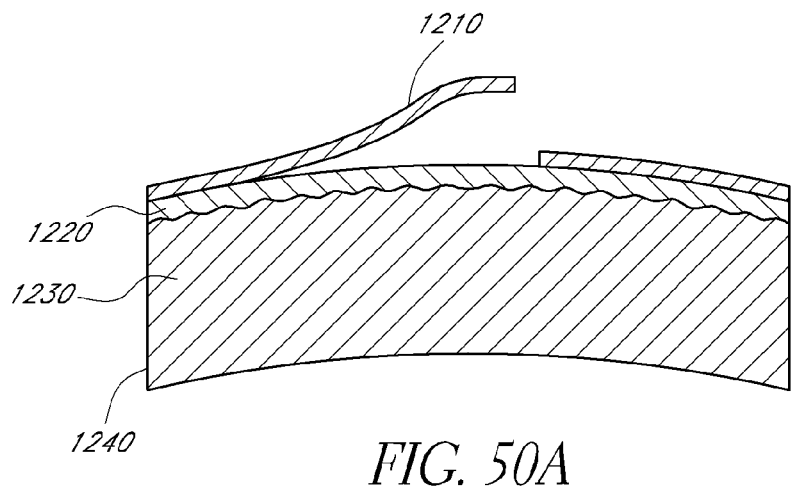
FIGS. 50A-50C show a mask, similar to those described herein, inserted beneath an epithelium sheet of a cornea.
Figure 50B:
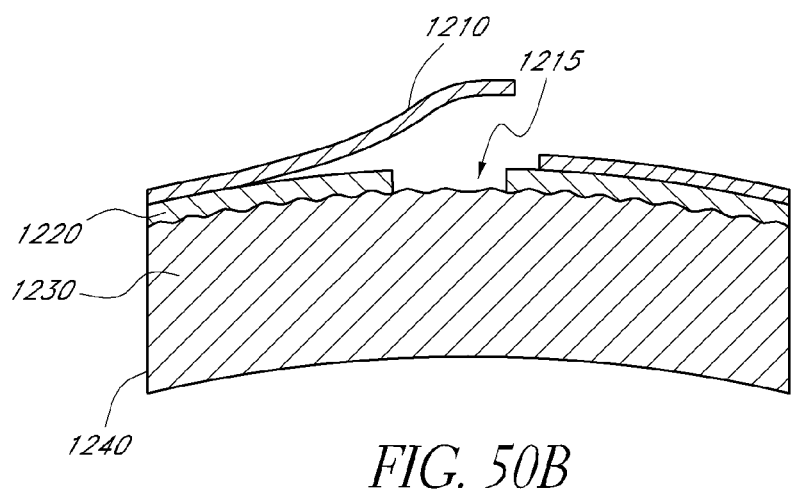
Figure 50C:
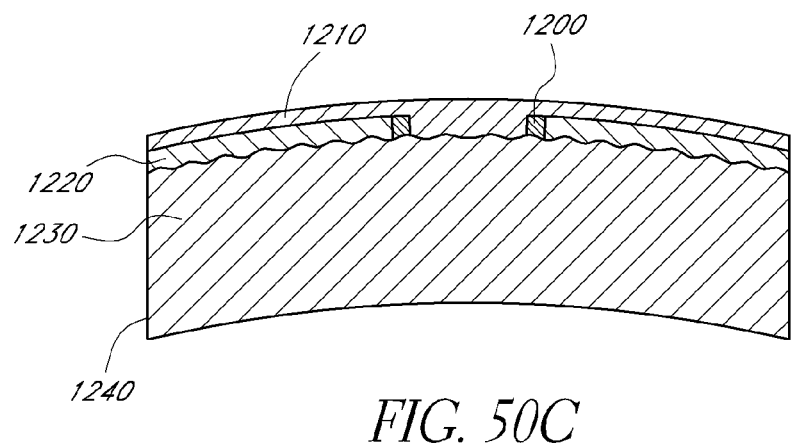
Figure 51A:
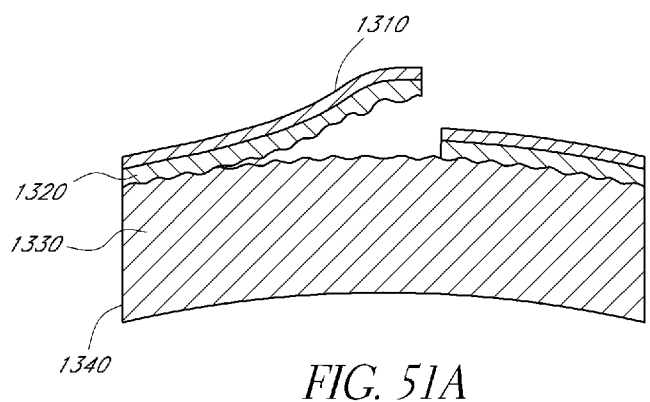
FIGS. 51A-51C show a mask, similar to those described herein, inserted beneath a Bowman's membrane of a cornea.
Figure 51B:
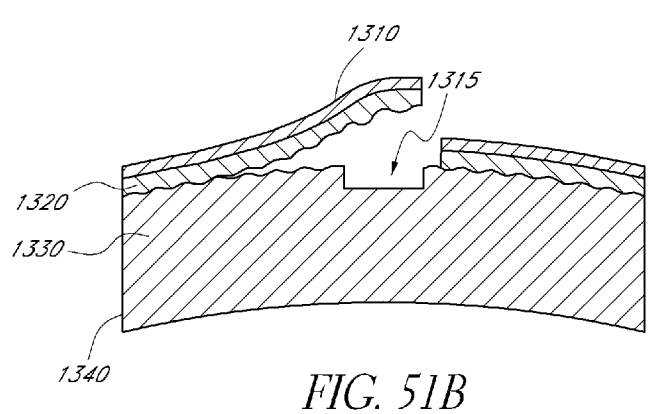
Figure 51C:
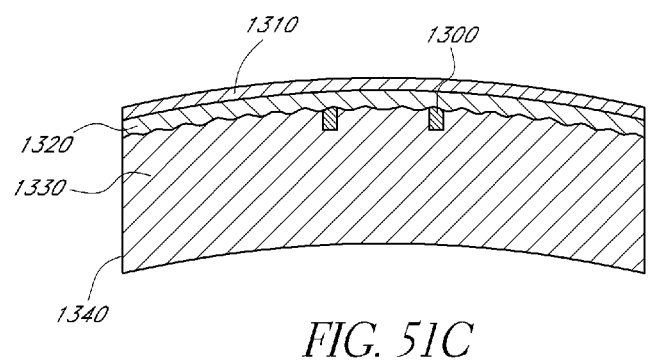

The masks described herein may be incorporated into the eye of a patient in different ways. For example, as discussed in more detail below in connection with FIG. 49, the mask 34 may be provided as a contact lens placed on the surface of the eyeball 10. Alternatively, the mask 34 may be incorporated in an artificial intraocular lens designed to replace the original lens 14 of the patient. The mask 34 may be provided as a corneal implant or inlay, where it is physically inserted between the layers of the cornea 12.

When used as a corneal implant, layers of the cornea 12 are peeled away to allow insertion of the mask 34. Typically, the optical surgeon (typically using a laser) cuts away and peels away a flap of the overlying corneal epithelium. The mask 34 is then inserted and the flap is placed back in its original position where, over time, it grows back and seals the eyeball. In some embodiments, the mask 34 is attached or fixed to the eye 10 by support strands 60 and 62 shown in FIG. 40 and generally described in U.S. Pat. No. 4,976,732, incorporated by reference herein in its entirety.

In certain circumstances, to accommodate the mask 34, the surgeon may be required to remove additional corneal tissue. Thus, in one embodiment, the surgeon may use a laser to peel away additional layers of the cornea 12 to provide a pocket that will accommodate the mask 34. Application of the mask 34 to the cornea 12 of the eye 10 of a patient is described in greater detail in connection with FIGS. 50A-51C.

Removal of the mask 34 may be achieved by simply making an additional incision in the cornea 12, lifting the flap and removing the mask 34. Alternatively, ablation techniques may be used to completely remove the mask 34.

Figure 41:
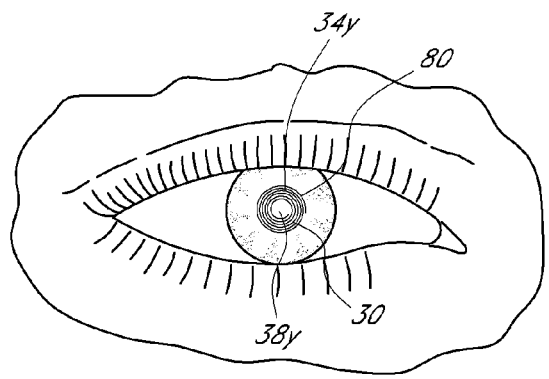
FIG. 41 is a plan view of an embodiment of a mask made of a spiraled fibrous strand.
Figure 42:
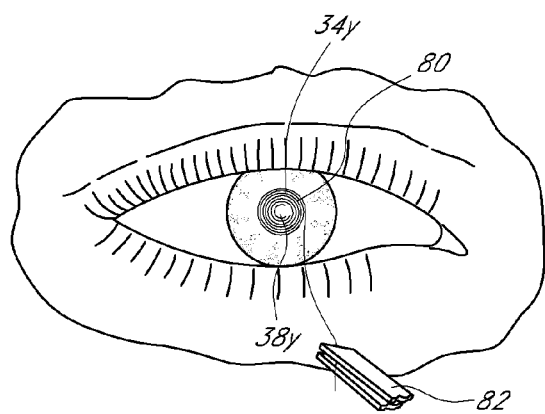
FIG. 42 is a plan view of the mask of FIG. 41 being removed from the eye.

FIGS. 41 and 42 illustrate another embodiment, of a mask 34y that includes a coiled strand 80 of a fibrous or other material. Strand 80 is coiled over itself to form the mask 34y, which may therefore be described as a spiral-like mask. This arrangement provides a pinhole or aperture 38y substantially in the center of the mask 34y. The mask 34y can be removed by a technician or surgeon who grasps the strand 80 with tweezers 82 through an opening made in a flap of the corneal 12. FIG. 42 shows this removal technique.

Further mask details are disclosed in U.S. Pat. No. 4,976,732, issued Dec. 11, 1990 and in U.S. patent application Ser. No. 10/854,033, filed May 26, 2004, both of which are incorporated by reference herein in their entirety.

Additives to Reduce Corneal Deposits and/or Promote Proper Healing

In some circumstances, corneal implants are associated with deposits on the cornea. Loading of one or more polyanionic compounds into the polymeric material of a corneal implant may reduce and/or substantially eliminate deposits on the cornea, possibly by attracting and/or retaining growth factors.

In a preferred embodiment the one or more polyanionic compounds include carbohydrates, proteins, natural proteoglycans, and/or the glycosaminoglycan moieties of proteoglycans, as well as derivatives (such as sulfated derivatives) and salts of compounds such as those in the aforementioned categories. Preferred polyanionic compounds include one or more of dermatan sulfate, chondroitin sulfate, keratan sulfate, heparan sulfate, heparin, dextran sulfate, hyaluronic acid, pentosan polysulfate, xanthan, carrageenan, fibronectin, laminin, chondronectin, vitronectin, poly L-lysine salts, and anionic, preferably sulfated, carbohydrates such as alginate may also be used, as well as salts and derivatives of the listed compounds. Examples of preferred anionic compounds and combinations of polyanionic compounds include keratan sulfate/chrondroitin sulfate-proteoglycan, dermatan sulfate proteoglycan, and dextran sulfate.

In one embodiment, a polyanionic compound comprises acidic sulfate moieties and the sulfur content is greater than about 5% by weight, preferably greater than about 10% by weight. In an even more preferred embodiment, the average molecular weight of a polyanionic compound is about 40,000 to 500,000 Daltons.

In a preferred embodiment, the total weight of the one or more polyanionic compounds in the loaded polymeric material is about 0.1% by weight to about 50% by weight, including about 5% by weight to about 20% by weight, about 12% by weight to about 17% by weight, about 0.5% by weight to about 4% by weight, and about 5% by weight to about 15% by weight. It should be noted that the percentages recited herein in relation to polyanionic compounds, opacification agents and wound healing modulator compounds are percent by weight with 100% being the total weight of the entire mask composition including all additives.

In one embodiment, the body of the mask is formed from a polymeric material having one or more polyanionic compounds loaded therein. Loading of a polyanionic compound is performed by mixing the polyanionic compound with the resin and any other additives of the polymeric material prior to molding or casting of the body of the mask. Although some of a polyanionic compound that is loaded into the polymeric material may be on the surface of the mask, loading is to be distinguished from coating in that a coated material would not have polyanionic material throughout the bulk of the mask.

The loaded polymeric material is preferably made by suspending or dissolving polymer, one or more polyanionic compounds and any other additives (such as wound healing modulators, as described below) in a solvent or solvent system, and then casting a film whereby the solvent or solvent system is removed such as by evaporation. Preferred casting methods include spin casting and other methods, including those known in the art, which can form a thin material of relatively even thickness. Although other methods of making thin substrates, such as extrusion, may be used, solvent casting is generally preferred because it does not need to be done at high temperatures that may cause degradation of some polyanionic compounds. The polymer, polyanionic compound, and/or other additives may be ground or milled, such as by ball milling, to reduce the particle size of the material prior to suspending, dissolving or melting as part of making the mask.

In methods using solvent casting, preferred solvents include those which are capable of dissolving the polymeric material, polyanionic compounds, and/or other additives. A suitable solvent or solvent system (i.e. combination of two or more solvents) may be chosen by one skilled in the art based upon known solubilities for a given polymeric material and/or routine experimentation based upon chemical principles. In solvent casting methods, the temperature of the solvent or solution should be no higher than the boiling point of the solvent or solvent system, and is preferably about 10° C. to about 70° C. During or after casting of the solution to form a film, the temperature may be elevated, including above the boiling point.

In one embodiment, a mask, such as an inlay, comprising PVDF, dextran sulfate, and carbon was made by spin casting. 100 grams of PVDC (about 71% by weight) in the form of pellets was dissolved in 400 grams of dimethylacetamide. 17 grams of carbon (about 12% by weight) and 24 grams of dextran sulfate (about 17% by weight) are ball milled to reduce particle size and then added to the PVDF/DMA solution. The percentages by weight are the percentages of the solids portion, that is the portion that is not the solvent. The solution was at room temperature (approximately 17° C. to about 25° C.). The solution was then spin cast to form a film.

In one embodiment, the device includes a wound healing modulator. When present, the wound healing modulator is on at least one surface or it may be loaded into the polymeric material. A wound healing modulator is defined as a compound that assists in proper healing of a wound, such as by increasing the rate of healing, decreasing inflammation, moderating or suppressing immune response, decreasing scarring, decreasing cell proliferation, reducing infection, encouraging transdifferentiation of keratocytes into cells that lay down collagen, and the like. Wound healing modulators include, without limitation, antibiotics, antineoplastics including antimitotics, antimetabolics and antibiotic types, anti-inflammatories, immunosupressants, and antifungals. Preferred compounds include, but are not limited to, fluorouracil, mitomycin C, paclitaxel, NSAIDs (e.g. ibuprofen, naproxen, flurbiprofen, carprofen, suprofen, ketoprofen), and cyclosporins. Other preferred compounds include proteoglycans, glycosaminoglycans, and salts and derivatives thereof, as well as other carbohydrates and/or proteins, including those disclosed above.

A wound healing modulator may be included in the mask by loading it into the polymeric material as discussed above with respect to the polyanionic compounds. It may also be included by binding it to one or more surfaces of the device. The "binding" of the wound healing modulator to the device may occur by phenomena that do not generally involve chemical bonds, including adsorption, hydrogen bonding, van der Waals forces, electrostatic attraction, ionic bonding, and the like, or it may occur by phenomena that do include chemical bonds. In a preferred embodiment, the total weight of the one or more wound healing modulator compounds in the loaded polymeric material is about 0.1% by weight to about 50% by weight, including about 5% by weight to about 20% by weight, about 12% by weight to about 17% by weight, about 0.5% by weight to about 4% by weight, and about 5% by weight to about 15% by weight.

In one embodiment, carbon, gold or other material on a surface of the mask acts as an adsorbent or otherwise participates in the binding of one or more wound healing modulators to the implant. The material on the surface of the mask that participates in binding the wound healing modulator may be part of the bulk material of the implant (distributed throughout the implant or which migrates to the surface during and/or following formation of the implant) and/or deposited on a surface of the mask, such as an opacification agent as described elsewhere infra. The implant is then exposed to one or more wound healing modulators, such as by dipping in a solution (including dispersions and emulsions) comprising at least one wound healing modulator, to allow wound healing modulator(s) to bind to the implant. The solvent used to assist in applying and binding the wound healing modulator to the implant is preferably biocompatible, does not leave a harmful residue, and/or does not cause dissolution or swelling of the polymeric material of the mask. If more than one wound healing modulator is used, binding may be performed by dipping in a single solution containing all desired wound healing modulators or by dipping the implant in two or more successive solutions, each of which contains one or more of the desired wound healing modulators. The process of binding wound healing modulator to the implant may be done at any time. In one embodiment, at least some of the wound healing modulator is bound to the implant as part of the manufacturing process. In another embodiment, a medical practitioner, such as an ophthalmologist, binds at least some of the wound healing modulator to the implant just prior to implantation.

In alternate embodiments, one or more wound healing modulators are bound to the implant using any suitable method for binding drugs or other useful compounds to implants and medical devices and/or using methods for making drug delivery devices which deliver a drug locally in the area of implantation or placement over a period of time.

Ophthalmic Devices Providing Nutrient Transport

Many of the foregoing masks can be used to improve the depth of focus of a patient. Various additional mask embodiments are discussed below. Some of the embodiments described below include nutrient transport structures that are configured to enhance or maintain nutrient flow between adjacent tissues by facilitating transport of nutrients across the mask. The nutrient transport structures of some of the embodiments described below are configured to at least substantially prevent nutrient depletion in adjacent tissues. The nutrient transport structures can decrease negative effects due to the presence of the mask in adjacent corneal layers when the mask is implanted in the cornea, increasing the longevity of the masks. The inventors have discovered that certain arrangements of nutrient transport structures generate diffraction patterns that interfere with the vision improving effect of the masks described herein. Accordingly, certain masks are described herein that include nutrient transport structures that do not generate diffraction patterns or otherwise interfere with the vision enhancing effects of the mask embodiments.

Figure 43:
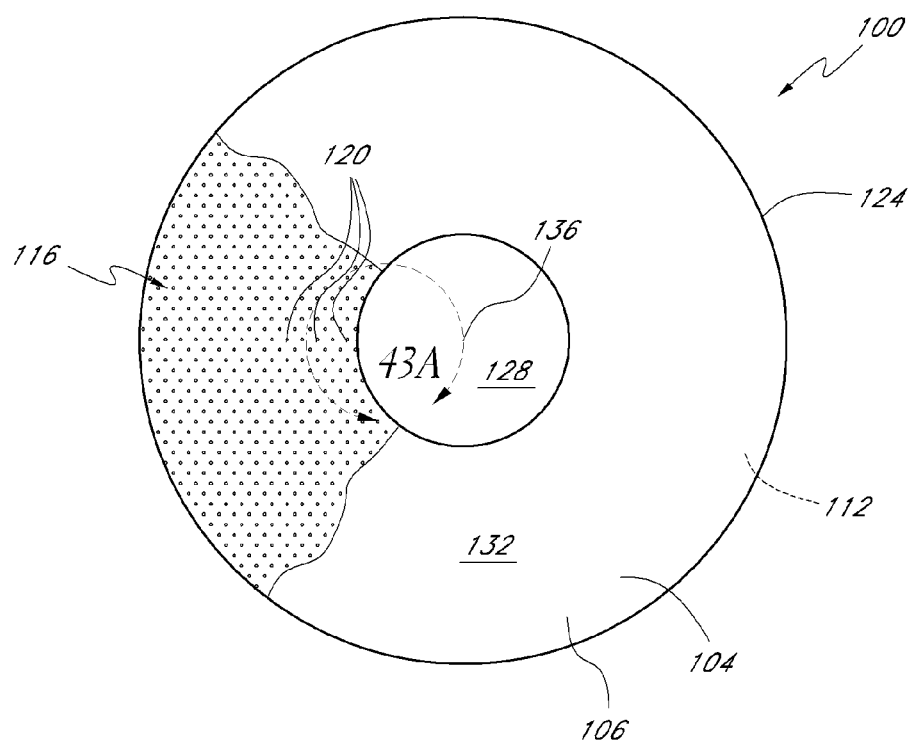
FIG. 43 is a top view of another embodiment of a mask configured to increase depth of focus.
Figure 43A:
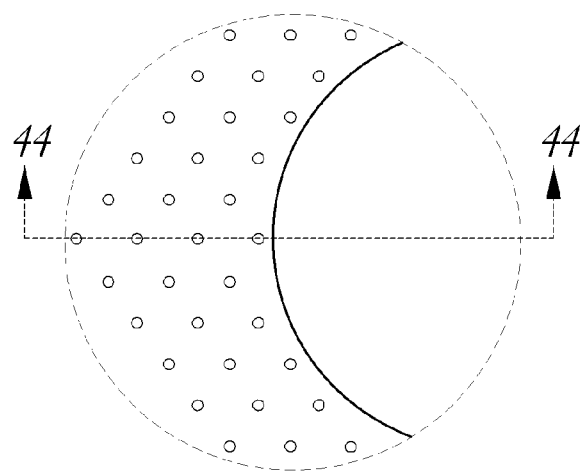
FIG. 43A is an enlarged view of a portion of the view of FIG. 43.
Figure 44A:
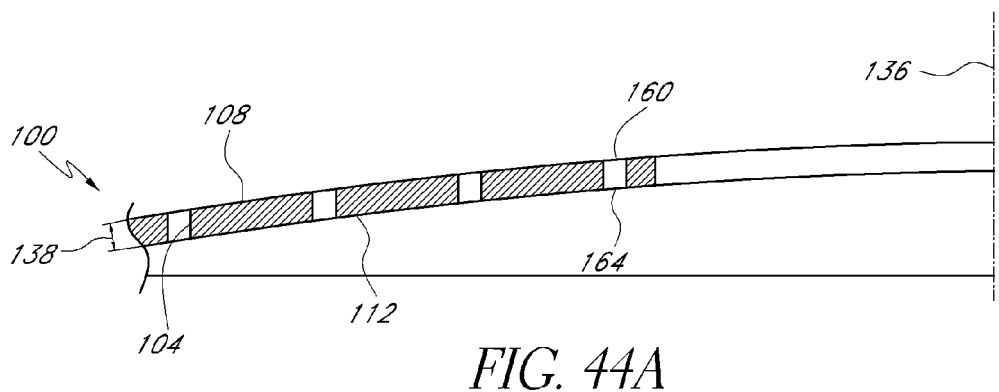
FIG. 44A is a cross-sectional view of the mask of FIG. 43A taken along the section plane 44-44.

FIGS. 43-44 show one embodiment of a mask 100 configured to increase depth of focus of an eye of a patient suffering from presbyopia. The mask 100 is similar to the masks hereinbefore described, except as described differently below. Also, the mask 100 can be formed by any suitable process, such as those discussed below in connection with FIGS. 48a-48d with variations of such processes. The mask 100 is configured to be applied to an eye of a patient, e.g., by being implanted in the cornea of the patient. The mask 100 may be implanted within the cornea in any suitable manner, such as those discussed above in connection with FIGS. 50A-51C.

In one embodiment, the mask 100 includes a body 104 that has an anterior surface 108 and a posterior surface 112. In one embodiment, the body 104 is capable of substantially maintaining natural nutrient flow between the first corneal layer and the second corneal layer. In one embodiment, the material is selected to maintain at least about ninety-six percent of the natural flow of at least one nutrient (e.g., glucose) between a first corneal layer (e.g., the layer 1210) and a second corneal layer (e.g., the layer 1220). The body 104 may be formed of any suitable material, including at least one of an open cell foam material, an expanded solid material, and a substantially opaque material. In one embodiment, the material used to form the body 104 has relatively high water content.

Figure 45A:
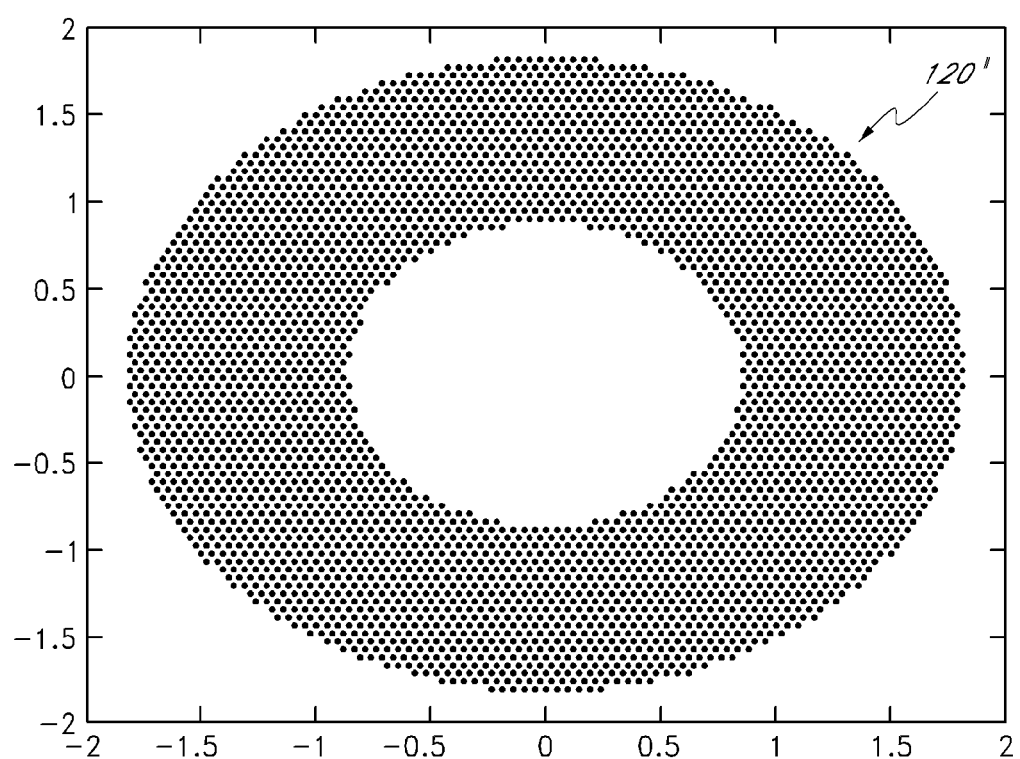
FIG. 45A is a graphical representation of one arrangement of holes of a plurality of holes that may be formed on the mask of FIG. 43.

In one embodiment, the mask 100 includes and a nutrient transport structure 116. The nutrient transport structure 116 may comprise a plurality of holes 120. The holes 120 are shown on only a portion of the mask 100, but the holes 120 preferably are located throughout the body 104 in one embodiment. In one embodiment, the holes 120 are arranged in a hex pattern, which is illustrated by a plurality of locations 120' in FIG. 45A. As discussed below, a plurality of locations may be defined and later used in the later formation of a plurality of holes 120 on the mask 100. The mask 100 has an outer periphery 124 that defines an outer edge of the body 104. In some embodiments, the mask 100 includes an aperture 128 at least partially surrounded by the outer periphery 124 and a non-transmissive portion 132 located between the outer periphery 124 and the aperture 128.

Preferably the mask 100 is symmetrical, e.g., symmetrical about a mask axis 136. In one embodiment, the outer periphery 124 of the mask 100 is circular. The masks in general have has a diameter within the range of from about 3 mm to about 8 mm, often within the range of from about 3.5 mm to about 6 mm, and less than about 6 mm in one embodiment. In another embodiment, the mask is circular and has a diameter in the range of 4 to 6 mm. In another embodiment, the mask 100 is circular and has a diameter of less than 4 mm. The outer periphery 124 has a diameter of about 3.8 mm in another embodiment. In some embodiments, masks that are asymmetrical or that are not symmetrical about a mask axis provide benefits, such as enabling a mask to be located or maintained in a selected position with respect to the anatomy of the eye.

The body 104 of the mask 100 may be configured to coupled with a particular anatomical region of the eye. The body 104 of the mask 100 may be configured to conform to the native anatomy of the region of the eye in which it is to be applied. For example, where the mask 100 is to be coupled with an ocular structure that has curvature, the body 104 may be provided with an amount of curvature along the mask axis 136 that corresponds to the anatomical curvature. For example, one environment in which the mask 100 may be deployed is within the cornea of the eye of a patient. The cornea has an amount of curvature that varies from person to person about a substantially constant mean value within an identifiable group, e.g., adults. When applying the mask 100 within the cornea, at least one of the anterior and posterior surfaces 108, 112 of the mask 100 may be provided with an amount of curvature corresponding to that of the layers of the cornea between which the mask 100 is applied.

In some embodiments, the mask 100 has a desired amount of optical power. Optical power may be provided by configuring the at least one of the anterior and posterior surfaces 108, 112 with curvature. In one embodiment, the anterior and posterior surfaces 108, 112 are provided with different amounts of curvature. In this embodiment, the mask 100 has varying thickness from the outer periphery 124 to the aperture 128.

In one embodiment, one of the anterior surface 108 and the posterior surface 112 of the body 104 is substantially planar. In one planar embodiment, very little or no uniform curvature can be measured across the planar surface. In another embodiment, both of the anterior and posterior surfaces 108, 112 are substantially planar. In general, the thickness of the inlay may be within the range of from about 1 micron to about 40 micron, and often in the range of from about 5 micron to about 20 micron. In one embodiment, the body 104 of the mask 100 has a thickness 138 of between about 5 micron and about 10 micron. In one embodiment, the thickness 138 of the mask 100 is about 5 micron. In another embodiment, the thickness 138 of the mask 100 is about 8 micron. In another embodiment, the thickness 138 of the mask 100 is about 10 micron.

Thinner masks generally are more suitable for applications wherein the mask 100 is implanted at a relatively shallow location in (e.g., close to the anterior surface of) the cornea. In thinner masks, the body 104 may be sufficiently flexible such that it can take on the curvature of the structures with which it is coupled without negatively affecting the optical performance of the mask 100. In one application, the mask 100 is configured to be implanted about 5 um beneath the anterior surface of the cornea. In another application, the mask 100 is configured to be implanted about 52 um beneath the anterior surface of the cornea. In another application, the mask 100 is configured to be implanted about 125 um beneath the anterior surface of the cornea. Further details regarding implanting the mask 100 in the cornea are discussed above in connection with FIGS. 50A-51C.

A substantially planar mask has several advantages over a non-planar mask. For example, a substantially planar mask can be fabricated more easily than one that has to be formed to a particular curvature. In particular, the process steps involved in inducing curvature in the mask 100 can be eliminated. Also, a substantially planar mask may be more amenable to use on a wider distribution of the patient population (or among different sub-groups of a broader patient population) because the substantially planar mask uses the curvature of each patient's cornea to induce the appropriate amount of curvature in the body 104.

In some embodiments, the mask 100 is configured specifically for the manner and location of coupling with the eye. In particular, the mask 100 may be larger if applied over the eye as a contact lens or may be smaller if applied within the eye posterior of the cornea, e.g., proximate a surface of the lens of the eye. As discussed above, the thickness 138 of the body 104 of the mask 100 may be varied based on where the mask 100 is implanted. For implantation at deeper levels within the cornea, a thicker mask may be advantageous. Thicker masks are advantageous in some applications. For example, they are generally easier to handle, and therefore are easier to fabricate and to implant. Thicker masks may benefit more from having a preformed curvature than thinner masks. A thicker mask could be configured to have little or no curvature prior to implantation if it is configured to conform to the curvature of the native anatomy when applied.

The aperture 128 is configured to transmit substantially all incident light along the mask axis 136. The non-transmissive portion 132 surrounds at least a portion of the aperture 128 and substantially prevents transmission of incident light thereon. As discussed in connection with the above masks, the aperture 128 may be a through-hole in the body 104 or a substantially light transmissive (e.g., transparent) portion thereof. The aperture 128 of the mask 100 generally is defined within the outer periphery 124 of the mask 100. The aperture 128 may take any of suitable configurations, such as those described above in connection with FIGS. 6-42.

In one embodiment, the aperture 128 is substantially circular and is substantially centered in the mask 100. The size of the aperture 128 may be any size that is effective to increase the depth of focus of an eye of a patient suffering from presbyopia. For example, the aperture 128 can be circular, having a diameter of less than about 2.2 mm in one embodiment. In another embodiment, the diameter of the aperture is between about 1.8 mm and about 2.2 mm. In another embodiment, the aperture 128 is circular and has a diameter of about 1.8 mm or less. In another embodiment, the diameter of the aperture is about 1.6 mm. Most apertures will have a diameter within the range of from about 1.0 mm to about 2.5 mm, and often within the range of from about 1.3 mm to about 1.9 mm.

The non-transmissive portion 132 is configured to prevent transmission of radiant energy through the mask 100. For example, in one embodiment, the non-transmissive portion 132 prevents transmission of substantially all of at least a portion of the spectrum of the incident radiant energy. In one embodiment, the non-transmissive portion 132 is configured to prevent transmission of substantially all visible light, e.g., radiant energy in the electromagnetic spectrum that is visible to the human eye. The non-transmissive portion 132 may substantially prevent transmission of radiant energy outside the range visible to humans in some embodiments.

As discussed above in connection with FIG. 3, preventing transmission of light through the non-transmissive portion 132 decreases the amount of light that reaches the retina and the fovea that would not converge at the retina and fovea to form a sharp image. As discussed above in connection with FIG. 4, the size of the aperture 128 is such that the light transmitted therethrough generally converges at the retina or fovea. Accordingly, a much sharper image is presented to the eye than would otherwise be the case without the mask 100.

In one embodiment, the non-transmissive portion 132 prevents transmission of about 90 percent of incident light. In another embodiment, the non-transmissive portion 132 prevents transmission of about 92 percent of all incident light. The non-transmissive portion 132 of the mask 100 may be configured to be opaque to prevent the transmission of light. As used herein the term "opaque" is intended to be a broad term meaning capable of preventing the transmission of radiant energy, e.g., light energy, and also covers structures and arrangements that absorb or otherwise block all or less than all or at least a substantial portion of the light. In one embodiment, at least a portion of the body 104 is configured to be opaque to more than 99 percent of the light incident thereon.

As discussed above, the non-transmissive portion 132 may be configured to prevent transmission of light without absorbing the incident light. For example, the mask 100 could be made reflective or could be made to interact with the light in a more complex manner, as discussed in U.S. Pat. No. 6,551,424, issued Apr. 29, 2003, which is hereby incorporated by reference herein in its entirety.

As discussed above, the mask 100 also has a nutrient transport structure that in some embodiments comprises the plurality of holes 120. The presence of the plurality of holes 120 (or other transport structure) may affect the transmission of light through the non-transmissive portion 132 by potentially allowing more light to pass through the mask 100. In one embodiment, the non-transmissive portion 132 is configured to absorb about 99 percent or more of the incident light from passing through the mask 100 without holes 120 being present. The presence of the plurality of holes 120 allows more light to pass through the non-transmissive portion 132 such that only about 92 percent of the light incident on the non-transmissive portion 132 is prevented from passing through the non-transmissive portion 132. The holes 120 may reduce the benefit of the aperture 128 on the depth of focus of the eye by allowing more light to pass through the non-transmissive portion to the retina.

Reduction in the depth of focus benefit of the aperture 128 due to the holes 120 is balanced by the nutrient transmission benefits of the holes 120. In one embodiment, the transport structure 116 (e.g., the holes 120) is capable of substantially maintaining natural nutrient flow from a first corneal layer (i.e., one that is adjacent to the anterior surface 108 of the mask 100) to the second corneal layer (i.e., one that is adjacent to the posterior surface 112 of the mask 100). The plurality of holes 120 are configured to enable nutrients to pass through the mask 100 between the anterior surface 108 and the posterior surface 112. As discussed above, the holes 120 of the mask 100 shown in FIG. 43 may be located anywhere on the mask 100. Other mask embodiments described herein below locate substantially all of the nutrient transport structure in one or more regions of a mask.

The holes 120 of FIG. 43 extends at least partially between the anterior surface 108 and the posterior surface 112 of the mask 100. In one embodiment, each of the holes 120 includes a hole entrance 140 and a hole exit 164. The hole entrance 140 is located adjacent to the anterior surface 108 of the mask 100. The hole exit 164 is located adjacent to the posterior surface 112 of the mask 100. In one embodiment, each of the holes 120 extends the entire distance between the anterior surface 108 and the posterior surface 112 of the mask 100.

The transport structure 116 is configured to maintain the transport of one or more nutrients across the mask 100. The transport structure 116 of the mask 100 provides sufficient flow of one or more nutrients across the mask 100 to prevent depletion of nutrients at least at one of the first and second corneal layers (e.g., the layers 1210 and 1220). One nutrient of particular importance to the viability of the adjacent corneal layers is glucose. The transport structure 116 of the mask 100 provides sufficient flow of glucose across the mask 100 between the first and second corneal layers to prevent glucose depletion that would harm the adjacent corneal tissue. Thus, the mask 100 is capable of substantially maintaining nutrient flow (e.g., glucose flow) between adjacent corneal layers. In one embodiment, the nutrient transport structure 116 is configured to prevent depletion of more than about 4 percent of glucose (or other biological substance) in adjacent tissue of at least one of the first corneal layer and the second corneal layer.

The holes 120 may be configured to maintain the transport of nutrients across the mask 100. In one embodiment, the holes 120 are formed with a diameter of about 0.015 mm or more. In another embodiment, the holes have a diameter of about 0.020 mm. In another embodiment, the holes have a diameter of about 0.025 mm. In another embodiment, the holes have a diameter of about 0.027 mm. In another embodiment, the holes 120 have a diameter in the range of about 0.020 mm to about 0.029 mm. The number of holes in the plurality of holes 120 is selected such that the sum of the surface areas of the hole entrances 140 of all the holes 100 comprises about 5 percent or more of surface area of the anterior surface 108 of the mask 100. In another embodiment, the number of holes 120 is selected such that the sum of the surface areas of the hole exits 164 of all the holes 120 comprises about 5 percent or more of surface area of the posterior surface 112 of the mask 100. In another embodiment, the number of holes 120 is selected such that the sum of the surface areas of the hole exits 164 of all the holes 120 comprises about 5 percent or more of surface area of the posterior surface 112 of the mask 112 and the sum of the surface areas of the hole entrances 140 of all the holes 120 comprises about 5 percent or more of surface area of the anterior surface 108 of the mask 100. In another embodiment, the plurality of holes 120 may comprise about 1600 microperforations.

Each of the holes 120 may have a relatively constant cross-sectional area. In one embodiment, the cross-sectional shape of each of the holes 120 is substantially circular. Each of the holes 120 may comprise a cylinder extending between the anterior surface 108 and the posterior surface 112.

The relative position of the holes 120 is of interest in some embodiments. As discussed above, the holes 120 of the mask 100 are hex-packed, e.g., arranged in a hex pattern. In particular, in this embodiment, each of the holes 120 is separated from the adjacent holes 120 by a substantially constant distance, sometimes referred to herein as a hole pitch. In one embodiment, the hole pitch is about 0.045 mm.

In a hex pattern, the angles between lines of symmetry are approximately 43 degrees. The spacing of holes along any line of holes is generally within the range of from about 30 microns to about 100 microns, and, in one embodiment, is approximately 43 microns. The hole diameter is generally within the range of from about 10 microns to about 100 microns, and in one embodiment, is approximately 20 microns. The hole spacing and diameter are related if you want to control the amount of light coming through. The light transmission is a function of the sum of hole areas as will be understood by those of skill in the art in view of the disclosure herein.

The embodiment of FIG. 43 advantageously enables nutrients to flow from the first corneal layer to the second corneal layer. The inventors have discovered that negative visual effects can arise due to the presence of the transport structure 116. For example, in some cases, a hex packed arrangement of the holes 120 can generate diffraction patterns visible to the patient. For example, patients might observe a plurality of spots, e.g., six spots, surrounding a central light with holes 120 having a hex patterned.

The inventors have discovered a variety of techniques that produce advantageous arrangements of a transport structure such that diffraction patterns and other deleterious visual effects do not substantially inhibit other visual benefits of a mask. In one embodiment, where diffraction effects would be observable, the nutrient transport structure is arranged to spread the diffracted light out uniformly across the image to eliminate observable spots. In another embodiment, the nutrient transport structure employs a pattern that substantially eliminates diffraction patterns or pushes the patterns to the periphery of the image.

Figure 45B:
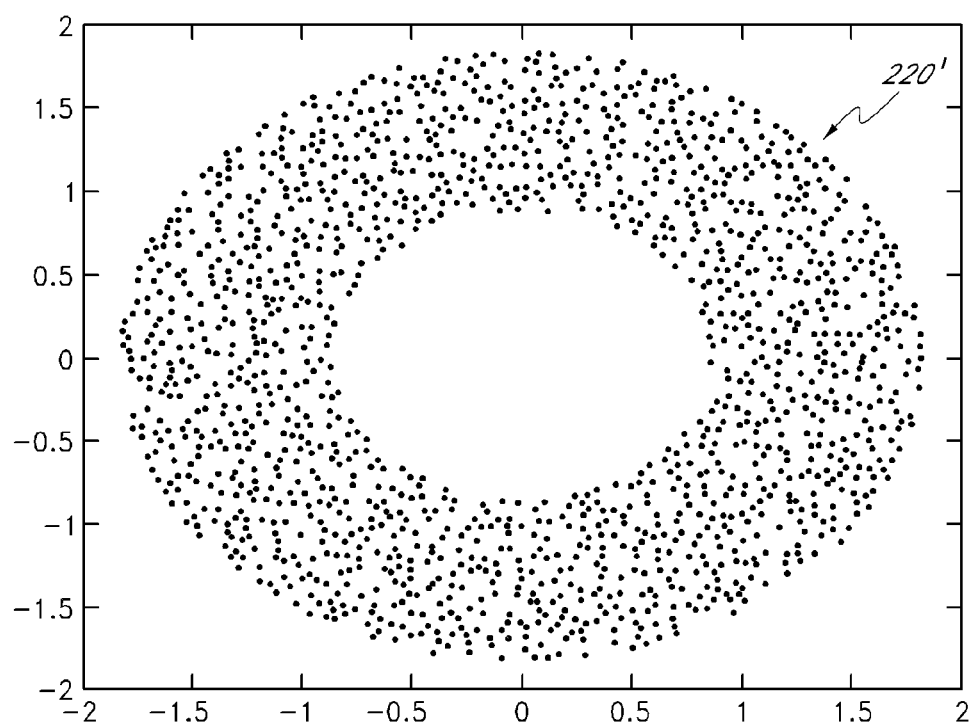
FIG. 45B is a graphical representation of another arrangement of holes of a plurality of holes that may be formed on the mask of FIG. 43.
Figure 45C:
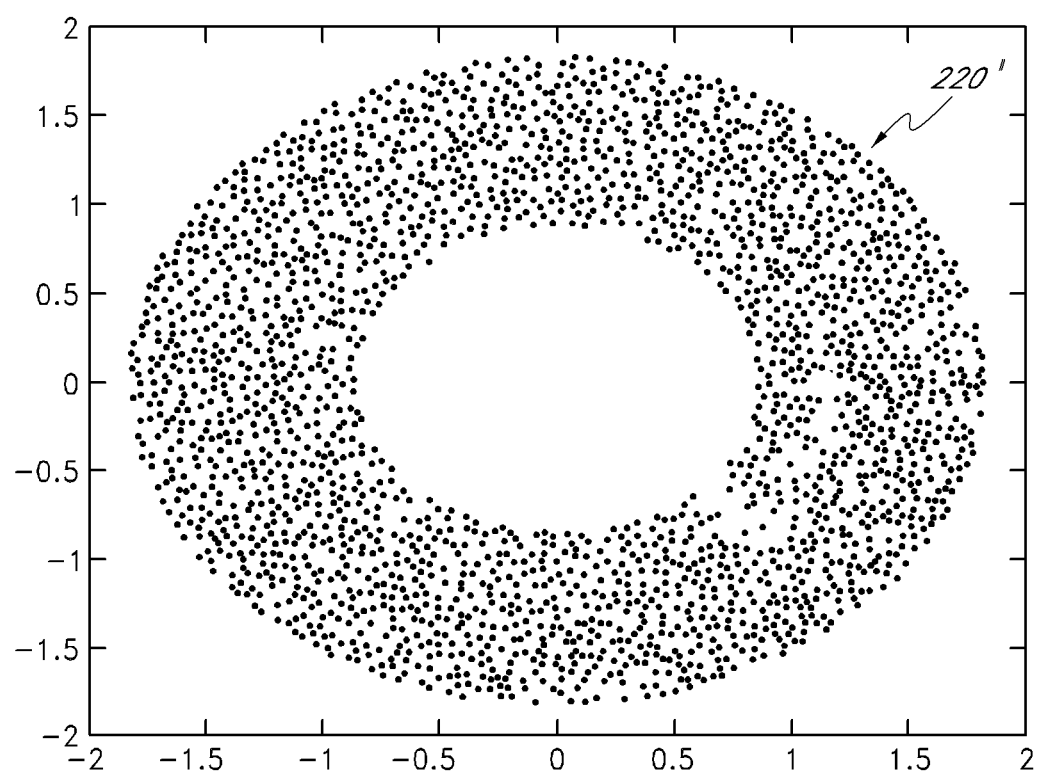
FIG. 45C is a graphical representation of another arrangement of holes of a plurality of holes that may be formed on the mask of FIG. 43.

FIG. 45B-45C show two embodiments of patterns of holes 220 that may be applied to a mask that is otherwise substantially similar to the mask 100. The holes 220 of the hole patterns of FIGS. 45B-45C are spaced from each other by a random hole spacing or hole pitch. In other embodiments discussed below, holes are spaced from each other by a non-uniform amount, e.g., not a random amount. In one embodiment, the holes 220 have a substantially uniform shape (cylindrical shafts having a substantially constant cross-sectional area). FIG. 45C illustrates a plurality of holes 220 separated by a random spacing, wherein the density of the holes is greater than that of FIG. 45B. Generally, the higher the percentage of the mask body that has holes the more the mask will transport nutrients in a manner similar to the native tissue. One way to provide a higher percentage of hole area is to increase the density of the holes. Increased hole density can also permit smaller holes to achieve the same nutrient transport as is achieved by less dense, larger holes.

Figure 46A:
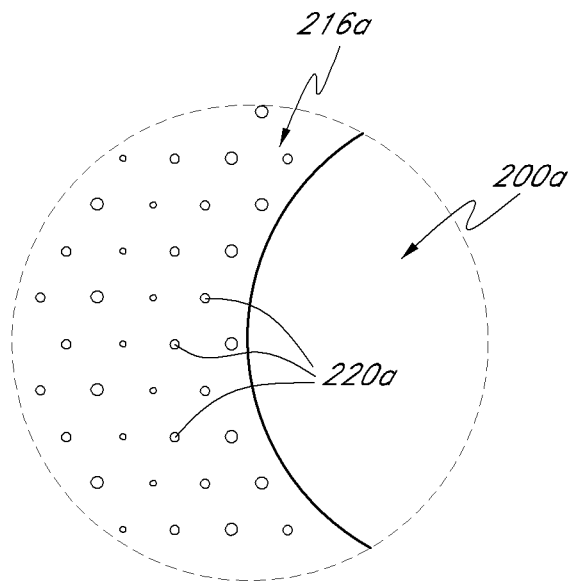
FIG. 46A is an enlarged view similar to that of FIG. 43A showing a variation of a mask having non-uniform size.

FIG. 46A shows a portion of another mask 200a that is substantially similar to the mask 100, except described differently below. The mask 200a can be made of any of the materials discussed herein. The mask 200a can be formed by any suitable process, such as those discussed below in connection with FIGS. 48a-48d and with variations of such processes. The mask 200a has a nutrient transport structure 216a that includes a plurality of holes 220a. A substantial number of the holes 220a have a non-uniform size. The holes 220a may be uniform in cross-sectional shape. The cross-sectional shape of the holes 220a is substantially circular in one embodiment. The holes 220a may be circular in shape and have the same diameter from a hole entrance to a hole exit, but are otherwise non-uniform in at least one aspect, e.g., in size. It may be preferable to vary the size of a substantial number of the holes by a random amount. In another embodiment, the holes 220*a* are non-uniform (e.g., random) in size and are separated by a non-uniform (e.g., a random) spacing.

Figure 46B:
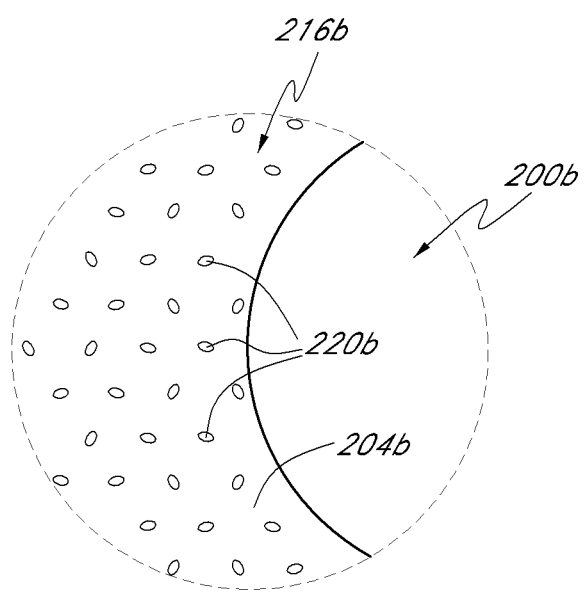
FIG. 46B is an enlarged view similar to that of FIG. 43A showing a variation of a mask having a non-uniform facet orientation.

FIG. 46B illustrates another embodiment of a mask 200*b* that is substantially similar to the mask 100, except as described differently below. The mask 200*b* can be made of any of the materials discussed herein. Also, the mask 200*b* can be formed by any suitable process, such as those discussed below in connection with FIGS. 48*a*-48*d* and with variations of such processes. The mask 200*b* includes a body 204*b*. The mask 200*b* has a transport structure 216*b* that includes a plurality of holes 220*b* with a non-uniform facet orientation. In particular, each of the holes 220*b* has a hole entrance that may be located at an anterior surface of the mask 200*b*. A facet of the hole entrance is defined by a portion of the body 204*b* of the mask 200*b* surrounding the hole entrance. The facet is the shape of the hole entrance at the anterior surface. In one embodiment, most or all the facets have an elongate shape, e.g., an oblong shape, with a long axis and a short axis that is perpendicular to the long axis. The facets may be substantially uniform in shape. In one embodiment, the orientation of facets is not uniform. For example, a substantial number of the facets may have a non-uniform orientation. In one arrangement, a substantial number of the facets have a random orientation. In some embodiments, the facets are non-uniform (e.g., random) in shape and are non-uniform (e.g., random) in orientation.

Other embodiments may be provided that vary at least one aspect, including one or more of the foregoing aspects, of a plurality of holes to reduce the tendency of the holes to produce visible diffraction patterns or patterns that otherwise reduce the vision improvement that may be provided by a mask with an aperture, such as any of those described above. For example, in one embodiment, the hole size, shape, and orientation of at least a substantial number of the holes may be varied randomly or may be otherwise non-uniform.

Figure 47:
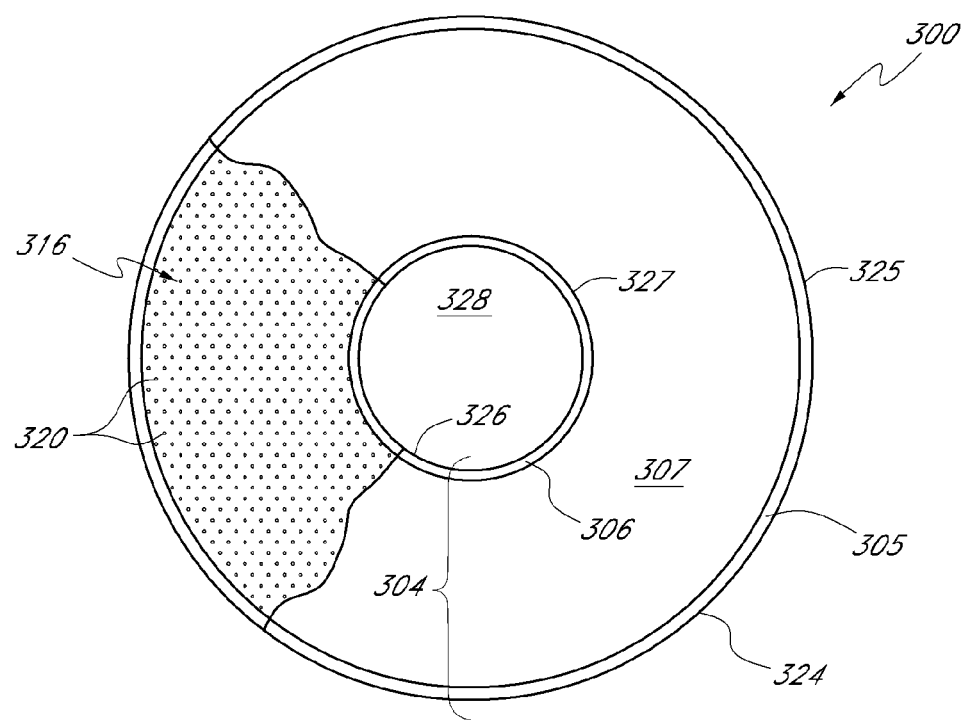
FIG. 47 is a top view of another embodiment of a mask having a hole region and a peripheral region.
Figure 48:
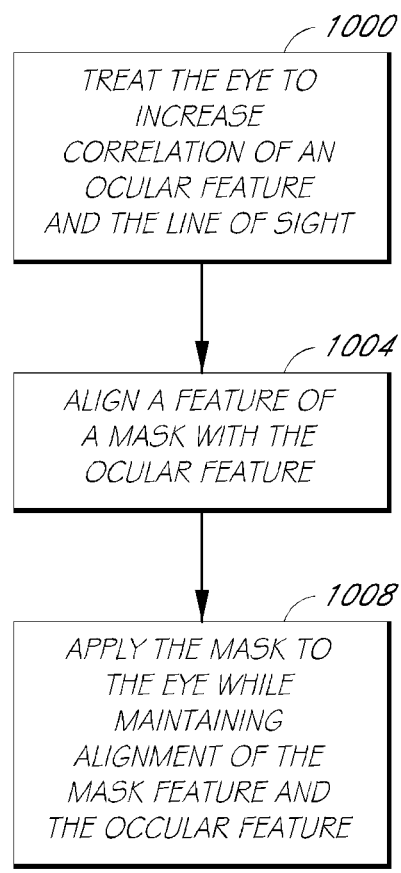
FIG. 48 is a flow chart illustrating one method of aligning a mask with an axis of the eye based on observation of an anatomical feature of the eye.

FIG. 47 shows another embodiment of a mask 300 that is substantially similar to any of the masks hereinbefore described, except as described differently below. The mask 300 can be made of any of the materials discussed herein. Also, the mask 300 can be formed by any suitable process, such as those discussed below in connection with FIGS. 48*a*-48*d* and with variations of such processes. The mask 300 includes a body 304. The body 304 has an outer peripheral region 305, an inner peripheral region 306, and a hole region 307. The hole region 307 is located between the outer peripheral region 305 and the inner peripheral region 306. The body 304 may also include an aperture region, where the aperture (discussed below) is not a through hole. The mask 300 also includes a nutrient transport structure 316. In one embodiment, the nutrient transport structure includes a plurality of holes. At least a substantial portion of the holes (e.g., all of the holes) are located in the hole region 307. As above, only a portion of the nutrient structure 316 is shown for simplicity. But it should be understood that the holes may be located through the hole region 307.

The outer peripheral region 305 may extend from an outer periphery 324 of the mask 300 to a selected outer circumference 326 of the mask 300. The selected outer circumference 325 of the mask 300 is located a selected radial distance from the outer periphery 324 of the mask 300. In one embodiment, the selected outer circumference 325 of the mask 300 is located about 0.05 mm from the outer periphery 324 of the mask 300.

The inner peripheral region 306 may extend from an inner location, e.g., an inner periphery 326 adjacent an aperture 328 of the mask 300 to a selected inner circumference 327 of the mask 300. The selected inner circumference 327 of the mask 300 is located a selected radial distance from the inner periphery 326 of the mask 300. In one embodiment, the selected inner circumference 327 of the mask 300 is located about 0.05 mm from the inner periphery 326.

The mask 300 may be the product of a process that involves random selection of a plurality of locations and formation of holes on the mask 300 corresponding to the locations. As discussed further below, the method can also involve determining whether the selected locations satisfy one or more criteria. For example, one criterion prohibits all, at least a majority, or at least a substantial portion of the holes from being formed at locations that correspond to the inner or outer peripheral regions 305, 306. Another criterion prohibits all, at least a majority, or at least a substantial portion of the holes from being formed too close to each other. For example, such a criterion could be used to assure that a wall thickness, e.g., the shortest distance between adjacent holes, is not less than a predetermined amount. In one embodiment, the wall thickness is prevented from being less than about 20 microns.

In a variation of the embodiment of FIG. 47, the outer peripheral region 305 is eliminated and the hole region 307 extends from the inner peripheral region 306 to an outer periphery 324. In another variation of the embodiment of FIG. 47, the inner peripheral region 306 is eliminated and the hole region 307 extends from the outer peripheral region 305 to an inner periphery 326.

Figure 44B:
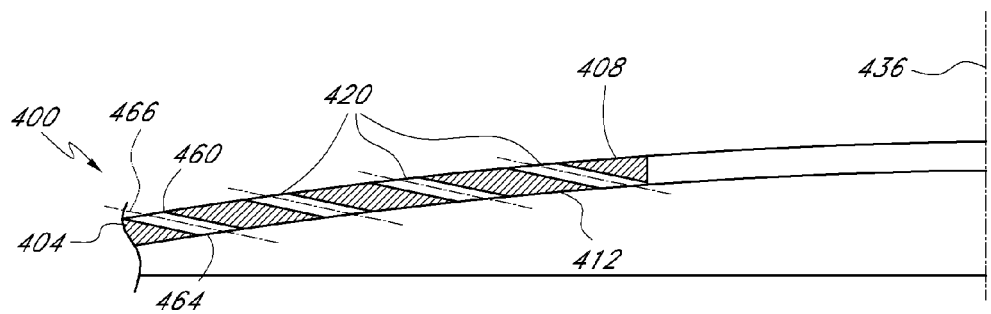
FIG. 44B is a cross-sectional view similar to FIG. 44A of another embodiment of a mask.

FIG. 44B shows a mask 400 that is similar to the mask 100 except as described differently below. The mask 400 can be made of any of the materials discussed herein. The mask 400 can be formed by any suitable process, such as those discussed below in connection with FIGS. 48*a*-48*d* and with variations of such processes. The mask 400 includes a body 404 that has an anterior surface 408 and a posterior surface 412. The mask 400 also includes a nutrient transport structure 4316 that, in one embodiment, includes a plurality of holes 420. The holes 420 are formed in the body 404 so that nutrient transport is provided but transmission of radiant energy (e.g., light) to the retinal locations adjacent the fovea through the holes 404 is substantially prevented. In particular, the holes 404 are formed such that when the eye with which the mask 1000 is coupled is directed at an object to be viewed, light conveying the image of that object that enters the holes 420 cannot exit the holes along a path ending near the fovea.

In one embodiment, each of the holes 420 has a hole entrance 460 and a hole exit 464. Each of the holes 420 extends along a transport axis 466. The transport axis 466 is formed to substantially prevent propagation of light from the anterior surface 408 to the posterior surface 412 through the holes 420. In one embodiment, at least a substantial number of the holes 420 have a size to the transport axis 466 that is less than a thickness of the mask 400. In another embodiment, at least a substantial number of the holes 420 have a longest dimension of a perimeter at least at one of the anterior or posterior surfaces 408, 412 (e.g., a facet) that is less than a thickness of the mask 400. In some embodiments, the transport axis 466 is formed at an angle with respect to a mask axis 436 that substantially prevents propagation of light from the anterior surface 408 to the posterior surface 412 through the hole 420. In another embodiment, the transport axis 466 of one or more holes 420 is formed at an angle with respect to the mask axis 436 that is large enough to prevent the projection of most of the hole entrance 460 from overlapping the hole exit 464.

In one embodiment, the hole 420 is circular in cross-section and has a diameter between about 0.5 micron and about 8 micron and the transport axis 466 is between 5 and 85 degrees. The length of each of the holes 420 (e.g., the distance between the anterior surface 408 and the posterior surface 412) is between about 8 and about 92 micron. In another embodiment, the diameter of the holes 420 is about 5 micron and the transport angle is about 40 degrees or more. As the length of the holes 420 increases it may be desirable to include additional holes 420. In some cases, additional holes 420 counteract the tendency of longer holes to reduce the amount of nutrient flow through the mask 400.

Figure 44C:
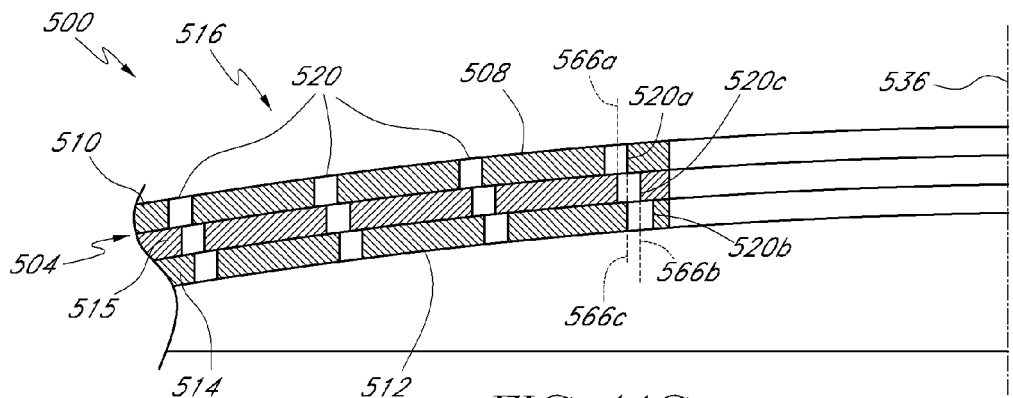
FIG. 44C is a cross-sectional view similar to FIG. 44A of another embodiment of a mask.

FIG. 44C shows another embodiment of a mask 500 similar to the mask 100, except as described differently below. The mask 500 can be made of any of the materials discussed herein. The mask 500 can be formed by any suitable process, such as those discussed below in connection with FIGS. 48*a*-48*d* and with variations of such processes. The mask 500 includes a body 504 that has an anterior surface 508, a first mask layer 510 adjacent the anterior surface 508, a posterior surface 512, a second mask layer 514 adjacent the posterior surface 512, and a third mask layer 515 located between the first mask layer 510 and the second mask layer 514. The mask 500 also includes a nutrient transport structure 516 that, in one embodiment, includes a plurality of holes 520. The holes 520 are formed in the body 504 so that nutrient are transported across the mask, as discussed above, but transmission of radiant energy (e.g., light) to retinal locations adjacent the fovea through the holes 520 is substantially prevented. In particular, the holes 520 are formed such that when the eye with which the mask 500 is coupled is directed at an object to be viewed, light conveying the image of that object that enters the holes 520 cannot exit the holes along a path ending near the fovea.

In one embodiment, at least one of the holes 520 extends along a non-linear path that substantially prevents propagation of light from the anterior surface to the posterior surface through the at least one hole. In one embodiment, the mask 500 includes a first hole portion 520*a* that extends along a first transport axis 566*a*, the second mask layer 514 includes a second hole portion 520*b* extending along a second transport axis 566*b*, and the third mask layer 515 includes a third hole portion 520*c* extending along a third transport axis 566*c*. The first, second, and third transport axes 566*a*, 566*b*, 566*c* preferably are not collinear. In one embodiment, the first and second transport axes 566*a*, 566*b* are parallel but are off-set by a first selected amount. In one embodiment, the second and third transport axes 566*b*, 566*c* are parallel but are off-set by a second selected amount. In the illustrated embodiment, each of the transport axes 566*a*, 566*b*, 566*c* are off-set by one-half of the width of the hole portions 520*a*, 520*b*, 520*c*. Thus, the inner-most edge of the hole portion 520*a* is spaced from the axis 536 by a distance that is equal to or greater than the distance of the outer-most edge of the hole portion 520*b* from the axis 536. This spacing substantially prevents light from passing through the holes 520 from the anterior surface 508 to the posterior surface 512.

In one embodiment, the first and second amounts are selected to substantially prevent the transmission of light therethrough. The first and second amounts of off-set may be achieved in any suitable fashion. One technique for forming the hole portions 520*a*, 520*b*, 520*c* with the desired off-set is to provide a layered structure. As discussed above, the mask 500 may include the first layer 510, the second layer 514, and the third layer 515. FIG. 44C shows that the mask 500 can be formed with three layers. In another embodiment, the mask 500 is formed of more than three layers. Providing more layers may advantageously further decrease the tendency of light to be transmitted through the holes 490 onto the retina. This has the benefit of reducing the likelihood that a patient will observe or otherwise perceive a pattern that will detract from the vision benefits of the mask 500. A further benefit is that less light will pass through the mask 500, thereby enhancing the depth of focus increase due to the pin-hole sized aperture formed therein.

In any of the foregoing mask embodiments, the body of the mask may be formed of a material selected to provide adequate nutrient transport and to substantially prevent negative optic effects, such as diffraction, as discussed above. In various embodiments, the masks are formed of an open cell foam material. In another embodiment, the masks are formed of an expanded solid material.

As discussed above in connection with FIGS. 45B and 45C, various random patterns of holes may advantageously be provided for nutrient transport. In some embodiment, it may be sufficient to provide regular patterns that are non-uniform in some aspect. Non-uniform aspects to the holes may be provided by any suitable technique.

In a first step of one technique, a plurality of locations 220' is generated. The locations 220' are a series of coordinates that may comprise a non-uniform pattern or a regular pattern. The locations 220' may be randomly generated or may be related by a mathematical relationship (e.g., separated by a fixed spacing or by an amount that can be mathematically defined). In one embodiment, the locations are selected to be separated by a constant pitch or spacing and may be hex packed.

In a second step, a subset of the locations among the plurality of locations 220' is modified to maintain a performance characteristic of the mask. The performance characteristic may be any performance characteristic of the mask. For example, the performance characteristic may relate to the structural integrity of the mask. Where the plurality of locations 220' is selected at random, the process of modifying the subset of locations may make the resulting pattern of holes in the mask a "pseudo-random" pattern.

Where a hex packed pattern of locations (such as the locations 120' of FIG. 45A) is selected in the first step, the subset of locations may be moved with respect to their initial positions as selected in the first step. In one embodiment, each of the locations in the subset of locations is moved by an amount equal to a fraction of the hole spacing. For example, each of the locations in the subset of locations may be moved by an amount equal to one-quarter of the hole spacing. Where the subset of locations is moved by a constant amount, the locations that are moved preferably are randomly or pseudo-randomly selected. In another embodiment, the subset of location is moved by a random or a pseudo-random amount.

In one technique, an outer peripheral region is defined that extends between the outer periphery of the mask and a selected radial distance of about 0.05 mm from the outer periphery. In another embodiment, an inner peripheral region is defined that extends between an aperture of the mask and a selected radial distance of about 0.05 mm from the aperture. In another embodiment, an outer peripheral region is defined that extends between the outer periphery of the mask and a selected radial distance and an inner peripheral region is defined that extends between the aperture of the mask and a selected radial distance from the aperture. In one technique, the subset of location is modified by excluding those locations that would correspond to holes formed in the inner peripheral region or the outer peripheral region. By excluding locations in at least one of the outer peripheral region and the inner peripheral region, the strength of the mask in these regions is increased. Several benefits are provided by stronger inner and outer peripheral regions. For example, the mask may be easier to handle during manufacturing or when being applied to a patient without causing damage to the mask.

In another embodiment, the subset of locations is modified by comparing the separation of the holes with minimum and/or maximum limits. For example, it may be desirable to assure that no two locations are closer than a minimum value. In some embodiments this is important to assure that the wall thickness, which corresponds to the separation between adjacent holes, is no less than a minimum amount. As discussed above, the minimum value of separation is about 20 microns in one embodiment, thereby providing a wall thickness of no less than about 20 microns.

In another embodiment, the subset of locations is modified and/or the pattern of location is augmented to maintain an optical characteristic of the mask. For example, the optical characteristic may be opacity and the subset of locations may be modified to maintain the opacity of a non-transmissive portion of a mask. In another embodiment, the subset of locations may be modified by equalizing the density of holes in a first region of the body compared with the density of holes in a second region of the body. For example, the locations corresponding to the first and second regions of the non-transmissive portion of the mask may be identified. In one embodiment, the first region and the second region are arcuate regions (e.g., wedges) of substantially equal area. A first areal density of locations (e.g., locations per square inch) is calculated for the locations corresponding to the first region and a second areal density of locations is calculated for the locations corresponding to the second region. In one embodiment, at least one location is added to either the first or the second region based on the comparison of the first and second areal densities. In another embodiment, at least one location is removed based on the comparison of the first and second areal densities.

The subset of locations may be modified to maintain nutrient transport of the mask. In one embodiment, the subset of location is modified to maintain glucose transport.

In a third step, a hole is formed in a body of a mask at locations corresponding to the pattern of locations as modified, augmented, or modified and augmented. The holes are configured to substantially maintain natural nutrient flow from the first layer to the second layer without producing visible diffraction patterns.

Reduction of Visible Diffraction Patterns Produced by Ophthalmic Devices

Perforating a corneal inlay to provide nutrient transport can have the disadvantage that light also passes through the holes. Light transmission can reduce the opacity of the annulus to the point of degrading the optical performance of the inlay in some conditions. In dim light conditions for distance vision, increased light transmission through the annulus can increase the overall optical performance by increasing illumination of the retina. While this light may help with distance vision in dim conditions, it may decrease the quality of near vision. Therefore, it is desirable to limit the transmission of light while enhancing transmission of nutrients.

The inventors recognized that while nutrient transport through the cornea is largely in the posterior-anterior direction, nutrients also can flow laterally around edges of an inlay. Lateral flow of nutrients can be driven by a gradient of concentration, for example. Thus, even if an impermeable barrier is positioned in a small portion of the cornea, the tissue above the barrier benefits from lateral diffusion, and is not as nutrient-depleted as it would be without lateral diffusion. The closer a region of corneal tissue is to an edge of a nutrient barrier, the less at risk this tissue is to nutrient depletion. Accordingly, an inlay need not have as many perforations at locations near edges as may be at locations farther from edges. Conversely, depletion is at its greatest in the center of a nutrient barrier. Accordingly, there is an advantage to increasing porosity near the center of a nutrient barrier to compensate for the relatively lower lateral flow of nutrients in that central region. Thus, the inlay can be optimized to maintain the health of the cornea.

Figure 52:
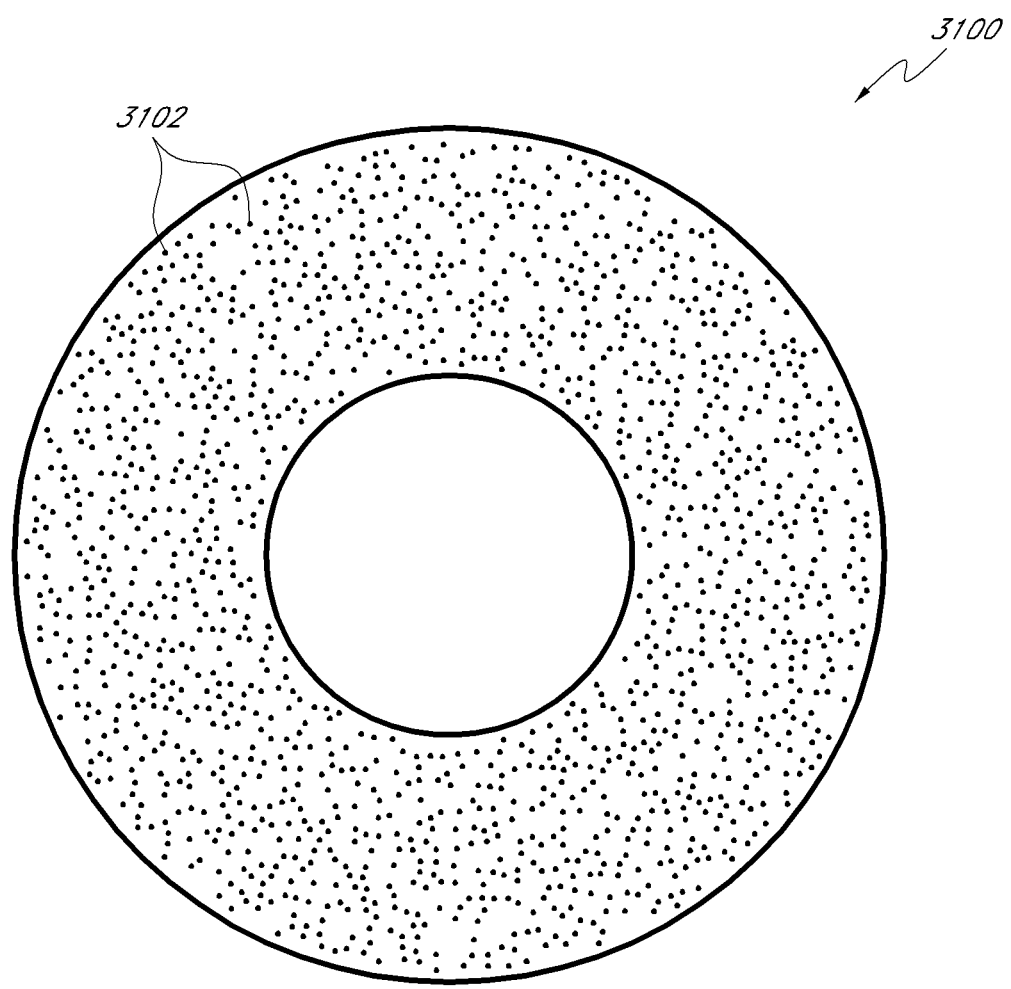
FIG. 52 is a front view of an embodiment of a mask with a plurality of generally randomly distributed holes that have substantially equal size as described herein.

It is possible to design a hole pattern which transmits less light overall, but provides better nutrient transport where it is needed most by creating a gradient of porosity that increases toward a central region of a nutrient blocking structure of an inlay. For example, an arrangement can be provided in which a gradient of porosity is least at the edges and greatest in a central section of an annulus of an inlay. Increasing porosity can be accomplished in a number of ways. For example, FIG. 52 illustrates an annular corneal inlay 3100 with holes 3102 providing porosity, the holes 3102 being generally randomly arranged, the holes 3102 having substantially the same diameter across the annulus. This pattern could be modified to have a greater number of holes toward a central region of the annulus in some embodiments. While the number of holes toward the central region can be increased, the generally random positioning of the holes is maintained in some embodiments to prevent the holes from producing visible diffraction patterns or other optical artifacts.

Other embodiments may be provided that vary at least one aspect of a plurality of holes to reduce the tendency of the holes to produce visible diffraction patterns or patterns that otherwise reduce the vision improvement that may be provided by a mask with an aperture or opening. For example, in one embodiment, the hole size, shape, and orientation of at least a substantial number of the holes may be varied randomly or may be otherwise non-uniform. The mask may also be characterized in that at least one of the hole size, shape, orientation, and spacing of a plurality of holes is varied to reduce the tendency of the holes to produce visible diffraction patterns. In certain embodiments, the tendency of the holes to produce visible diffraction patterns is reduced by having a plurality of the holes having a first hole size, shape, or spacing and at least another plurality of the holes with a second hole size, shape, or spacing different from the first hole size, shape, or spacing. In other embodiments, the mask is characterized in that at least one of the hole size, shape, orientation, and spacing of a substantial number of the plurality of holes is different than at least one of the hole size, shape, orientation, and spacing of at least another substantial number of the plurality of holes to reduce the tendency of the holes to produce visible diffraction patterns. In further embodiments, the holes are positioned at irregular locations. For example, the holes are positioned at irregular locations to minimize the generation of visible artifacts due to the transmission of light through the holes.

Figure 53:
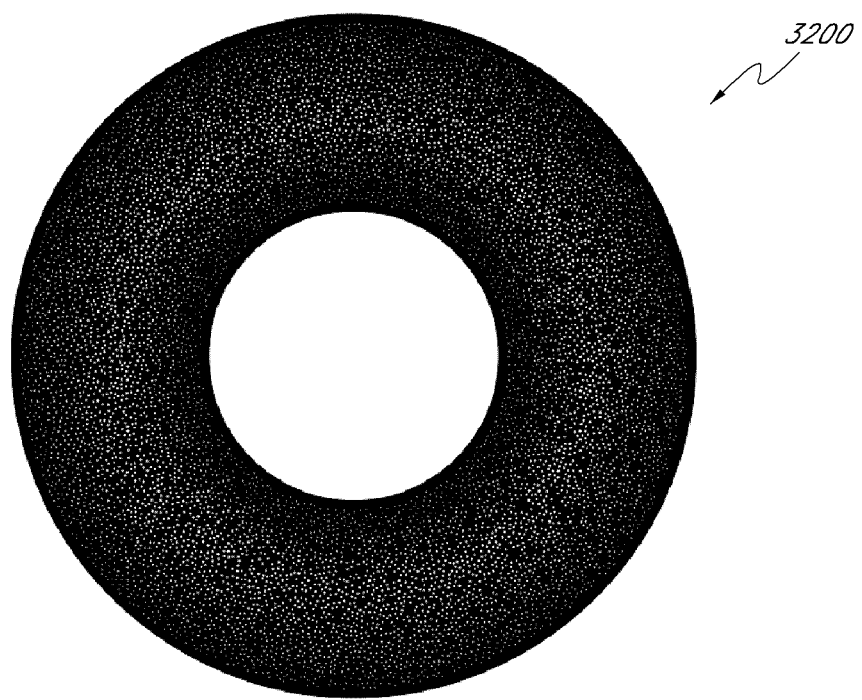
FIG. 53 is a front view of an embodiment of a mask with larger holes near the center of the annulus as described herein.

FIG. 53 illustrates an annular corneal inlay with holes providing porosity for nutrient transport, the holes being generally randomly arranged. The holes in the embodiment of FIG. 53 are not substantially the same hole diameter across the annulus. Rather, the holes have different hole diameters in different regions of the mask. For example, as discussed in greater detail below, the holes have larger diameters in a central region of the inlay than near the inner and outer circumferences of the inlay to enhance porosity of the inlay toward the central region. Additional hole patterns and arrangements optimized for nutrient flow are discussed in U.S. Pat. No. 7,628,810, U.S. Patent Publication No. 2006-0113054, and U.S. Patent Publication No. 2006-0265058, the entirety of each of which is hereby incorporated by reference.

The mask illustrated in FIG. 52 has an irregular hole pattern with holes that are substantially the same size. In one embodiment, the holes have a diameter of about 10 microns. The embodiment of the mask illustrated in FIG. 53 has an irregular hole pattern. The mask includes an inner peripheral region neighboring (e.g., immediately adjacent to) the inner periphery of the mask, an outer peripheral region neighboring (e.g., immediately adjacent to) the outer periphery of the mask, and a plurality of annular bands between the inner periphery region and the outer periphery region. The bands can be modified such that there is a generally increasing porosity from at least one of the inner or outer periphery regions toward a central portion of the annulus. For example, in one arrangement, a fixed number of holes is located in each band, with the size of the holes being larger in bands closer to the center of the annulus than in bands that are farther from the center of the annulus.

Figure 54:
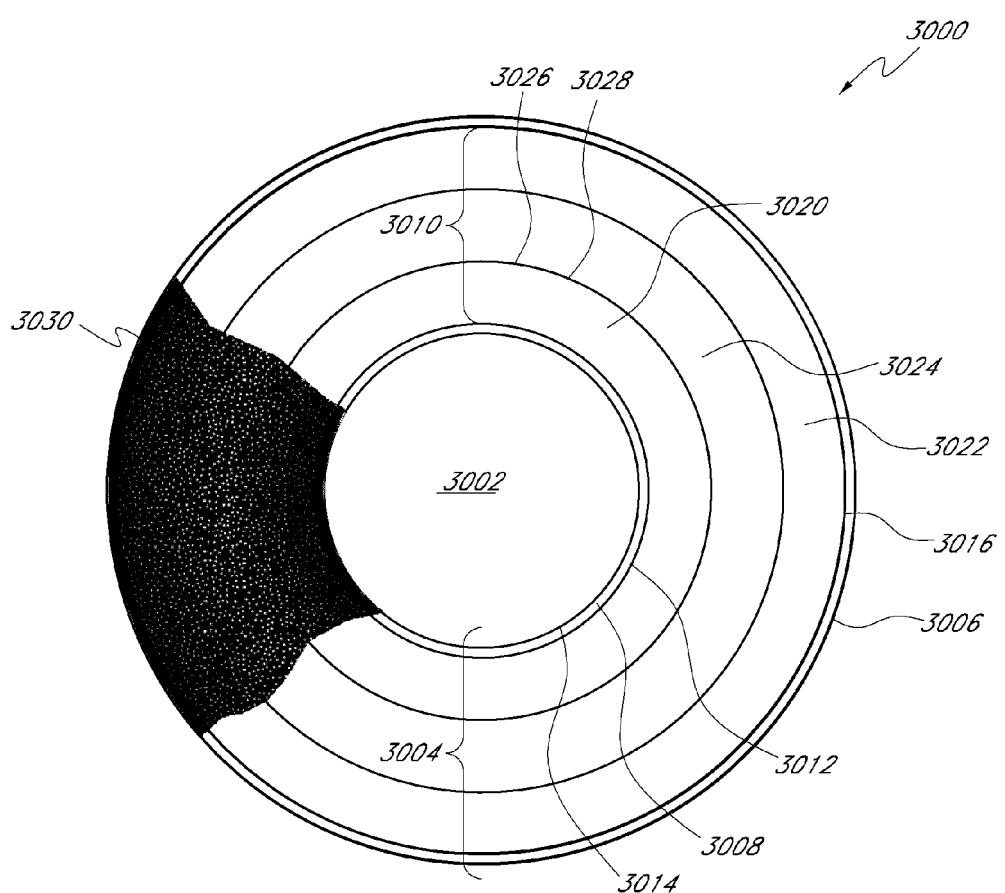
FIG. 54 is a front view of an embodiment of a mask with a hole region that has three sub-regions as described herein.

FIG. 54 illustrates an embodiment of a mask 3000 that includes a body 3004 with an aperture or opening 3002. The body 3004 includes a hole region 3010 between an outer periphery 3012 and an inner periphery 3014 of the body 3004. The hole region 3010 includes a nutrient transport structure 3030. Only a portion of the nutrient transport structure 3030 is shown for simplicity. The hole region 3010 can include two more sub-regions, and each sub-region includes a plurality of holes. Each sub-region can have at least one property that is different from at least one property of another sub-region. For example, properties of a sub-region can include average or mean hole size (radius, diameter, area, perimeter, etc.), number of holes per unit area (e.g., hole density), area of holes per unit area (e.g., percentage of sub-region area that includes holes), shape of the holes, spacing between holes, percentage of light transmission, percentage of nutrient depletion, nutrient transport rate (e.g., nutrient transport rate per unit area), or porosity. FIG. 54 illustrates one embodiment with three sub-regions including an inner region 3020, an outer region 3022, and a central region 3024 between the inner region 3020 and the outer region 3022. The inner region 3020 is located between the inner periphery 3014 and a selected first circumference 3026, the outer region 3022 is located between the outer periphery 2012 and a selected second circumference 3028, and the central region is located between the selected first circumference 3026 and the selected second circumference 3028. Each of the sub-regions can have an area that is the same or different from an area of another sub-regions. For example, each sub-region may or may not be equally spaced radially from the center of the aperture. In certain embodiments, each sub-region is an annular band.

As discussed previously, the body 3004 may also include an inner peripheral region 3008 and/or an outer peripheral region 3006 that are substantially devoid of holes. The inner peripheral region 3008 can extend between the inner periphery 3014 and a selected inner circumference 3018, and the outer peripheral region 3006 can extend between the outer periphery 3012 and a selected outer circumference 3016.

Nutrient depletion can be greatest near the center of the annulus (e.g., about midway between the outer periphery 3012 and the inner periphery 3014. Therefore, more hole area or porosity that allows nutrient transport through the mask 3000 near the center of the annulus can decrease nutrient depletion caused by the mask 3000. In certain embodiments, the central region 3024 has a greater ability to transport nutrients than the inner region 3020 and/or the outer region 3022. For example, the central region 3024 has a central area and the plurality of holes in the central region 3024 may comprise a first percentage of the central area. Similarly, the inner region 3020 has an inner area and the plurality of holes in the inner region 3020 may comprise a second percentage of the inner area, and the outer region 3022 has an outer area and the plurality of holes in the outer region 3022 may comprise a third percentage of the outer area. The first percentage can be greater than the second percentage and/or the third percentage. In another example, the central region 3024 may include a first porosity, the inner region 3020 may include a second porosity, the outer region 3024 may include a third porosity, and the first porosity is greater than the second porosity and/or the third porosity. In other words, the central region 3024, the inner region 3020, and the outer region 3022 can include a nutrient transport property that improves nutrient transport through the mask 3000. The central region 3024 can include a first nutrient transport property value, the inner region 3020 can include a second nutrient transport property value, the outer region 3022 can include a third nutrient transport property value, and the first nutrient transport property value can be greater than the second and/or third nutrient transport property value. The nutrient transport property can be, for example, porosity, hole percentage, hole size, number of holes per unit area, or nutrient transport rate.

The position of the sub-regions can have a variety of configurations. In certain embodiments, the central region is located at between about 10 to about 90 percent of the annular width of the mask from the inner periphery. In additional embodiments, the central region is located at between about 20 to about 60 percent, between about 30 and about 50 percent, or between about 30 and 40 percent of the annular width of the mask from the inner periphery.

The hole region 3010 may also include more than three regions (e.g., inner, outer, and central regions) that are described above. The hole region 3010 can include any number of regions from two to infinity. For example, the hole region 3010 can gradually change one or properties radially across the mask body 3004 and may not change in a step fashion. In one embodiment, the porosity increases and then decreases radially from the inner periphery to the outer periphery. For example, the porosity may be substantially zero at or near the inner periphery and gradually increase to a maximum porosity and then gradually decrease to be substantially zero at or near the outer periphery.

In one arrangement, as illustrated in FIG. 53, ten annular bands are disposed between the inner periphery region and the outer periphery region. The first band of the ten annular bands neighbors (e.g., is immediately adjacent to) the inner periphery region, the second band neighbors the first band, and so forth. The tenth band neighbors the outer periphery region. Each band includes 840 holes in one embodiment. The inner periphery region and outer periphery region can take any suitable form, but preferably include no holes. The radial width of the size of inner periphery region and outer periphery region can be any suitable width, for example optimized to maintain the mechanical integrity of the inlay or to provide for handling by a user. In one embodiment, the inner periphery region and outer periphery region are 50 about microns wide. In some embodiments, only one of the inner periphery region and outer periphery region is provided. In other words, one of the bands with holes can be located at the inner periphery or the outer periphery.

One embodiment is further described in Table I. Each of the bands has a band width, a percentage of light transmission through the band, and a hole diameter for the holes in the band, as illustrated in Table I. In the embodiment of Table I, the bands are configured to be of equal area, and thus have progressively smaller widths farther from the inner periphery of the inlay. However, annular bands can be provided with different areas between the inner periphery and the outer periphery in some embodiments.

Table I

Properties of one embodiment of the inlay of FIG. 53.

| Band No. | Hole Diameter (microns) | % Transmission | Band Width (microns) |
| --- | --- | --- | --- |
| 1 | 5.45 | 2.3 | 146 |
| 2 | 7.45 | 4.3 | 127 |
| 3 | 9.45 | 6.9 | 114 |
| 4 | 11.45 | 10.2 | 105 |
| 5 | 10.45 | 8.5 | 97 |
| 6 | 9.45 | 6.9 | 91 |
| 7 | 8.45 | 5.6 | 86 |
| 8 | 7.45 | 4.3 | 81 |
| 9 | 6.45 | 3.2 | 78 |
| 10 | 5.45 | 2.3 | 74 |

In some embodiments, the central portion of the light blocking portion of the inlay (e.g., a midline of the annulus) is farthest from a source of lateral nutrient flow. In such an embodiment, it may be desirable to locate the portion (e.g., the band) of greatest porosity at or around the central portion. In other embodiments, the peak porosity can be located between the mid-line of the annulus and the inner periphery. In some applications of a small aperture inlay, lateral flow emanating from the aperture at the inner periphery of the inlay and propagating outward through corneal tissue anterior and/or posterior of the annulus is expected to be less than lateral flow emanating from tissue radially outward of the outer periphery and propagating inward through corneal tissue anterior and/or posterior of the annulus. In one embodiment, the location of peak porosity is at about 40 percent or less of the annular width of the inlay from the inner periphery. Such an arrangement provides a higher percentage of total nutrient flow to tissue anterior and/or posterior of an inner portion of the annulus from the nutrient flow structure than is provided to similar tissue adjacent to an outer portion of the annulus.

In the embodiment of the inlay of FIG. 53 described by Table I, the modeled average light transmission is about 5%. In the embodiment of the inlay of FIG. 52, the modeled average light transmission is about 6.75%. The inlays of FIGS. 52 and 53 have an inner radius of 0.8 mm (e.g., an aperture with a diameter of 1.6 mm), and an outer radius of 1.9 mm (e.g., radial distance from the center of the aperture to the outer periphery of the inlay.

Figure 55:
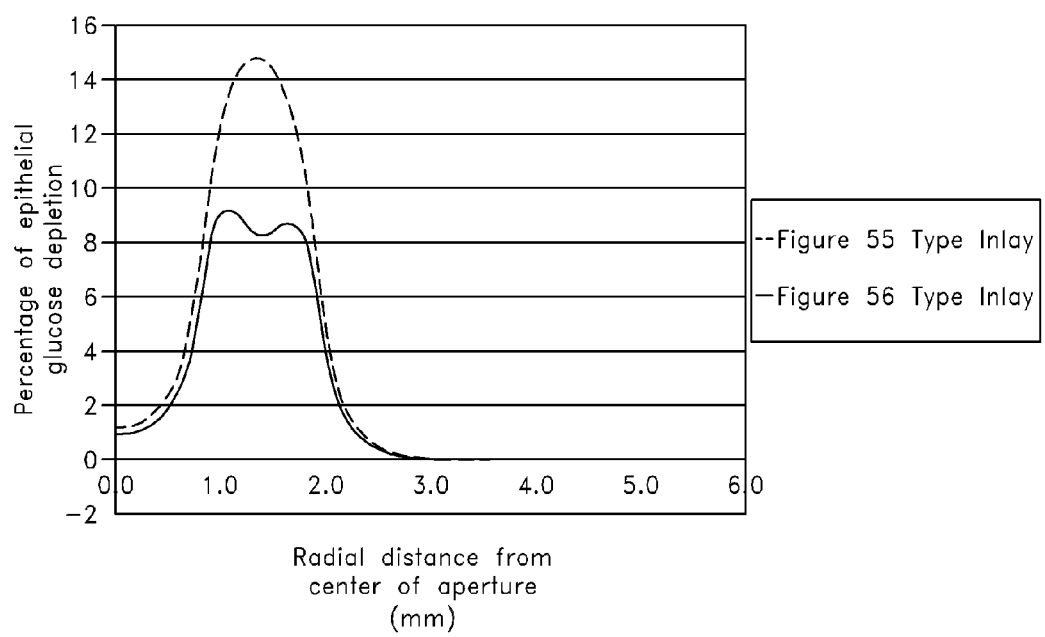
FIG. 55 is a plot of radial distance from the center of the aperture as a function of percentage of epithelial glucose depletion for the masks of FIGS. 52 and 53.

FIG. 55 illustrates a comparison of modeled glucose depletion in a cornea in which the inlays of FIGS. 52 and 53 have been implanted as a function of radial distances from the center of the inlay or aperture. FIG. 55 was obtained from a finite-element model of glucose transport in the human cornea. The inlays of FIGS. 52 and 53 extend from the inner periphery at a radial distance of 0.8 mm to the outer periphery at a radial distance of 1.9 mm. The radial distance from the center of the aperture plotted in FIG. 55 starts at 0 mm (e.g., center of the aperture) and goes to greater than 1.9 mm (e.g., greater than the outer periphery of the inlay). From FIG. 55, it is clear that increasing the porosity, in this case, by increasing the size of holes near the annulus midline, can reduce glucose depletion. In particular, FIG. 55 shows that the embodiment of FIG. 53 reduces depletion of glucose while at the same time decreasing the overall porosity or hole density from 6.75% to 5%. The reduced light transmission of the mask of FIG. 53 compared to the mask of FIG. 52 improves the visual acuity produced by the mask. Therefore, advantageously, the mask of FIG. 53 has both improved nutrient transport and visual acuity compared to the mask of FIG. 52.

Material Bridging an Ophthalmic Device

As discussed above, the mask can include a plurality of holes. Lens body material can extend at least partially through the holes, thereby creating a bond (e.g. material "bridge") between the lens body portion on either side of the mask.

The holes 120 of the mask 100 shown in FIG. 43 may be located anywhere on the mask 100. Substantially all of the holes can be in one or more regions of a mask. The holes 120 of FIG. 43 extend at least partially between the anterior surface 108 and the posterior surface 112 of the mask 100. Each of the holes 120 can include a hole entrance 160 and a hole exit 164. The hole entrance 160 is located adjacent to the anterior surface 108 of the mask 100. The hole exit 164 is located adjacent to the posterior surface 112 of the mask 100. Each of the holes 120 can extend the entire distance between the anterior surface 108 and the posterior surface 112 of the mask 100. Further details about possible hole patterns are described in WO 2011/020074, filed Aug. 13, 2010, which is incorporated by reference in its entirety.

The mask 100 can include an annular region near the outer periphery 124 of the mask having no holes. In certain embodiments, there are no holes within 0.1 mm of the outer periphery 124 of the mask 100.

The mask can include an annular region around the inner periphery of the mask having no holes. In certain embodiments, there are no holes within 0.1 mm of the aperture 128.

Figure 56:
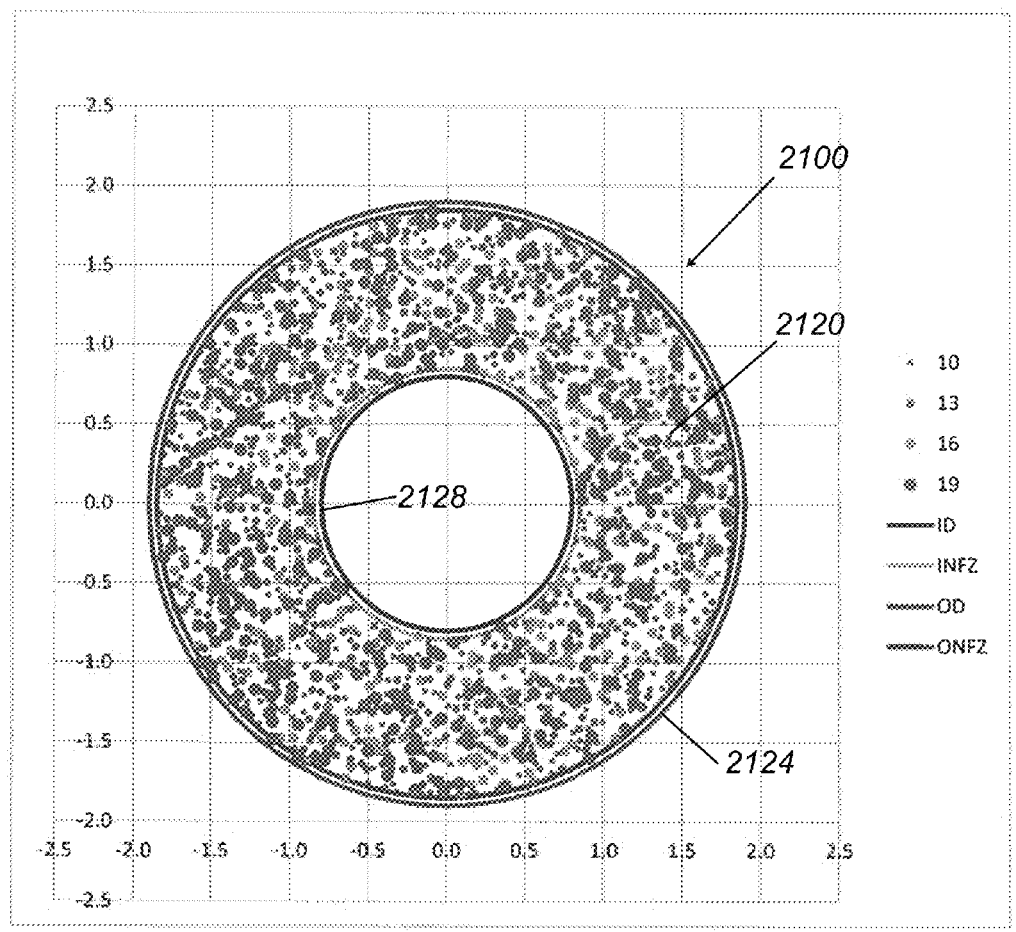
FIG. 56 is a graphical representation of one arrangement of holes of a plurality of holes that may be formed in an ophthalmic device.

As shown in FIG. 56, the mask 2100 can include a plurality of holes 2120. In some embodiments, the holes 2120 each have a same diameter or one or more different diameters. In some embodiments, the holes 2120 can include at least four different diameter.

The diameter of any single hole 2120 is at least about 0.01 mm and/or less than or equal to about 0.02 mm. In some embodiments, the diameter of the holes 2120 can include one or more of the following hole diameters: 0.010 mm, 0.013 mm, 0.016 mm, and/or 0.019 mm.

There are at least about 1000 holes and/or less than or equal to about 2000 holes. In some embodiments, there are at least about 1000 holes and/or less than or equal to about 1100 holes. In some embodiments, there are about 1040 holes. In some embodiments, there are an equal number of holes of each diameter. In some embodiments, the number of holes having each diameter is different.

The holes can be dispersed throughout at least a portion of the mask 2100. The holes are dispersed at irregular locations and/or evenly dispersed randomly throughout a hole region of the mask 2100.

The hole region can be the entire mask 2100 or only a portion of the mask 2100 and include a plurality of sub-regions. The surface area of combined sub-regions is the same as the surface area of the hole region or the sub-regions can overlap each other. Each sub-region can be the same shape and/or cover the same surface area of the hole region, or each sub-region can have a different shape and/or different size.

The holes can be randomly dispersed such that two hole sizes having the same diameter are not located within the same sub-region of the hole region. Also, The holes can be randomly dispersed across a hole region to substantially minimize the appearance diffraction patterns. The hole sizes can be evenly dispersed such that the integrity of the bond between the lens body portions on either side of the mask is substantially constant across the mask.

The plurality of holes 2120 can include at least two different hole sizes. Each sub-region of the hole region can include one hole having each hole size. The number of holes in each sub-region can be the same as the number of different hole diameters. The holes can be randomly dispersed within each subregion, such that the position of the holes in a first sub-region is different from the position of the holes in a second sub-region.

The plurality of holes 2120 can include four different hole sizes. Each sub-region of the hole region can include four holes, each of the holes having a different diameter.

Intraocular Implants with Reduced Thickness

The natural lens of an eye is often replaced with an intraocular lens when the natural lens has been clouded over by a cataract. An intraocular lens may also be implanted into the eye to correct other refractive defects without removing the natural lens. The intraocular implant can include any of the mask embodiments discussed herein. The intraocular implants may be implanted in the anterior chamber or the posterior chamber of the eye. In the posterior chamber, the implants may be fixated in the ciliary sulcus, in the capsular bag, or anywhere an intraocular implant is fixated. The intraocular lenses can have a reduced thickness in a central region compared to conventional intraocular lenses. The reduced thickness in the central region can help improve implantation of the intraocular lens.

Several alternatives to fixed-focus IDLs have been developed, including multifocal IDLs and accommodating IDLs that attempt to provide the ability to see clearly at both distance and near. Multifocal IDLs do provide good acuity at both distance and near, but these lenses typically do not perform well at intermediate distances and are associated with glare, halos, and night vision difficulties associated with the presence of unfocused light. Accommodating IDLs of several designs have also been developed, but none so far has been able to replicate the function of the natural crystalline lens. IDLs with apertures have been described by Vorosmarthy (U.S. Pat. No. 4,976,732). These devices, however, do not attempt to change focus from far to near, but merely attempt to reduce the blurry image from defocus to a level where a presbyopic emmetrope can read. Notably, Vorosmarthy did not address the issue of reducing thickness of a masked IOL for application in small-incision surgery.

The masked IOL can include a thinner optic than has been known in the art. The advantage to a thinner optic is that the IOL can be inserted through a smaller incision into the eye. Since corneal incisions tend to distort the cornea and impair vision, reducing the size of the incision will improve the quality of vision. The optic is made thinner by means similar to a Fresnel lens, where alternating concentric zones provide focusing power and height steps. While the thickness reduction possible with a Fresnel lens is significant, the height steps are optically inappropriate for clinical application. They do not focus light to an image at the fovea, but instead scatter light, leading to dysphotopsias (streaks, shadows, halos, etc.) in the patient's vision. By combining Fresnel-type height steps with a mask that blocks light from passing through the steps and allows light to pass only through the focusing surfaces, one can eliminate the dysphotopsias associated with a common Fresnel lens, obtaining the benefit of reduced thickness without introducing unwanted optical effects.

Generally, intraocular implants are implanted into the eye by rolling up an intraocular implant and inserting the rolled up intraocular implant into a tube. The tube is inserted into an incision in the eye, and the intraocular implant is ejected out of the tube and deployed within the eye. Intraocular implants can be implanted within the lens capsule after removal of the natural lens, or in the anterior chamber, posterior chamber, and can be coupled with or attached to the ciliary sulcus (sometimes referred to herein as "sulcus-fixated"). Depending on the location of the intraocular implant within the eye, dimensions of the intraocular implant, including but not limited to the aperture of the mask, may be adjusted. By reducing the thickness of in the central region of the intraocular lens, the intraocular lens can be rolled up tighter and inserted into a smaller tube. A smaller incision can be made in the eye if a smaller tube is used. The result is a less invasive procedure with quicker recovery time for the patient. Also, compared with a conventional posterior chamber phakic intraocular lens, a reduced thickness lens that is fixated in the ciliary sulcus will allow more space between the intraocular lens posterior surface and the natural crystalline lens surface, thereby reducing the potential for contact between these surfaces.

The intraocular lens 4100 can include a lens body 4102 with an optical power to refract light and correct refractive errors of the eye. The intraocular lens 100 may include one or more haptics 4104 to prevent the intraocular lens 4100 from moving or rotating within the eye. As used herein the term "haptic" is intended to be a broad term encompassing struts and other mechanical structures that can be apposed against an inner surface of an eye and mounted to a lens structure to securely position a lens in an optical path of an eye. The haptics 4104 can be a variety of shapes and sizes depending on the location the intraocular lens 4100 is implanted in the eye. Haptics illustrated in FIGS. 57-66 can be interchanged with any variety of haptic. Haptics may be C-shaped, J-shaped, plate design, or any other design. An intraocular implant described herein may have two, three, four, or more haptics. The haptics may be of open or closed configuration and may be planar, angled, or step-vaulted. Examples of haptics are disclosed in U.S. Pat. Nos. 4,634,442; 5,192,319; 6,106,553; 6,228,115; Re. 34,251; 7,455,691; and U.S. Patent Application Publication 2003/0199978, which are incorporated in their entirety by reference.

Figure 57B:
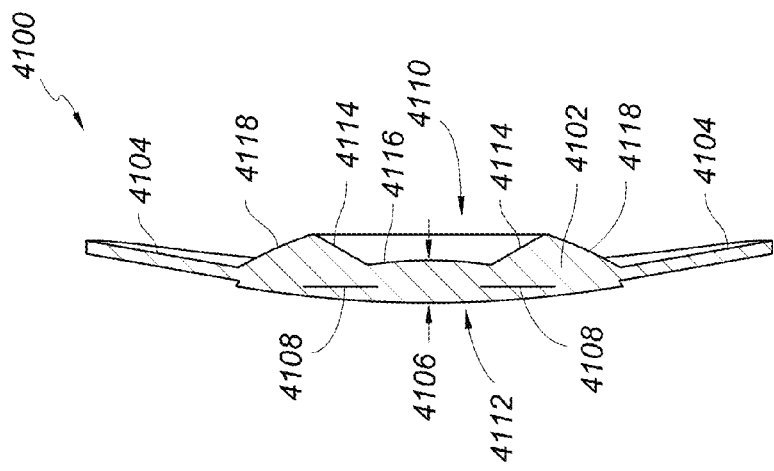
FIG. 57B illustrates a cross-sectional view of the intraocular lens of FIG. 57A.
Figure 57A:
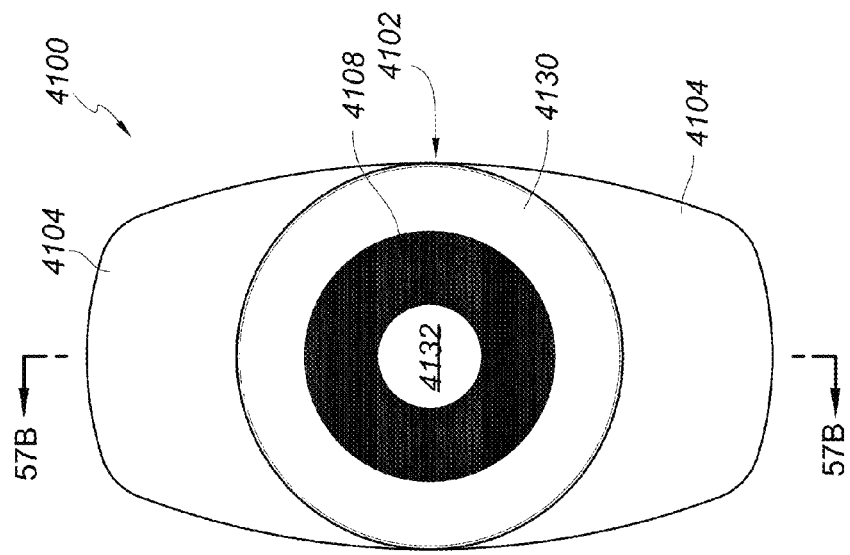
FIG. 57A illustrates a front plan view of an embodiment of an intraocular lens with a recessed central region on the posterior surface as described herein.

The lens body 4102 can include a posterior surface 4110 and an anterior surface 4112, as illustrated in FIGS. 57A-B. The lens body 4102 includes a first portion 4116 (e.g., inner portion or central region), a second portion 4114 (e.g., transition zone) and a third portion 4118 (e.g., outer portion or region) on the posterior surface 4110. The second portion 4114 can be between and/or adjacent the first portion 4116 and the third portion 4118. The second portion 4114 can substantially surround the first portion 4116, and the third portion 4118 can substantially surround the second portion 4114. The first portion 4116 can be substantially circular, and the second portion 4114 and third portion 4118 can be substantially annular. The first portion 4116 and third portion 4118 can refract light or have an optical power to improve a patient's vision. The second portion 4114 has one or more facets, grooves, crests, troughs, depressions, contours, surface curvatures, etc. to make the first portion 4116 closer to the anterior surface 4112 than if the posterior surface 4110 did not have the second portion 4114. The second portion 4114 can also be described as a "transition zone" between the first portion 4116 and the third portion 4118. For example, the second portion 4114 transition zone can slope toward the anterior surface 4112 from the third portion 4118 to the first portion 4116. The second portion 4114 transition zone can include a surface substantially perpendicular to the anterior surface 4112. The transition zones are like those incorporated in a Fresnel lens. They enable the lens body to be made thinner than would be required in a conventional lens design. However, as with Fresnel lenses, the transition zones introduce optical aberrations that would not be clinically acceptable in intraocular lenses.

The intraocular lens 4100 can include a mask 4108 that can be positioned to block a substantial portion of light that would pass through the second portion 4114 transition zone of the posterior surface 4110. "Blocked" as used in this context includes preventing at least a portion of light from passing through the mask, as well as preventing substantially all the light from passing through the mask. If the mask 4108 did not block the light rays that would pass through the second portion 4114, aberrations would result since the refraction of light (e.g. optical power, etc.) in the second portion 4114 is typically different than in the first portion 116 and the third portion 4118.

The first portion 4116 can be convex, the second portion 4114 can be concave, and the third portion 4118 can convex. The first portion 4116 and the third portion 4118 can have a positive or converging optical power and the second portion 4114 can have a negative or diverging optical power. The second portion 4114 may have curvature or no curvature in a direction extending radially from the first portion 4116 to the third portion 4118. For example, the second portion 4114 may have a positive or negative curvature (e.g., convex or concave) in a direction extending radially from the first portion 4116 to the third portion 4118. Furthermore, the second portion 4114 may form a closed loop and have surface similar to an outer surface of a frustoconical shape.

In certain embodiments, the first portion 116 is within a central region 132 of the lens body 102. The central region 132 can be recessed within the lens body 102. In certain embodiments, the third portion 118 is within an outer region 130 of the lens body 102. In certain embodiments, an outer perimeter of the first portion 116 is surrounded and/or enclosed by an inner perimeter of the second portion 114. In certain embodiments, an outer perimeter of the second portion 114 is surrounded and/or enclosed by an inner perimeter of the third portion 118. In certain embodiments, the maximum thickness of the lens body 102 in the region of the first portion 116 is less than the maximum thickness of the lens body 102 in the region of the second portion 114.

A lens body 4202 can include a first portion 4222, a second portion 4220 and a third portion 4224 on the anterior surface 4212, as illustrated in FIGS. 58A-B. The first portion 4222, the second portion 4220 and the third portion 4224 on the anterior surface 4212 can have similar features as described above for the first portion 4116, the second portion 4114 and the third portion 4118 on the anterior surface 4112. The intraocular lens 4200 can include a mask 4208 that is positioned to block a substantial portion of light that passes through the second portion 4220 of the anterior surface 4212.

Both an anterior surface 4312 and a posterior surface 4310 can have a first portion 4316, 4322, a second portion 4314, 4320 and a third portion 4318, 4324, as illustrated in FIGS. 59A-B. A mask 4308 can be positioned so that a substantial portion of the light that passes through the second portion 4320 of the anterior surface 4312 and the light that would pass through the second portion 4314 of the posterior surface 4310 will be blocked by the mask 4308.

The mask can be coupled with the second portion, which is concave. For example, the mask can be located adjacent the second portion. The mask can be attached to the posterior surface, the anterior surface, the posterior and the anterior surfaces, within the lens body, or between the posterior surface and the anterior surface. The radial width or the area of the mask can be about the same as the radial width or the area of the second portion. The mask can extend at least partially into the area of the first portion and/or the third portion of the lens body. By extending the mask into the first portion and/or the third portion, the mask can block light that enters at large angles off the optical center axis of the lens body and that may then pass through the second portion.

Illustrated in FIGS. 60A-B, an intraocular lens 4400 can further include a fourth portion 4420*b* and a fifth portion 4424*b* on the anterior surface 4412 and/or the posterior surface 4410. The fourth portion 4420*b* is adjacent the third portion 4424*a* and can substantially surround the third portion 4424*a*. The fifth portion 4424*b* is adjacent the fourth portion 4420*b* and can substantially surround the fourth portion 4420*b*. The fourth portion 4420*b* can have similar features as described above for the second portion 4420*a*, and the fifth portion 4424*b* can have similar features as described above for the third portion 4424*a*. The intraocular lens 4400 can include a first mask 4408*a* that is positioned to block a substantial portion of light that passes through the second portion 4420*a* of the anterior surface 4412, and a second mask 4408*b* that is positioned to block a substantial portion of light that passes through the fourth portion 4420*b* of the anterior surface 4412. It should be understood that additional pairs of portions with a mask like the fourth portion 4420*b*, the fifth portion 4424*b* and the second mask 4408*b* can be further included in an intraocular lens.

FIGS. 61A-B illustrate an intraocular lens 4500 similar to the intraocular lens 4400 illustrated in FIGS. 60A-B. Instead of the intraocular lens 4400 having a first mask 4408*a* and a second mask 4408*b*, the intraocular lens 4500 has a single mask 4508 with a plurality of light transmission holes that allow at least partial light transmission through the mask 4508. The light transmission holes can be configured to allow substantially no light that passes through the second portion 4520*a* and the fourth portion 4520*b* to pass through the mask 4508, but allow at least some light that passes through the third portion 4524*a* to pass through the mask 4508. For example, a middle annular region of the mask can have a plurality of holes to allow at least some light to pass through the mask, and an inner annular region and an outer annular region can have substantially no holes. Light transmission structures or holes are further discussed in sections below and can be applied to embodiments discussed herein.

The variety of intraocular lenses described herein are designed to suit the vision correction needs of particular patients. For example, for patients with relatively small pupils, dim light may present more of a vision issue than for patients with larger pupils. For smaller pupil patients, a mask with more light transmission and/or a smaller outer diameter will increase the amount of light that reaches the retina and may improve vision in dim light situations. Conversely, for larger pupil patients, less light transmission and/or a larger outer diameter mask may improve low-contrast near vision and block more unfocused light. The masked IDLs described herein give the surgeon flexibility to prescribe the appropriate combination of masked IOL features for particular patients.

Figures 63A, 63B:
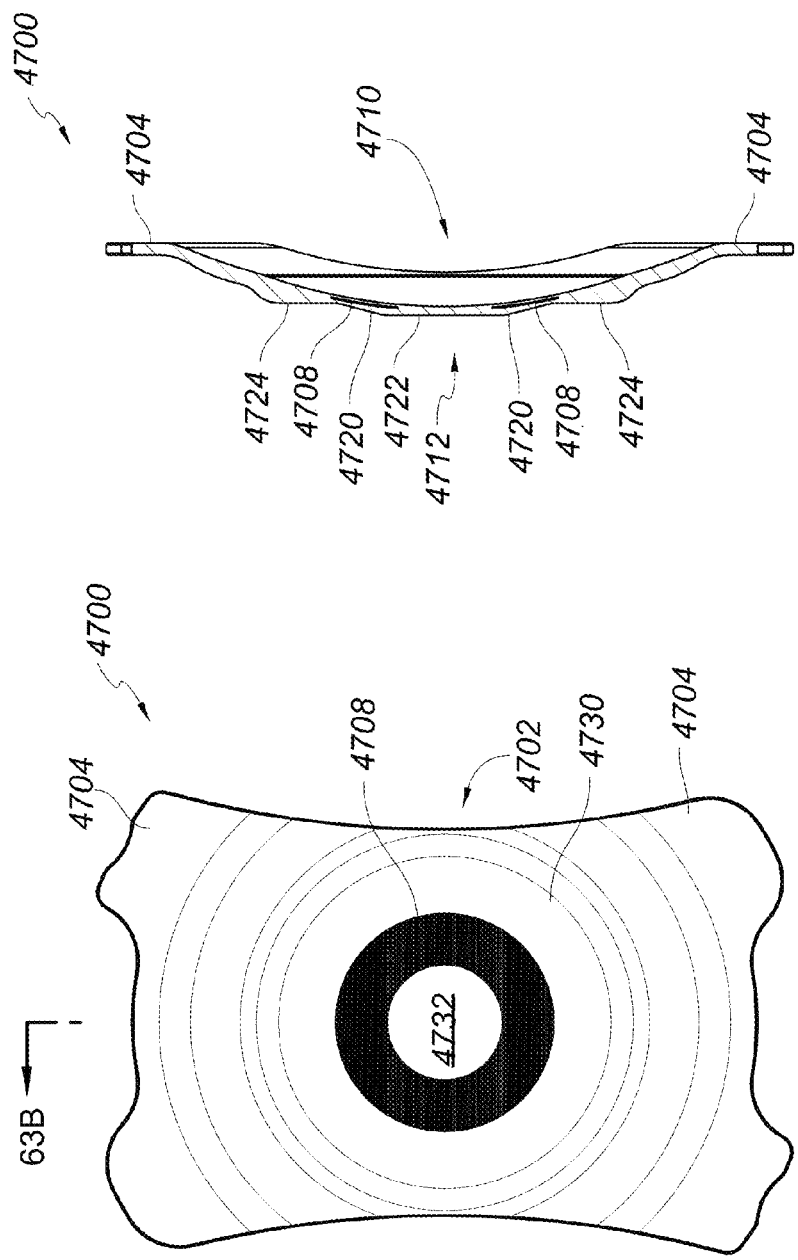
FIG. 63A illustrates a front plan view of an embodiment of an intraocular lens with a concave posterior surface and a negative optical power as described herein.
FIG. 63B illustrates a cross-sectional view of the intraocular lens of FIG. 63A.

FIGS. 62-63 illustrate intraocular lenses 4600, 4700. The posterior surface and anterior surface of an intraocular lens can have a variety of curvatures. For example, the posterior surface and/or the anterior surface can be concave or convex. FIGS. 62A-B illustrates an intraocular lens 4600 with a concave posterior surface 4610 with an anterior surface 4612 to create a positive optical power lens. FIGS. 63A-B illustrate an intraocular lens 4700 with a concave posterior surface 4710 with an anterior surface 4712 to create a negative optical power lens. Both intraocular lenses 4600, 4700 have a second portion 4620, 4720 to reduce the overall thickness of the intraocular lenses 4600, 4700. Both intraocular lenses 4600, 4700 also can include a mask 4608, 4708 to block light that passes through the second portion 4620, 4720. For negative power intraocular lenses, such as the intraocular lens 4700 of FIG. 63, the thickness of the central region 4732 of the lens body 4702 may not be reduced by the second portion 4720. However, the thickness of the outer region 4730 of the lens body 4702 can be reduced by the second portion 4720 (e.g., transition zone). Advantageously, if an intraocular lens has a positive optical power or a negative optical power, the thickness of at least a portion of the lens body can be reduced by having the lens body include a second portion.

Tables II and III illustrate examples of intraocular lens with reduced lens body thicknesses. The column labeled "Reduced" corresponds to an intraocular lens with a second portion (e.g. transition zone), and the column labeled "Original" is corresponds to an intraocular lens without a second portion. The optic diameter is the diameter of the outer-most portion of the lens body with an optical power. The reduction percentage of the center region thickness indicated in Tables II and III can be about proportional to the reduction in the possible rolled up diameter of a reduced thickness IOL. Therefore, the reduction percentage of the center region thickness indicated in Tables II and III can also be about proportional to the reduction in the incision size that can be used during implantation of the IOL in a patient. An IOL is rolled up and inserted into a tube, and the tube is inserted into the incision. The IOL can then be deployed into the intraocular space of the eye. The IOL is often rolled up as tight as possible so that open space (e.g., voids) is minimized in a cross-section of the tube at a location where the implant body has the greatest cross-sectional area that is generally parallel with the optical axis of the implant body. Therefore, the cross-sectional area of the tube is greater than or equal to the greatest cross-sectional area of the implant body that is generally parallel with the optical axis of the implant body. For example, a 36% reduction in the cross sectional area of the implant body could reduce the cross sectional area of the tube by 36% or could reduce the diameter of the tube by about 20%. A minimum incision length is generally one-half of the circumference of the tube. Therefore, a 36% reduction in the cross sectional area of the implant body can result in about 20% reduction in incision length. For example, a 1.8 mm incision could be reduced to about 1.44 mm. A smaller incision is beneficial because it avoids post-operative astigmatism.

TABLE II

EXAMPLES OF REDUCED THICKNESS IOLS WITH POSITIVE OPTICAL POWER.

| Optic Diameter [mm] | Material [Ref. index] | Diopter | Center region thickness [mm] | | | Cross section area of center region [mm$^2$] | | |
|---|---|---|---|---|---|---|---|---|
| | | | Original | Reduced | Reduction [%] | Original | Reduced | Reduction [%] |
| Biconvex IOL | | | | | | | | |
| 5.5 | 1.4300 | 18.0 | 0.94 | 0.42 | 55 | 3.96 | 2.48 | 37 |
| 5.5 | 1.4300 | 24.0 | 1.20 | 0.56 | 53 | 4.93 | 3.13 | 37 |
| 5.5 | 1.4583 | 18.0 | 0.77 | 0.32 | 58 | 3.32 | 2.05 | 38 |
| 5.5 | 1.4583 | 24.0 | 0.96 | 0.42 | 56 | 4.02 | 2.51 | 38 |
| 6.0 | 1.4300 | 18.0 | 1.08 | 0.50 | 54 | 4.76 | 3.08 | 35 |
| 6.0 | 1.4300 | 24.0 | 1.40 | 0.62 | 56 | 6.04 | 3.85 | 36 |
| 6.0 | 1.4583 | 18.0 | 0.87 | 0.37 | 57 | 3.92 | 2.50 | 36 |
| 6.0 | 1.4583 | 24.0 | 1.10 | 0.50 | 55 | 4.88 | 3.13 | 36 |
| Sulcus-fixated IOL | | | | | | | | |
| 5.5 | 1.4583 | 5.0 | 0.34 | 0.15 | 56 | 1.75 | 1.22 | 30 |
| 5.5 | 1.4583 | 10.0 | 0.52 | 0.20 | 62 | 2.43 | 1.51 | 38 |
| 6.0 | 1.4583 | 5.0 | 0.37 | 0.17 | 54 | 1.95 | 1.36 | 30 |
| 6.0 | 1.4583 | 10.0 | 0.59 | 0.21 | 64 | 2.86 | 1.76 | 38 |

TABLE III

EXAMPLES OF REDUCED THICKNESS IOLS WITH NEGATIVE OPTICAL POWER.

| Optic Diameter [mm] | Material [Ref. index] | Diopter | Outer region thickness [mm] | | | Cross section area of outer region [mm 2] | | |
|---|---|---|---|---|---|---|---|---|
| | | | Original | Reduced | Reduction [%] | Original | Reduced | Reduction [%] |
| Sulcus-fixated IOL | | | | | | | | |
| 5.5 | 1.4583 | −5.0 | 0.26 | 0.17 | 35 | 1.09 | 0.77 | 29 |
| 5.5 | 1.4583 | −10.0 | 0.41 | 0.25 | 39 | 1.52 | 0.97 | 36 |
| 6.0 | 1.4583 | −5.0 | 0.29 | 0.20 | 31 | 1.12 | 0.77 | 31 |
| 6.0 | 1.4583 | −10.0 | 0.48 | 0.32 | 33 | 1.57 | 0.99 | 37 |

Figure 64:
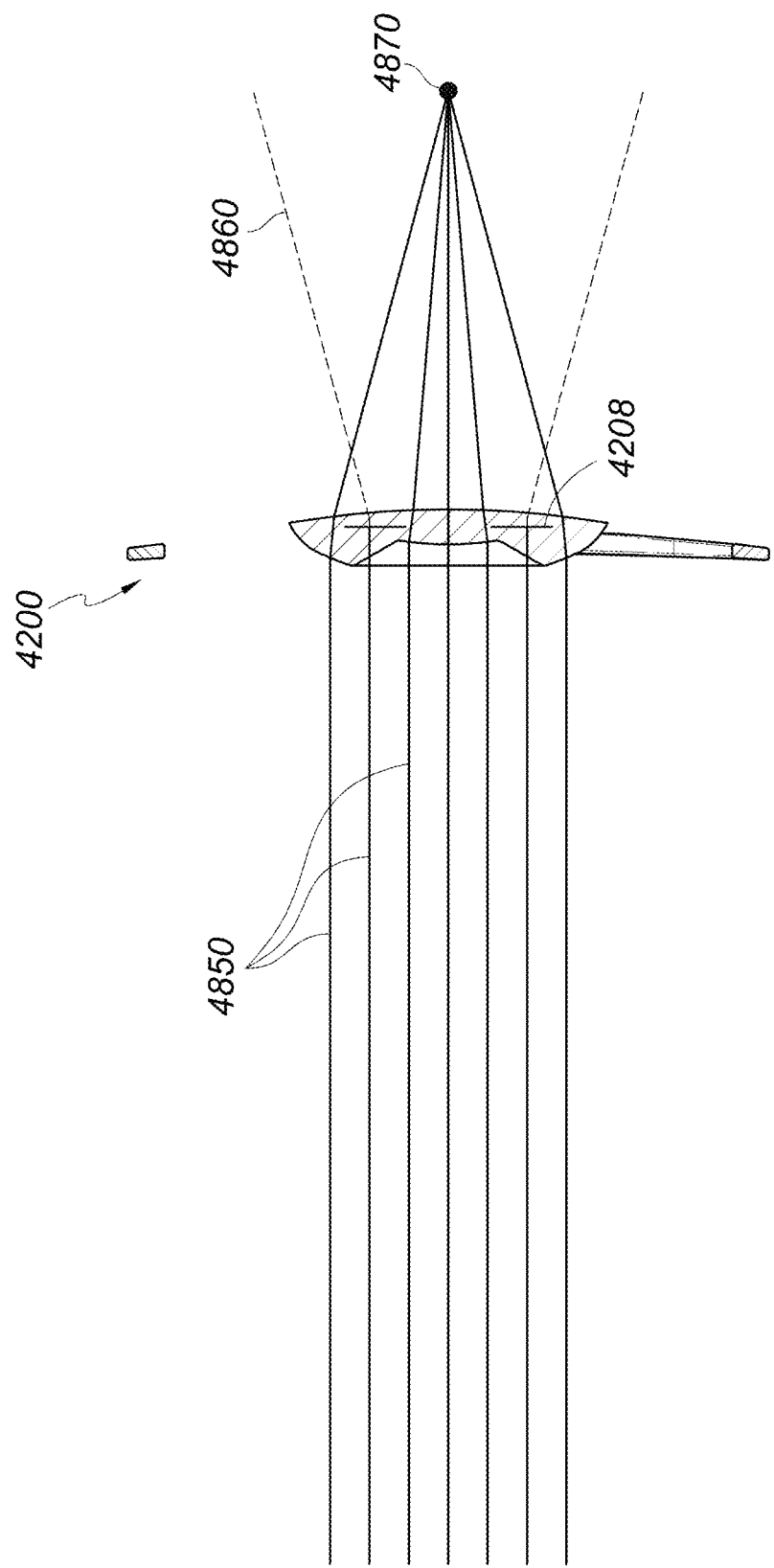
FIG. 64 is a cross-sectional schematic representation of light passing through the intraocular lens of FIG. 64B.

FIG. 64 illustrates the operation of the intraocular lens 4200 of FIGS. 58A-B. In use, light enters the anterior surface 4212, passes through the lens body 4202 and exits the posterior surface 4210 of the intraocular lens 4200. The mask 4208 is located such that the mask 4208 blocks a substantial portion of the light rays 4850 that pass through the second portion 4220 of the anterior surface 4212, as illustrated in FIG. 64. If the mask 4208 did not block the light rays 4850 that pass through the second portion 4220, aberrations would result. For example, if the curvature of the second portion 4220 is configured to provide a negative or divergent optical power, light rays 4860 passing through this region would diverge and not focus, as illustrated in FIG. 64. The light rays 4850 that pass through the first portion 4222 and/or the third portion 4224 would have a positive or convergent optical power. If the first portion 4222 and the third portion 4224 have a similar curvature or optical power, light rays 4450 entering the anterior surface 4212 and passing through the first portion 4222 and/or the third portion 4224 would converge at a common point 4870 after passing through the posterior surface 4210, as illustrated in FIG. 64. FIG. 65A illustrates an intraocular lens 4200 implanted within the capsular bag 4954 of an eye 4952. Parallel light rays 4950 that pass through the intraocular lens 4200 converge on the retina 4956.

The lens body 4202 can include one or more materials. The lens body 4202 can include two or more materials. For example, the first portion 4222 and the third portion 4224 can include different materials. If the materials selected for the first portion 4222 and the third portion 4224 have different refractive indexes, the curvature of the first portion 4222 and the third portion 4224 can be different to obtain a similar optical power (e.g. dioptric power) for both portions.

Generally, the optical power of an intraocular lens is selected for focusing on far objects. A natural lens can deform to change the focal distance for far and near viewing. Conventional artificial intraocular lenses are generally unable to change the focal distance. For example, an eye that is presbyopic or where an artificial intraocular lens has an optical power for farther distance, light rays that enter the eye and pass through the cornea and the natural lens or artificial intraocular lens converge at a point behind or in front of the retina and do not converge at a point on the retina. The light rays strike the retina over a larger area than if the light rays converged at a point on the retina. The patient experiences this as blurred vision, particularly for up-close objects such as when reading. For such conditions, the mask 4208 of the intraocular lens 4200 can be configured with an aperture such that only a subset of light rays, e.g. a central portion, are transmitted to the retina. The mask 4208 with an aperture can improve the depth of focus of a human eye. For example, the aperture can be a pin-hole aperture. The mask 4208 blocks a portion of the outer light rays resulting in more focused light rays. The mask 4208 can include an annular region surrounding an aperture. The aperture can be substantially centrally located on the mask. For example, the aperture can be located around a central axis of the mask, also referred to as the optical axis of the mask. The aperture of the mask can be circular or any other shape.

The mask 4208 can be positioned in a variety of locations in or on the intraocular lens 4200. The mask 4208 can be through the lens body 4202. The mask 4208 can be positioned on the anterior or posterior surface of the lens body 4202 or embedded within the lens body. For example, the mask 4208 can be positioned substantially at the midway line between the posterior and anterior surfaces of the lens body 4202, between the midway line and the posterior surface of the lens body 4202, or between the midway line and the anterior surface of the lens body 4202. The mask 4208 can be positioned midway, one-third or two-thirds between the midway line and the posterior surface of the lens body 4202, or the mask can be positioned midway, one-third or two-thirds between the midway line and the anterior surface of the lens body 4202. If the transition zone is on the anterior surface of the implant body and the mask is positioned to be on or near the surface of the transition zone on the anterior surface, the mask may not extend beyond the transition zone since light even at large angles from the optical axis that hits or passes through the transition zone surface would be blocked by the mask.

The mask 4208 of an intraocular lens 4200 can include an aperture wherein the mask blocks a portion of the light to improve viewing near objects, similar to a mask discussed above. Advantageously, the mask 4208 can provide as an aperture and can block a portion light that may not converging on the retina 4956 and also block light that passes through the second portion 4220, creating aberrations, as described above. In certain embodiments, the aperture of the mask 4208 has a diameter of about 1 to 2 mm. In certain embodiments, the mask 4208 has an outer perimeter with a diameter of about 3 to 5 mm.

Figure 65:
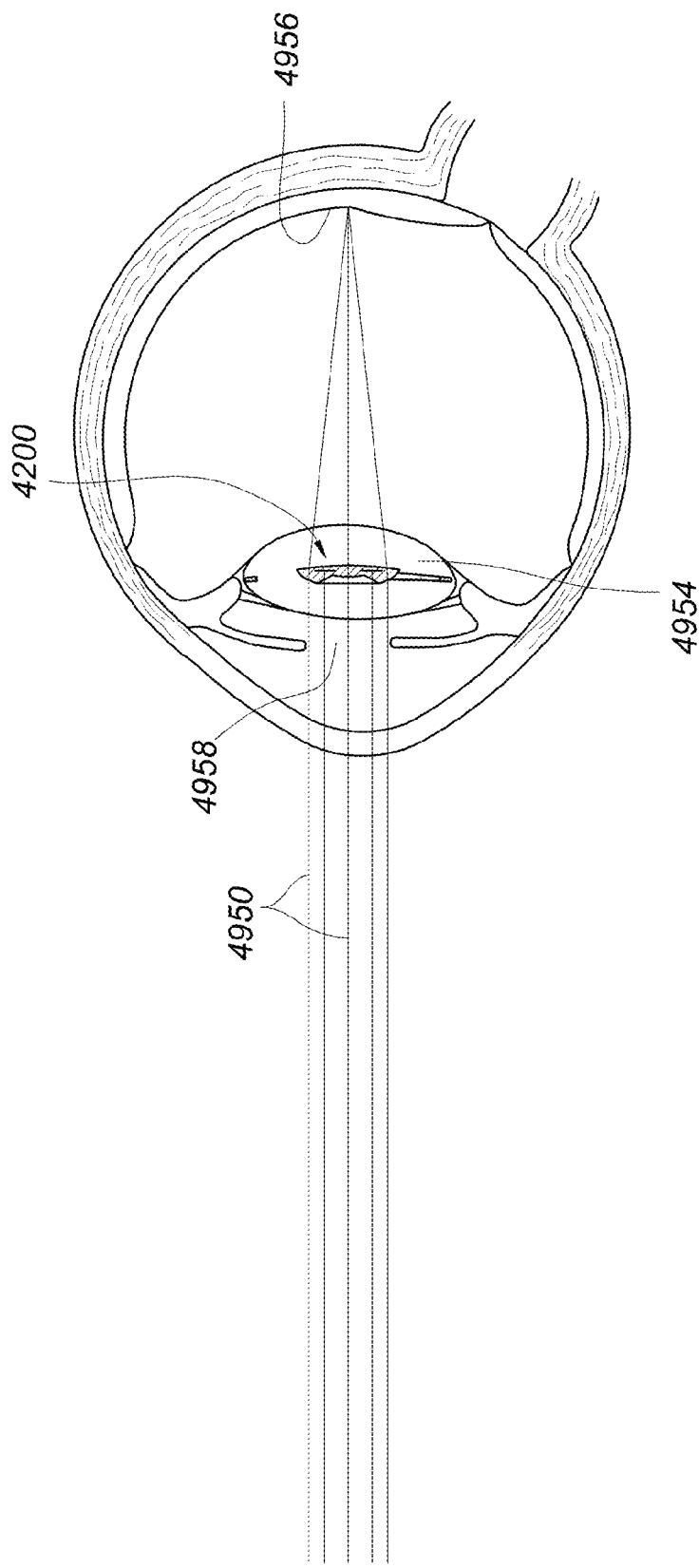
FIG. 65 is a schematic representation of light from a far object transmitted through an eye having an embodiment of an intraocular lens that is in the capsular bag.

The third portion 4224 of intraocular lens 4200 can improve low light vision. As the pupil of the eye enlarges, eventually light rays will enter and pass through the third portion 4224 of the intraocular lens 4200. As illustrated in FIG. 65, if the pupil 4958 of the eye 4952 is large enough so that light rays 4950 pass through the third portion 4224 of the intraocular lens 4200, additional light rays 4950 will strike the retina. As discussed above, the intraocular lens

4200 can have an optical power to correct for viewing far objects so that light rays from a far object are focused at one point on the retina. Near objects during low light conditions may result in an unfocused image if the intraocular lens 4200 has an optical power to view far objects.

The mask 4208 can have different degrees of opacity. For example, the mask 4208 can block substantially all of visible light or may block a portion of visible light. The opacity of the mask 4208 may also vary in different regions of the mask 4208. The opacity of the outer edge and/or the inner edge of the mask 4208 can be less than the central region of the mask 4208. The opacity in different regions may transition abruptly or have a gradient transition. Additional examples of opacity transitions can be found in U.S. Pat. Nos. 5,662,706, 5,905,561 and 5,965,330, which are incorporated in their entirety by reference.

A conventional intraocular lens 5000 is illustrated in FIGS. 66A-B. By having a recessed portion on the posterior surface 4310 (created by second portions 4314) and/or the anterior surface 4312 (created by second portion 4320) of the lens body 4302, the maximum thickness of the intraocular lens 4300 is reduced compared to a conventional lens body 5002 without such portions, as shown in FIG. 66B. The cross-sectional thickness of the lens body 5002 is generally dependent on the optical power of the intraocular lens 5000 and the material of the lens body 5002. In particular, the central region of the lens body 5002 is generally the thickest section of the intraocular lens 5000 with a central region cross-sectional thickness 5006. The lens body 4202 of an intraocular lens 4200 can include a central region thickness 4206 less than the central region thickness 5006 of other common lens bodies. In FIG. 59B, the thickness 4306 is further reduced compared to a conventional intraocular lens 5000.

Generally, as discussed above, intraocular lenses are implanted into the eye by rolling up an intraocular lens and inserting the rolled up intraocular lens into a tube. One advantage to a thinner lens body is that it the intraocular lens can be more tightly rolled up resulting in being able to use a small tube and a small incision. Another advantage to a thinner lens body is that the intraocular lens can decrease risks associated with implanting in different locations within the eye. For example, an intraocular lens 4200 can be implanted within the anterior chamber. An intraocular lens 4200 can also be positioned within the posterior chamber so that the first portion 4216 of the posterior surface 4210 floats above the natural crystalline lens. The potential for contact between the posterior surface 4210 of the intraocular lens 4200 and the natural crystalline lens will be reduced because the reduced thickness of the intraocular lens 4200. For example, the intraocular lens 4200 can be coupled with or attached to the ciliary sulcus (sometimes referred to herein as "sulcus-fixated"). An intraocular lens 4200 can also be implanted in the capsular bag, as illustrated in FIG. 65. Depending on the location of the intraocular lens within the eye, dimensions of the intraocular lens 4200 including but not limited to the aperture of the mask 4208 may be adjusted.

The intraocular lens 4200 and/or the lens body 4202 can be made from one or more materials. For example, the intraocular lens 4200 and/or the lens body 4202 can comprise polymers (e.g. PMMA, PVDF, polypropylene, polycarbonate, PEEK, polyethylene, acrylic copolymers, polystyrene, PVC, polysulfone), hydrogels, and silicone.

Near-Ir Transparent Materials

As used herein, "substantially opaque," "blocking substantially all," or "absorbing substantially all" means blocking or absorbing the transmission of at least about 60%-100% of electromagnetic radiation in the wavelength range or ranges indicated, further including the ranges of at least about 70%-100%, at least about 80%-100%, at least about 90%-100%, and at least about 95%-100%, or any other percentage sufficiently great so as to not impair the depth of focus improvement properties of such masks as are disclosed herein. Also, as used herein, "substantially transparent" or "transmit substantially all" means transmitting or allowing to pass the transmission of at least about 50%-100% of electromagnetic radiation in the wavelength range or ranges indicated, further including the ranges of at least about 60%-100%, at least about 70%-100%, at least about 80%-100%, at least about 90%-100%, at least about 95%-100%, and about 100%, or any other percentage sufficiently great so as to permit NIR imaging of the eye using any NIR imaging modality.

Ocular examination and diagnosis is increasingly performed with non-invasive imaging (e.g., optical coherence tomography, near infrared scanning laser ophthalmoscopes, including GDxPRO™ (Carl Zeiss Meditec), optical coherence tomography (OCT)-based pachymetry, including Visante omni (Carl Zeiss Meditec). In particular, OCT has come to be widely used for examining the retina. OCT has become prevalent in both anterior and posterior segment examination because of its resolution and imaging speed, which together allow accurate and real time 3D imaging of tissues under examination. Most currently available commercial posterior segment OCTs operate in the near infrared (NIR) region of the electromagnetic spectrum. Anterior segment OCTs and future posterior segment OCTs may operate in the range of about 1050 nm to about 1300 nm to allow for greater penetration into the ocular tissue.

Masks, such as those described in U.S. Patent Publication No. 2006/0265058, may be formed of any of a number of ocular compatible materials and biomaterials, including for example polyvinylidene fluoride (PVDF), and may be pigmented with, for example, titanium, gold, or carbon particles to provide opacity. However, such a mask is practically 100% opaque to both visible and NIR light. This application describes ocular devices and methods to incorporate NIR transmission in a mask for an intracorneal inlay, and/or an intraocular lens, or other ophthalmic device. The NIR transmissive material can be incorporated with any mask or intraocular lens embodiment discussed herein. The materials described hereinbelow may be used in lieu of or in conjunction with other visible light-blocking materials in a mask or may be used to form the mask itself, regardless of whether the mask is in the form of a corneal inlay or incorporated into an IOL.

In some embodiments disclosed herein, select bandpass dyes are incorporated into the gross material of the mask or intraocular lens. For example, an orange dye which absorbs only light in the range of about 400-520 nm will allow all other wavelengths to pass, i.e. less than about 400 nm or higher than about 520 nm. Therefore, it is the object of some embodiments to use one or more bandpass dyes with varying absorption spectra to selectively block only predetermined ranges of the electromagnetic radiation spectrum while selectively allowing the transmission of others. This design principle becomes particularly valuable when observing that the currently prevalent ocular imaging modalities of optical coherence tomography, near infrared scanning laser ophthalmoscopes, and optical coherence tomography-based pachymetry rely almost exclusively on NIR light in the range of 1050 to 1300 nm. Therefore, as is discussed below, it is possible to create a mask capable of blocking the transmission of substantially all visible light to provide the benefit of a mask while remaining transparent to the NIR light used in ocular imaging.

Any combination of one or more light absorbing dyes may be used to block a desired spectrum of electromagnetic radiation wavelengths. One method of blocking the visible spectrum of electromagnetic radiation is to take a three-prong approach and use a red dye (to block light from about 500-600 nm), a blue dye (to block light from about 600-700 nm), and a yellow dye (to block light from about 400-500 nm), thereby blocking substantially the entire spectrum of visible light. It is also possible to use bandpass dyes with broader absorption spectra and omit one or more dyes from the three-prong approach. For example, the inventors have found at least one dye composition which uses only an orange dye capable of absorbing (and thereby blocking) electromagnetic radiation in the range of about 400-540 nm and a blue-green dye capable of absorbing (and thereby blocking) electromagnetic radiation in the ranges of about 360-440 nm as well as about 540-700 nm, thereby obviating the need for a yellow dye.

Regarding the use of an orange or red dye to block electromagnetic radiation, any orange or red dye of the azo type or others capable of absorbing electromagnetic radiation may be used. Such an orange or red dye may absorb electromagnetic radiation in the range of about 350-600 nm, including the ranges of about 375-575 nm, about 400-550 nm, about 425-525 nm, and about 450-500 nm, or any other range of wavelengths selected to be used in a tailored composition of dyes to achieve a desired absorption profile. In some embodiments, the orange or red dye absorbs electromagnetic radiation in more than one range, i.e., has more than one lambda max. The red dye may include at least one methacrylate or acrylate moiety or other reactive moiety. Such acrylate or methacrylate or other moieties and possible subsequent covalent bonding, discourages, if not eliminates, a substantial amount of subsequent leaching or release of the dye molecule over time and through extended use. The incorporation of moieties, including but not limited to acrylate and methacrylate moieties, into the dye molecule allows a high degree of covalency and a concomitantly high degree of dye loading. This is particularly useful in ocular devices with particularly thin cross sections as high dye loadings are one technique in these applications to achieve appropriate opacity. At high dye loadings achieving high covalency up to and including 100% may be difficult. As covalency declines, dye bleeding into the surrounding matter can result. For example, dye bleeding into the clear/transparent regions of the IOL or other non-corneal ocular device or, if the device is implanted into the cornea, into the surrounding corneal tissues can occur if covalency is not sufficiently high. Such dye bleeding is highly undesirable in ocular devices. The methacrylated or acrylated dyes disclosed herein may achieve a high degree of covalent bonding sufficient for corneal inlays and other thin cross section ocular devices. These and other similar dyes will be substantially free of dye bleeding associated with insufficient covalency in a thin, high concentration dye structure. Alternatively, in some embodiments the orange dye may be reacted with a polymer after polymerization using reactive functional groups such as methacrylate or acrylate: the dye linker moiety may be grafted to the polymer after polymerization to achieve substantially the same result as discussed above.

In some embodiments, the orange dye used is Disperse Red 1 acrylate, 2-[N-ethyl-4-[(4-nitrophenyl)diazenyl]anilino]ethyl prop-2-enoate. The structure for Disperse Red 1 Acrylate is shown below:

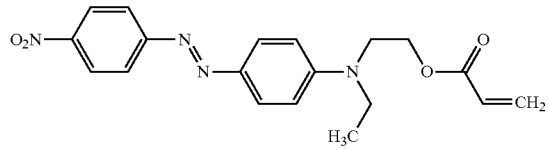

Disperse Red 1 acrylate has a lambda max, or maximum absorbance, at about 480 nm. In other embodiments, any red or orange dye with similar or appropriate absorption spectra or range may be used.

The orange and red dyes mentioned in the immediately preceding paragraphs may be particularly useful for incorporation in hydrophobic ocular biomaterials, many of which are known in the art. Examples of well-known hydrophobic ocular biomaterials include hydrophobic acrylic, silicone elastomer, and PMMA. In an alternative embodiment, it is desirable to use hydrophilic ocular biomaterials, many of which are also known in the art. Examples of well-known hydrophilic ocular biomaterials include hydrophilic acrylic, collagen, silicone hydrogels, and polyvinylpyrolidone. In such embodiments, it may be desirable to use ionic dyes capable of blocking substantially all of the visible spectrum of electromagnetic radiation while allowing transmission of substantially all of the NIR spectrum of electromagnetic radiation (i.e., a red ionic dye, a blue ionic dye, and a yellow ionic dye to therefore block substantially the entire spectrum of visible electromagnetic radiation).

Regarding the use of a blue-green dye to block electromagnetic radiation, any blue-green dye may be used which is capable of absorbing electromagnetic radiation in the range of about 550-700 nm, including the ranges of about 575-675 nm, about 600-650 nm, or any other range of wavelengths selected to be used in a tailored composition of dyes to achieve a desired absorption profile. In some embodiments, the blue-green dye absorbs electromagnetic radiation in more than one range, i.e., has more than one lambda max.

In some embodiments, the blue-green dye used is the dimethacrylate derivative of 1,4-Bis(4-ethylanilino) anthraquinone (a close relative of Solvent Green 3, i.e. 1,4-Bis(4-methylanilino)anthraquinone), formally known as 2-[4-({4-[(4-{2-[(2-methylprop-2-enoyl)oxy]ethyl}phenyl)amino]-9,10-dioxo-9,10-dihydro-anthracen-1-yl}amino)phenyl]ethyl-2-methyl prop-2-enoate. The structure of dimethacrylate derivative of 1,4-Bis(4-ethylanilino) anthraquinone is shown below:

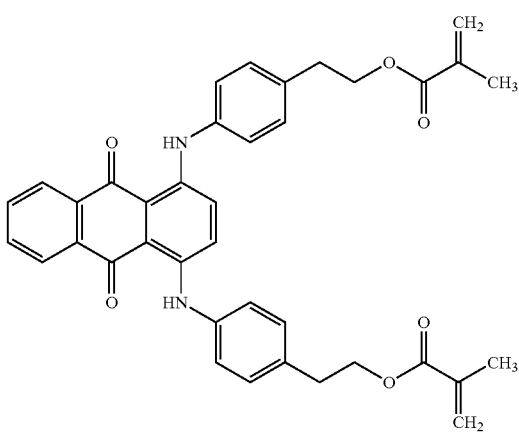 [SMILES: C=C(C)C(=O)OCCc1ccc(Nc2ccc(Nc3ccc(CCOC(=O)C(=C)C)cc3)c3c2C(=O)c2ccccc2C3=O)cc1]

The dimethacrylate of 1,4,-Bis(4-ethylanilino)anthraquinone has lambda max, or maximal absorbance, in the visible spectral range at about 624-644 nm, about 591-611 nm, and about 394-414 nm. Dimethacrylate of 1,4,-Bis(4-ethylanilino)anthraquinone has an additional benefit in creating masks as disclosed in this application because it is bifunctional in that it has two methacrylate functional groups. Because of these two functional groups, the blue-green dye molecule is very efficiently covalently incorporated into a polymeric base material. The incorporation of moieties, including but not limited to acrylate and methacrylate moieties, into the dye molecule allows a high degree of covalency and a concomitantly high degree of dye loading. This is particularly useful in ocular devices with particularly thin cross sections as high dye loadings are one technique in these applications to achieve appropriate opacity. At high dye loadings achieving high covalency up to and including 100% may be difficult. As covalency declines, dye bleeding into the surrounding matter can result. For example, dye bleeding into the clear/transparent regions of the IOL or other non-corneal ocular device or, if the device is implanted into the cornea, into the surrounding corneal tissues can occur if covalency is not sufficiently high. Such dye bleeding is highly undesirable in ocular devices. The methacrylated or acrylated dyes disclosed herein may achieve a high degree of covalent bonding sufficient for corneal inlays and other thin cross section ocular devices. These and other similar dyes will be substantially free of dye bleeding associated with insufficient covalency in a thin, high concentration dye structure. Alternatively, in some embodiments the blue-green dye may be reacted with a polymer after polymerization using reactive functional groups such as methacrylate or acrylate: the dye linker moiety may be grafted to the polymer after polymerization to achieve substantially the same result as discussed above. When grafting the dye linker moiety to the polymer after polymerization, i.e., surface bonding the dye, it may be useful to diffuse dye into the polymer matrix to achieve more complete incorporation and therefore a higher degree of opacity and electromagnetic radiation absorption. Additionally, the molecule's bifunctionality dramatically reduces the required concentration of crosslinking molecule (such as ethylene glycol dimethacrylate) in the final formulation. Below is shown the general structure of a monomeric 1,4,-Bis(alkylarylamino)anthraquinone dye:

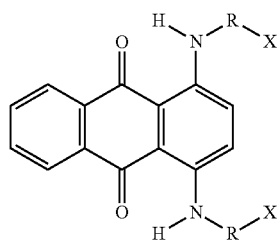

The properties and synthesis of the dimethylacrylate of 1,4,-Bis(4-ethylanilino)anthraquinone are generally described in U.S. Pat. No. 5,055,602, which is incorporated by reference herein in its entirety. In the aforementioned molecule, "R" represents, most generally, an aryl, alkyl or arylalkyl linker with 2 to 12 carbon atoms and "X" represents, most generally, any polymerizable, unsaturated organic functional group (such as a methacrylate, acrylate, vinyl carbonyl, or vinyl carbamate functional moieties). Variations of this molecule in which "R" is an arylalkyl linker may be particularly useful in applications such as those disclosed herein. In some embodiments, the aryl of the arylalkyl linker may be a single aromatic ring. In other embodiments, the aryl group may consist of more than one separate aromatic ring or alternatively it may be one or more fused multiple aromatic ring systems. Additionally, in some embodiments the aryl linker may be bonded directly to the nitrogen of the mother molecule (shown above) as shown below. In other embodiments, the aryl linker, as just disclosed, may be situated between two separate alkyl groups where the proximate alkyl group bonds to the nitrogen of the mother molecule and the distal alkyl group bonds to the carbon of the methacrylate or acrylate via the distal alkyl group's reactive end group. The alkyl group, whether it be only one alkyl group on the distal side of the aryl group or two alkyl groups, one on each of the proximate and distal sides of the aryl group, may be any alkyl group, in linear, branched or ring form, in the range of about 1-15 carbon atoms, including the ranges of about 1-12 carbon atoms, about 1-10 carbon atoms, about 1-8 carbon atoms, about 1-6 carbon atoms, about 1-4 carbon atoms, and about 1-2 carbon atoms, including also only one carbon atom alkyl groups (methylene groups), or any alkyl group or groups which serves to link the mother molecule, through the aryl group, to the methacrylate or acrylate group (on each side of the bilaterally symmetrical mother molecule). In some embodiments the alkyl group distal to the aryl group includes an organic functional moiety that may facilitate bonding to the final distal X group (as mentioned above, in some cases the X group is a methacrylate or acrylate functional group). In some embodiments, additional moieties may be included in the alkyl linkers, for example: oxygen heteroatoms, nitrogen heteroatoms, or sulfur heteroatoms. The addition of such heteroatoms may facilitate other chemistries or impart the added benefit aiding in the control of solubility.

To create the dimethacrylate of 1,4,-Bis(4-ethylanilino) anthraquinone, the R groups are phenyl alkyl linkers and the X groups are methacryl groups, as shown below:

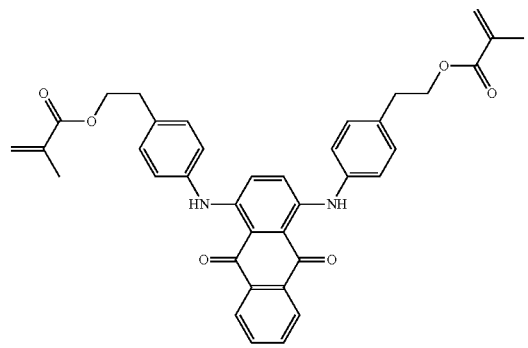

In other embodiments, any green dye with appropriate absorption spectra may be used. More specifically to the aforementioned molecule, the linker (the "R Group" shown above) may be modified while retaining substantially all of the desired absorbance properties of the dye. Some examples of the broad class of phenyl alkyl radicals are listed above. These examples are not intended to limit this disclosure, rather they are illustrative examples of only a few possible linkers. As mentioned above, additional moieties may be included in the alkyl linkers, for example: oxygen heteroatoms, nitrogen heteroatoms, or sulfur heteroatoms.

Additionally, the use of acryl groups instead of methacryl groups (the "X Group" shown above) should have little to no impact on the absorbance properties of the dye molecule. Lastly, a vinyl substituent in place of the acryl or methacryl double bond would efficiently add to the polymer chain via free radical mechanism. There are many additional possible modifications which would not adversely affect the desirable properties of the dye molecules disclosed herein and may therefore be applicable to and used in NIR transmissible masks as disclosed herein. The aforementioned alterations to the dimethacrylate of 1,4, -Bis(4-ethylanilino) are not intended to limit the scope of this application, rather it is understood that such alterations are merely representative of select classes of possible changes that can be made to the molecule without substantial adverse effects on its absorbance properties as would be recognized by those skilled in the art.

In other embodiments, any dye in the classes of dyes known as azo (including monoazo and bisazo) and anthraquinone which when used alone or in concert with other dyes (of its own class or any other class) meets the visible absorption requirements of absorbing substantially the entire visible spectrum of electromagnetic radiation may be used.

An example of the synthesis of the dimethacrylate of 1,4,-Bis(4-ethylanilino)anthraquinone is presented below. The percentages given below and elsewhere herein for formulations are by weight unless stated otherwise.

EXAMPLE 1

Synthesis of the Dimethacrylate of 1,4,-bis(4-ethylanilino)anthraquinone

The dimethacrylate of 1,4,-Bis(4-ethylanilino)anthraquinone: synthetic mixture consisted of Intermediate 5.2%

Intermediate ingredients

| Leucoquinizarin | 23.3% |
| 2-(4-Aminophenyl) Ethanol | 76.7% |
| Ethylene Glycol | excess(to dissolve) |
| Acetone | excess |
| Deionized Water | excess |
| 0.625 M NaOH | excess |

| Dry Acetonitrile | 78.9% |
| Triethanolamine | 10.4% |
| Methacryloyl Chloride | 5.5% |
| Ethylene Glycol | excess (to dissolve) |

The dimethacrylate of 1,4,-bis(4-ethylanilino)anthraquinone (or 2-[4-({4-[(4-{2-[(2-methylprop-2-enoyl)oxy]ethyl}phenyl)amino]-9,10-dioxo-9,10-dihydro-anthracen-1-yl}amino)phenyl]ethyl-2-methyl prop-2-enoate) was synthesized in the following manner. 10 grams of leucoquinizarin and 33 grams of aminophenyl ethanol were stirred under a nitrogen blanket in an oil bath for five hours at 150° C. The chemical mixture was then cooled to 100° C. at which point dry ethylene glycol was added to dissolve the solid and the nitrogen blanket was removed. Air was then bubbled into the mixture and everything was incubated for 6 to 8 hours at 100° C. After incubation, the mixture was dissolved in acetone and filtered. The filtrate was recovered and 0.625M NaOH was added drop-wise to the filtrate resulting in formation of needle-like blue-green precipitate. The precipitate was recovered with filtration and washed with deionized water and dried under vacuum. To each gram of intermediate, 15 grams of dry acetonitrile and 2 grams of triethanolamine were added to dissolve the mixture. 1 mL of methacryloyl chloride was added dropwise to the mixture with continuous stiffing. After mixing for 3 hours at room temperature, ethylene glycol was added to dissolve the crude product. Deionized water was added to the crude product liquor to selectively precipitate the product dimethacrylate of 1,4,-Bis(4-ethylanilino)anthraquinone. After recovering the product with filtration, the product was purified by crystallization from an acetone water mixture. Crystals were collected by filtration and vacuum dried for 6 to 8 hours. The result was the final highly purified product, 2-[4-({4-[(4-{2-[(2-methylprop-2-enoyl)oxy]ethyl}phenyl)amino]-9,10-dioxo-9,10-dihydro-anthracen-1-yl}amino)phenyl]ethyl-2-methyl prop-2-enoate (purity >95% by HPLC).

For the following, all percentages refer to weight percent. To create the intermediate, in some embodiments some parameters may be altered. For example, the 2-(4-aminophenyl)ethanol/leucoquinizarin ratio (by weight) may be used in the range of about 1.1%-5.7%, including the ranges of about 2.1%-4.7%, about 3.1%-3.6% and about 3.3%, or any other concentration of aminophenyl ethanol which allows proper synthesis of the intermediate. In some embodiments the leucoquinizarin and aminophenyl ethanol are mixed under nitrogen blanket. In other embodiments those chemicals may be mixed under any inert or non-reactive gas blanket, including for example helium, neon, argon, krypton, and xenon. In some embodiments the chemical mixture may be cooled to a temperature anywhere in the range of about 70° C.-140° C., including the range of about 95° C.-105° C., and about 100° C. In some embodiments, the gas bubbled into the mixture may be any mixture of oxygen with inert noble gases (helium, neon, argon, krypton, and xenon) or nitrogen. In some yet other embodiments, the deduced intermediate may be oxidized through chemical oxidation: for example by using ozone or hydrogen peroxide. In some embodiments, the NaOH solution may be used in a molarity range of about 0.5-0.7 molar, including the ranges of about 0.54-0.66 molar, about 0.58-0.62 molar, and including about 0.6 molar.

Once the intermediate has been created, certain other parameters may be altered. For example, the intermediate may be used in the range of about 2-12% including the ranges of about 3%-10%, about 4%-8%, about 5%-7% and including about 5.2%. In some embodiments, the dry acetonitrile may be used in the range of about 60%-90%, including the ranges of about 47%-57%, about 50%-54%, and about 78%. Other solvents, specifically those that are non-protic water soluble organic solvents, may be substituted for acetonitrile, including but not limited to: tetrahydrofuran, dimethysulfoxide, and dimethylformamide. Triethanolamine may be used in the range of about 10%-20%, including the range of about 10%-15%, and about 11.5%. Methacryloyl chloride may be used in the range of about 2.5%-8%, including the ranges of about 2.7%-7.5%, about 2.9%-7%, about 2.7%-6.5%, and about 5.5%-5.6%. Other glycols may be substituted for ethylene glycol, such as those liquid polyethylene glycols with a molecular weight less than 400 g/mol, including but not limited to: triethyleneglycol, tetraethylene glycol and pentaethylene glycol. Low molecular weight water miscible alcohols may also be substituted for ethylene glycol, including but not limited to N-butoxyethanol and ethylcellosolve. The time parameters given, including stirring times, drying times, and resting times may be altered to any times which allow the proper chemical or physical reactions to occur.

The blue-green dyes mentioned in the immediately preceding paragraphs may be particularly useful for incorporation in hydrophobic ocular biomaterials, many of which are known in the art. In an alternative embodiment, using hydrophilic ocular biomaterials, it may be desirable to use ionic dyes (of any color) capable of blocking substantially the entire visible spectrum of electromagnetic radiation while allowing transmission of substantially the entire NIR spectrum of electromagnetic radiation (i.e., a red ionic dye, a blue ionic dye, and a yellow ionic dye to therefore block substantially the entire spectrum of visible electromagnetic radiation).

Regarding the use of a yellow dye to block electromagnetic radiation, any yellow dye may be used which is capable of absorbing electromagnetic radiation in the range of about 350-450 nm, including the ranges of about 355-445 nm, about 360-440 nm, about 365-435 nm, about 370-430 nm, about 375-425 nm, about 380-420 nm, and about 385-415 nm, or any other range of wavelengths selected to be used in a tailored composition of dyes to achieve a desired absorption profile. In some embodiments, the yellow dye absorbs electromagnetic radiation in more than one range, i.e., has more than one lambda max. The yellow dye may include at least one methacrylate or acrylate moiety or other reactive moiety. Such acrylate or methacrylate or other moieties and subsequent covalent bonding, discourages, if not eliminates, a substantial amount of subsequent leaching or release of the dye molecule over time and through extended use. The incorporation of moieties, including but not limited to acrylate and methacrylate moieties, into the dye molecule allows a high degree of covalency and a concomitantly high degree of dye loading. This is particularly useful in ocular devices with particularly thin cross sections as high dye loadings are one technique in these applications to achieve appropriate opacity. At high dye loadings achieving high covalency up to and including 100% may be difficult. As covalency declines, dye bleeding into the surrounding matter can result. For example, dye bleeding into the clear/transparent regions of the IOL or other non-corneal ocular device or, if the device is implanted into the cornea, into the surrounding corneal tissues can occur if covalency is not sufficiently high. Such dye bleeding is highly undesirable in ocular devices. The methacrylated or acrylated dyes disclosed herein may achieve a high degree of covalent bonding sufficient for corneal inlays and other thin cross section ocular devices. These and other similar dyes will be substantially free of dye bleeding associated with insufficient covalency in a thin, high concentration dye structure. Alternatively, the yellow dye may be reacted with a polymer after polymerization using reactive functional groups such as methacrylate or acrylate: the dye linker moiety may be grafted to the polymer after polymerization to achieve substantially the same result as discussed above.

The yellow dyes mentioned in the immediately preceding paragraphs may be particularly useful for incorporation in hydrophobic ocular biomaterials, many of which are known in the art. In an alternative embodiment, using hydrophilic ocular biomaterials, it may be desirable to use ionic dyes (of any color) capable of blocking substantially the entire visible spectrum of electromagnetic radiation while allowing transmission of substantially the entire NIR spectrum of electromagnetic radiation (i.e., a red ionic dye, a blue ionic dye, and a yellow ionic dye to therefore block substantially the entire spectrum of visible electromagnetic radiation).

Regarding incorporation of the aforementioned dyes into a polymeric material, the inventors have found that when using a dye having reactive groups such as an acrylated or methacrylated dye, an effective mode of incorporation into the final product is to solubilize the dye in monomer prior to polymerization. The dyes may also be incorporated into the polymeric material post-polymerization by simply grafting the dye moiety onto the polymer itself after the homopolymer or copolymer has been created.

It may also be advantageous to incorporate an ultraviolet (UV) absorber into the mask material, along with the bandpass dyes that absorb the visible electromagnetic radiation. Such a UV absorber absorbs UV electromagnetic radiation with wavelengths smaller than about 400 nm. Including such a UV absorber protects the other bandpass dyes (such as disperse red 1 acrylate and dimethacrylate of 1,4,-Bis(4-ethylanilino)anthraquinone) preventing UV-induced photobleaching of dye molecules. For example, the protective function provided by UV absorber can be beneficial for the dimethacrylate of 1,4,-bis(4-ethylanilino)anthraquinone because this dye displays considerable absorbance in the range of about 250-300 nm and may therefore be particularly prone to UV induced photobleaching.

In embodiments including UV absorber, the UV absorber may be any UV absorber, or combination of two or more UV absorbers. The UV absorber may include a benzotriazole UV Absorber, such as ([2-(5-chloro-2H-benzotriazole-2-yl)-6-(1,1-dimethylethyl)-4-ethenylphenol, and/or it may include any compound or combination of two or more compounds capable of absorbing electromagnetic radiation in the UV range.

Some embodiments of the mask disclosed herein use both, and only, Disperse Red 1 acrylate (as an orange dye) and dimethacrylate of 1,4,-bis(4-ethylanilino)anthraquinone (as a blue-green dye) in concert with a UV absorber. In this mixture, the disperse red 1 acrylate absorbs in the range of about 390-550 nm, the dimethacrylate of 1,4,-bis(4-ethylanilino)anthraquinone absorbs in the range of about 360-440 & about 520-700 nm, and the UV absorbs in the range of less than about 400 nm (thereby yielding the aforementioned protective benefit). Because such effective blue-green and orange dyes are used, a yellow dye is rendered unnecessary in this formulation and therefore does not need to be included, although it may be included if desired. Provided suitable concentrations of the aforementioned dyes and absorbers are used, substantially the entire visible electromagnetic radiation spectrum is substantially absorbed or blocked.

EXAMPLE 2

Synthesis of NIR Transparent Mask Material

The NIR transparent mask material formulation consisted of:

| | |
|---|---|
| Butyl Acrylate | 51.60% |
| Ethylmethacrylate | 45.07% |
| Benzotriazole UV Absorber | 0.50% |
| Ethyleneglycoldimethacrylate | 0.50% |

-continued

| | |
|---|---|
| Azobisisobutyronitrile | 0.13% |
| Disperse Red 1 Acrylate | 0.20% |
| Dimethacrylate of 1,4,-Bis(4-ethylanilino) anthraquinone | 2.00% |

The following synthesis procedure is directed toward a particular material. However, one skilled in the art may readily adapt this procedure for use with other monomers, UV absorbers, dyes, and the like. The NIR transparent mask material was synthesized in the following manner. For clarity's sake, the percentages referred to herein relate to the weight percent of the total material weight. First the following dye solutions were created: disperse red 1 acrylate (2-[N-ethyl-4-[(4-nitrophenyl)diazenyl]anilino]ethyl prop-2-enoate) in butyl acrylate and dimethacrylate of 1,4,-bis(4-ethylanilino)anthraquinone (2-[4-({4-[(4-{2-[(2-methylprop-2-enoyl)oxy]ethyl}phenyl)amino]-9,10-dioxo-9,10-dihydro-anthracen-1-yl}amino)phenyl]ethyl-2-methyl prop-2-enoate in ethylmethacrylate. To create the disperse red 1 acrylate dye and butyl acrylate solution, 0.2% disperse red 1 acrylate was added to 51.60% butyl acrylate. To create the dimethacrylate of 1,4,-bis(4-ethylanilino)dye and ethylmethacrylate solution, 2.00% dimethacrylate of 1,4,-bis(4-ethylanilino)anthraquinone was added to 45.07% ethylmethacrylate. The dye solutions were then sonicated well until the dyes had fully dissolved in their respective solutions and then were set aside. 0.13% azobisisobutyronitrile and 0.5% benzotriazole UV absorber were weighed into a flask and the following was then added: 51.60% butyl acrylate/0.2% disperse red 1 acrylate dye solution (made previously), 45.07% ethylmethacrylate/2.00% dimethacrylate of 1,4,-bis (4-ethylanilino) solution (made previously), and 0.5% ethyleneglycoldimethylacrlylate. The mixture was purged with nitrogen and stirred for one hour without heat. To cure, glass molds were filled with the material. The molds were transferred to an oven and the mixture cured using the following time and temperature parameters: ramp 10 minutes to 65° C., hold 12 hours at 65° C., ramp 1 hour to 110° C., hold 4 hours at 110° C., ramp 2 hours to 30° C.

To create the NIR transparent mask material, some parameters may be altered. For example, disperse red 1 acrylate may be used in the range of about 0.1%-1.0%, including the ranges of about 0.12%-0.8%, about 0.14%-0.6%, about 0.16%-0.4%, and about 0.18%-0.3%, including about 0.2%, or any other concentration of disperse red 1 acrylate which provides a desired absorption profile. Dimethacrylate of 1,4,-bis(4-ethylanilino)anthraquinone may be used in the range of about 1.0%-3.0%, including the ranges of about 1.2%-2.8%, about 1.4%-2.6%, about 1.6%-2.4%, and about 1.8%-2.2%, including about 2.0%, or any other concentration of dimethacrylate of 1,4,-Bis(4-ethylanilino)anthraquinone which provides a desired absorption profile. Butyl acrylate, to which the disperse red 1 acrylate dye is added, may be used in the range of about 30%-70%, including the ranges of about 35%-65%, about 40%-60%, and about 45%-55%, including about 50%, or any other concentration of butyl acrylate which allows the formation of the NIR transparent mask material. Ethylmethacrylate, to which the dimethacrylate of 1,4,-bis(4-ethylanilino)anthraquinone is added, may be used in the range of about 25%-65%, including the ranges of about 30%-60%, about 35%-55%, about 40%-50%, and about 42%-46%, including about 44%, or any other concentration of ethylmethacrylate which allows the formation of the NIR transparent mask material. Azobisisobutyronitrile may be used in the range of about 0.05%-0.5%, including the ranges of about 0.07%-0.40%, about 0.9%-0.30%, and about 0.11%-0.20%, including about 0.13%, or any other concentration of azobisisobutyronitrile which allows the formation of the NIR transparent mask material. Ethyleneglycoldimethacrylate may be used in the range of about 0.025%-10.0%, including the ranges of about 0.075%-9.0%, about 0.125%-8.0%, about 0.175%-7.0%, about 0.225%-6.0%, about 0.275%-5.0%, about 0.325%-4.0%, about 0.375%-3.0%, about 0.425%-2.0%, about 0.475%-1.0%, including about 0.5%, or any other concentration of ethyleneglycoldimethacrylate which allows the formation of the NIR transparent mask material. Benzotriazole UV absorber may be used in the range of about 0.0%-2.5%, including the ranges of about 0.0%-2.0%, about 0.0%-1.5%, and about 0.0%-1.0%, including about 0.5%, or any other concentration of benzotriazole UV absorber which allows the formation of the NIR transparent mask material. In addition to varying the amounts, other dyes, solvents, UV absorbers, monomers, polymers and the like may be substituted as desired to make materials suitable for use as a mask.

When all the aforementioned chemicals are mixed together, the mixture may be placed under a nitrogen stream or any inert or generally unreactive gas stream, including for example helium, neon, argon, krypton, and xenon.

The time parameters given, including stiffing times, heating times, and resting times may be altered to any times which allow the proper chemical and/or physical reaction to occur. Furthermore, the temperature parameters may be altered to any temperatures which allow the proper chemical and/or physical reactions to occur. The disclosed times and temperatures are intended to be representative of only one possibility among many and are understood not to limit the scope of this disclosure.

The dyes disclosed herein may be used in concert with any polymer determined to be appropriate for ocular uses by one of ordinary skill in the art. Any concentration of any number of varied colored absorbing dyes (including orange, yellow and green and any other such absorbing dyes) may be used with or without a UV absorber. As the dyes are functionalized with acryl or methacryl or other suitable moieties, they may be reacted with any number of polymer units prior to or after polymerization in any concentration possible and desired.

Figure 67:
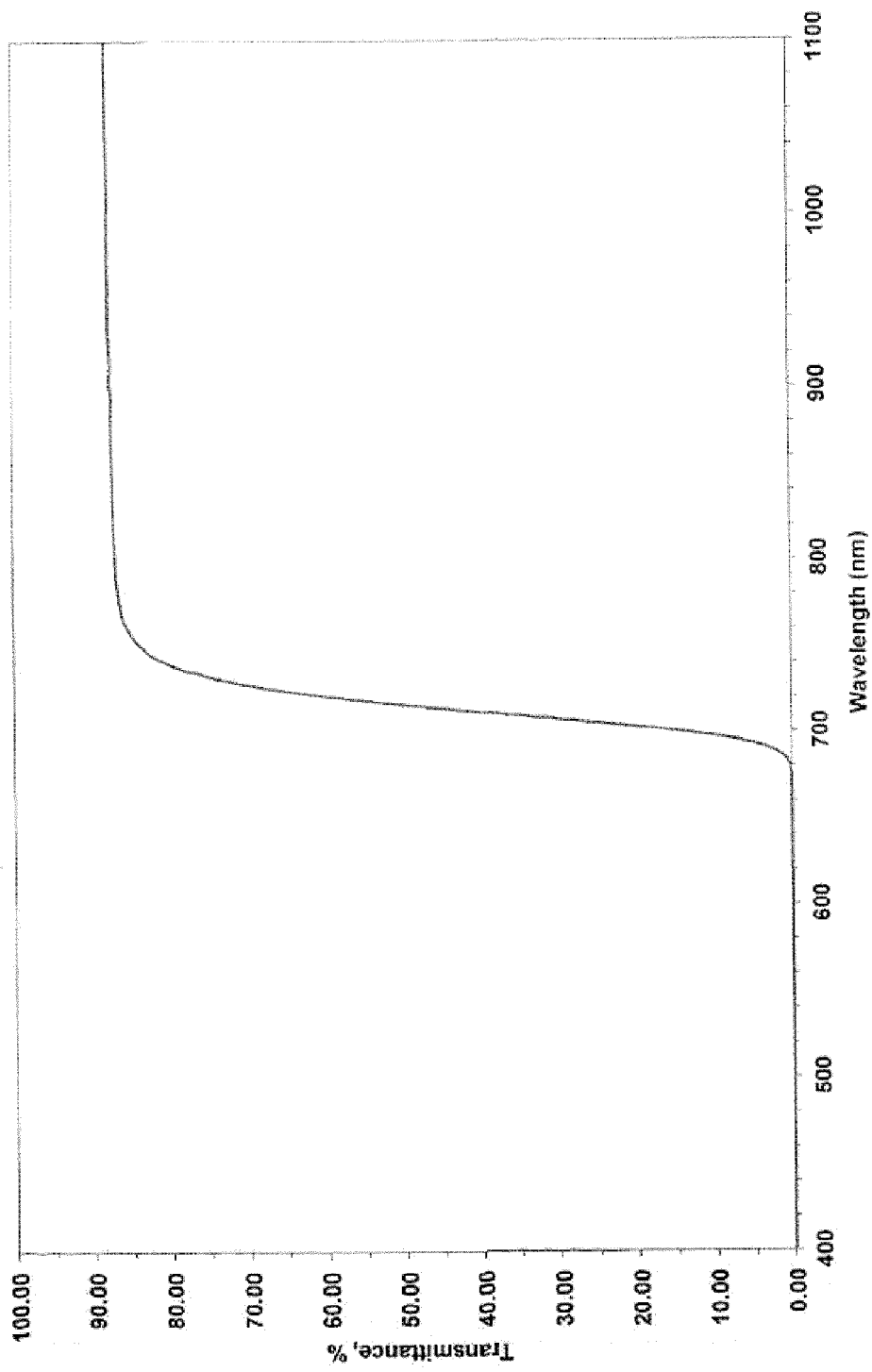
FIG. 67 shows a transmission spectrum of a 200 micron thick hydrophobic acrylic mask.

Using the aforementioned bandpass dyes and UV absorber, it is clear that the embodiments disclosed herein envision tailorability, through bandpass dye choice and concentration, of the electromagnetic radiation allowed to pass through the mask. For example, the ocular device may comprise one or more materials which obstruct the majority of visible light wavelengths up to about 750 nm and transmit in the range of about 750 nm to about 1300 nm. Similarly, the ocular device may transmit up to a wavelength of about 1500 nm or the ocular device may transmit in the range of about 1050 nm to about 1300 nm. Allowing transmission in these ranges will make the inlay and/or IOL mask effectively invisible to a diagnostic OCT light source. By way of example, a material that uses the orange dye, disperse red 1 acrylate, and the blue-green dye, dimethacrylate of 1,4,-Bis (4-ethylanilino)anthraquinone, and the benzotriazole UV Absorber has been observed to block about 99% of all visible electromagnetic radiation in the range of about 400 to about 700 nm, while allowing substantially all Near Infrared (NIR) electromagnetic radiation, greater than about 700 nm, to pass through the mask. FIG. 67 shows a transmission spectrum of a 200 micron thick hydrophobic acrylic mask produced by the inventors using the methods and materials disclosed herein. As can be seen, the inventors succeeded in blocking substantially the entire visible spectrum of electromagnetic radiation while allowing the transmission of substantially the entire NIR spectrum of electromagnetic radiation.

Intraocular lenses may be implanted in older patients who are more likely to have concurrent retinal complications. Unlike a corneal inlay which may be easily removed, the IOL removal procedure is non-trivial. Therefore, it is particularly important that any mask included in or on an IOL not impede imaging of the eye using NIR techniques.

Although certain inlays with a small-aperture mask may not impede retinal examination with OCT (see, e.g., Casas-Llera et al, "Retinal imaging after corneal inlay implantation," Journal of Cataract & Refractive Surgery, Vol. 37, Issue 9, September 2011, pages 1729-1731, the entirety of which is hereby incorporated by reference), some practitioners could still consider the mask to be obstructive to retinal examination especially given that minimum pupil size provided by OCT manufacturers is ≥2 mm. Furthermore, an IOL with a small-aperture mask may not similarly allow OCT examination. Use of a mask with materials that are more amenable to retinal examination, such as those mentioned above, could provide improved usability and market acceptability. Use of such materials in corneal inlays and IDLs may aid in improved retinal examination with OCT.

In some applications, the masks are formed of a material substantially opaque to visible light while being selectively transparent to certain other wavelengths of electromagnetic radiation. The substantially opaque material can be used in connection with any of the masks described herein. The mask can also include any of the features described above.

For example, an ocular device includes a material that obstructs visible light up to 750 nm and transmits in the range of 750 to 1500 nm. Allowing transmission in these ranges will make the inlay and an IOL mask invisible to the diagnostic OCT light source. Such an ocular device would be invisible to the electromagnetic spectrum used by diagnostic devices. This would aid clinicians in examining the ocular tissues in both anterior and posterior segments of the eye.

The ocular device can comprise one or more polymeric compounds that would have substantially 100% transmission in the spectral ranges of about 750 nm to about 1500 nm (NIR) while being substantially opaque in visible ranges. For example, vinyl-functional dyes of yellow, red, and green, each with band pass transmission in selective regions of the visible spectrum, can be blended into a mixture of monomers that form the polymer matrix. The mixture can include a cross-linking molecule and a thermal initiator. The mixture can be introduced into a pocket in a base polymer blank and cured in-situ to form the mask and the lens can be machined from this blank with the mask. In another example, non-functional dyes with band pass transmission in selected regions of the visible spectrum such as disperse yellow, disperse red, and solvent green 3 can be mixed in with PVDF and DMAC solvent which can then be spun-cast. Other example uses are described in Patel C K, Yusuf N I and Menezo V, "Imaging the macula through a black occlusive intraocular lens," Arch Ophthalmol 2010, 128: 1374-1376 and Yusuf I H, Peirson S H and Patel C K, "Occlusive IDLs for intractable diplopia demonstrate a novel near-Infrared window of transmission for SLO/OCT imaging and clinical assessment," IOVS, 2011, 52: 3737-3743, the entirety of each of which is hereby incorporated by reference. To the naked eye and to standard clinical examination, the mask would appear opaque and similar to certain conventional masks that are opaque to both visible and NIR spectral ranges. However, the mask would be invisible when viewed with a NIR light source (e.g., the mask would permit transmission of NIR).

Various embodiments have been described above. Although the invention has been described with reference to these specific embodiments, the descriptions are intended to be illustrative and are not intended to be limiting. Various modifications and applications may occur to those skilled in the art without departing from the true spirit and scope of the invention as defined in the appended claims.

What is claimed is:

1. An ophthalmic device comprising:
an implantable mask configured to increase the depth of focus of a human patient when the mask is implanted in an eye of the human patient, the mask comprising an aperture configured to transmit along an optical axis substantially all visible incident light,
the mask further comprising a structure surrounding the aperture, the structure configured to be substantially opaque to visible light and to be substantially transparent to at least some non-visible electromagnetic radiation with a wavelength between about 750 nm and about 1500 nm to facilitate examining ocular tissue posterior to the mask.

2. The ophthalmic device of claim 1 further comprising a plurality of holes in the structure, wherein the plurality of holes are interspersed in an irregular pattern and configured to permit a bond to form between lens body portions on either side of the mask.

3. The ophthalmic device of claim 2, wherein each of the plurality of holes has a diameter between about 0.01 mm and 0.02 mm.

4. The ophthalmic device of claim 1, wherein the structure comprises at least one dye capable of absorbing electromagnetic radiation.

5. The ophthalmic device of claim 4, wherein the at least one dye comprises a first dye, the first dye absorbing a first range of electromagnetic radiation wavelengths, and a second dye, the second dye absorbing a second range of electromagnetic radiation wavelengths.

6. The ophthalmic device of claim 5, wherein the first range of electromagnetic radiation wavelengths and the second range of electromagnetic radiation wavelengths include substantially all the range of visible electromagnetic radiation thereby absorbing substantially all the range of visible electromagnetic radiation, and wherein the first range of electromagnetic radiation wavelengths and the second range of electromagnetic radiation wavelengths do not include a substantial range of the near infrared range of electromagnetic radiation thereby allowing transmission of substantially all the range of near infrared electromagnetic radiation.

7. The ophthalmic device of claim 5, wherein the at least one dye further comprises a third dye, the third dye absorbing a third range of electromagnetic radiation wavelengths.

8. The ophthalmic device of claim 7, wherein the first range of electromagnetic radiation wavelengths, the second range of electromagnetic radiation wavelengths, and the third range of electromagnetic radiation wavelengths include substantially all the range of visible electromagnetic radiation thereby absorbing substantially all the range of visible electromagnetic radiation, and wherein the first range of electromagnetic radiation wavelengths, the second range of electromagnetic radiation wavelengths, and the third range of electromagnetic radiation wavelengths do not include a substantial range of the near infrared range of electromagnetic radiation thereby allowing transmission of substantially all the range of near infrared electromagnetic radiation.

9. The ophthalmic device of claim 7, wherein the first dye is an orange dye, the second dye is a blue-green dye, and the third dye is a yellow dye.

10. The ophthalmic device of claim 5, wherein the first dye is an orange dye and wherein the second dye is a blue-green dye.

11. The ophthalmic device of claim 10, wherein the orange dye is 2-[N-ethyl-4-[(4-nitrophenyl)diazenyl]anilino]ethyl prop-2-enoate.

12. The ophthalmic device of claim 10, wherein the blue-green dye is 2-[4-({4-[(4-{2-[(2-methylprop-2-enoyl)oxy]ethyl}phenyl)amino]-9,10-dioxo-9,10-dihydro-anthracen-1-yl}amino)phenyl]ethyl-2-methyl prop-2-enoate.

13. The ophthalmic device of claim 4, further comprising a UV blocker, wherein the UV blocker blocks at least some of the UV range of electromagnetic radiation.

14. The ophthalmic device of claim 13, wherein the UV blocker is a benzotriazole UV blocker.

15. The ophthalmic device of claim 13, wherein the UV blocker is ([2-(5-Chloro-2H-Benzotriazole-2-yl)-6-(1,1-dimethylethyl)-4-ethenylphenol.

16. The ophthalmic device of claim 4, further comprising a UV blocker, wherein said UV blocker is ([2-(5-Chloro-2H-Benzotriazole-2-yl)-6-(1,1-dimethylethyl)-4-ethenyl-phenol, wherein the at least one dye comprises 2-[N-ethyl-4-[(4-nitrophenyl)diazenyl]anilino]ethyl prop-2-enoate and 2-[4-({4-[(4-{2-[(2-methylprop-2-enoyl)oxy]ethyl}phenyl)amino]-9,10-dioxo-9,10-dihydro-anthracen-1-yl}amino)phenyl]ethyl-2-methyl prop-2-enoate.

17. The ophthalmic device of claim 1, wherein the mask is coupled to a lens body.

18. The ophthalmic device of claim 17, wherein the mask is embedded within the lens body.

19. An ophthalmic device configured to increase the depth of focus of a patient, comprising
a first zone configured to transmit along an optical axis a majority of visible incident light; and
a mask disposed about the first zone, the mask comprising a plurality of holes and a portion surrounding each of the plurality of holes, the portion surrounding the plurality of holes being substantially opaque to visible light and substantially transparent to at least some non-visible electromagnetic radiation with a wavelength between about 750 nm and about 1500 nm.

20. The ophthalmic device of claim 19, wherein the mask is substantially transparent to at least some electromagnetic radiation in the near infrared spectrum.

21. The ophthalmic device of claim 19, wherein the mask is coupled to a lens body.

22. The ophthalmic device of claim 21, wherein the mask is embedded in the lens body.

23. The ophthalmic device of claim 22, wherein the lens body comprises a lens material, the lens material extending through the plurality of holes of the mask.

24. A method of examining an eye of a patient having an implantable pinhole imaging device configured to increase the depth of focus of a human patient disposed therein, the pinhole imaging device comprising an aperture configured to transmit along an optical axis substantially all visible incident light, the method comprising: aligning a source of electromagnetic radiation with a portion of the pinhole imaging device that is substantially non-transmissive to light in the visible range; and transmitting electromagnetic radiation with a wavelength between about 750 nm and about 1500 nm through the substantially non-transmissive portion.

25. The method of claim 24, further comprising:
providing an optical coherence tomography device having a patient interface; and
engaging the patient with the patient interface.

26. The method of claim 25, further comprising transmitting electromagnetic radiation with a wavelength between about 750 nm and about 1500 nm through the aperture of the pinhole imaging device.

27. The method of claim 26, wherein the electromagnetic radiation is simultaneously transmitted through the aperture and the substantially non-transmissive portion of the pinhole imaging device.

* * * * *